United States Patent
Quanci et al.

(10) Patent No.: US 12,286,591 B2
(45) Date of Patent: Apr. 29, 2025

(54) COAL BLENDS, FOUNDRY COKE PRODUCTS, AND ASSOCIATED SYSTEMS, DEVICES, AND METHODS

(71) Applicant: SUNCOKE TECHNOLOGY AND DEVELOPMENT LLC, Lisle, IL (US)

(72) Inventors: John Francis Quanci, Haddonfield, NJ (US); John Michael Richardson, Devon, PA (US); Jonathan Hale Perkins, Lisle, IL (US)

(73) Assignee: SUNCOKE TECHNOLOGY AND DEVELOPMENT LLC, Lisle, IL (US)

( * ) Notice: Subject to any disclaimer, the term of this patent is extended or adjusted under 35 U.S.C. 154(b) by 0 days.

(21) Appl. No.: 18/501,795

(22) Filed: Nov. 3, 2023

(65) Prior Publication Data
US 2024/0150659 A1 May 9, 2024

Related U.S. Application Data

(60) Provisional application No. 63/382,446, filed on Nov. 4, 2022.

(51) Int. Cl.
*C10B 15/02* (2006.01)
*C10B 5/02* (2006.01)
(Continued)

(52) U.S. Cl.
CPC ............ *C10B 57/06* (2013.01); *C10B 5/02* (2013.01); *C10B 15/02* (2013.01); *C10B 21/10* (2013.01); *C10B 41/00* (2013.01); *C10B 53/00* (2013.01); *C10B 57/04* (2013.01); *C10B 57/16* (2013.01); *C10L 5/04* (2013.01); *C10L 5/442* (2013.01);
(Continued)

(58) Field of Classification Search
CPC ......... C10B 53/04; C10B 57/04; C10B 57/06; C10B 15/02; C10B 41/00
See application file for complete search history.

(56) References Cited

U.S. PATENT DOCUMENTS

| 425,797 A | 4/1890 | Hunt |
| 469,868 A | 3/1892 | Osbourn |

(Continued)

FOREIGN PATENT DOCUMENTS

| CA | 1172895 | 8/1984 |
| CA | 2775992 | 5/2011 |

(Continued)

OTHER PUBLICATIONS

U.S. Appl. No. 18/313,622, filed May 8, 2023, Quanci et al.
(Continued)

*Primary Examiner* — Jonathan Luke Pilcher
(74) *Attorney, Agent, or Firm* — Perkins Coie LLP; Vijay S. Kumar

(57) ABSTRACT

Methods and systems for coking coal blends to produce foundry coke products are disclosed herein. Methods for producing coke products can include charging a coal blend into a coke oven; and heating the charged coal blend such that a crown temperature of the coke oven is greater than a lower bound coking temperature. The pyrolysis duration begins when the crown temperature of the oven is greater than the lower bound coking temperature, and ends when the crown temperature of the oven is less than the lower bound coking temperature.

21 Claims, 24 Drawing Sheets

(51) Int. Cl.

| | | |
|---|---|---|
| *C10B 21/10* | (2006.01) | |
| *C10B 41/00* | (2006.01) | |
| *C10B 53/00* | (2006.01) | |
| *C10B 57/04* | (2006.01) | |
| *C10B 57/06* | (2006.01) | |
| *C10B 57/16* | (2006.01) | |
| *C10L 5/04* | (2006.01) | |
| *C10L 5/44* | (2006.01) | |
| *C10L 5/48* | (2006.01) | |
| *G01N 33/22* | (2006.01) | |

(52) U.S. Cl.
CPC ............. *C10L 5/48* (2013.01); *G01N 33/222* (2013.01); *C10L 2290/24* (2013.01); *C10L 2290/60* (2013.01)

(56) References Cited

U.S. PATENT DOCUMENTS

| | | |
|---|---|---|
| 705,926 A | 7/1902 | Hemingway |
| 760,372 A | 5/1904 | Beam |
| 845,719 A | 2/1907 | Schniewind |
| 875,989 A | 1/1908 | Garner |
| 976,580 A | 7/1909 | Krause |
| 1,140,798 A | 5/1915 | Carpenter |
| 1,378,782 A | 5/1921 | Floyd |
| 1,424,777 A | 8/1922 | Schondeling |
| 1,429,346 A | 9/1922 | Horn |
| 1,430,027 A | 9/1922 | Plantinga |
| 1,486,401 A | 3/1924 | Ackeren |
| 1,530,995 A | 3/1925 | Geiger |
| 1,572,391 A | 2/1926 | Klaiber |
| 1,677,973 A | 7/1928 | Marquard |
| 1,705,039 A | 3/1929 | Thornhill |
| 1,721,813 A | 7/1929 | Geipert |
| 1,757,682 A | 5/1930 | Palm |
| 1,818,370 A | 8/1931 | Wine |
| 1,818,994 A | 8/1931 | Kreisinger |
| 1,830,951 A | 11/1931 | Lovett |
| 1,848,818 A | 3/1932 | Becker |
| 1,895,202 A | 1/1933 | Montgomery |
| 1,947,499 A | 2/1934 | Schrader et al. |
| 1,955,962 A | 4/1934 | Jones |
| 1,979,507 A | 11/1934 | Underwood |
| 2,075,337 A | 3/1937 | Burnaugh |
| 2,141,035 A | 12/1938 | Daniels |
| 2,195,466 A | 4/1940 | Otto |
| 2,235,970 A | 3/1941 | Wilputte |
| 2,340,283 A | 1/1944 | Vladu |
| 2,340,981 A | 2/1944 | Otto |
| 2,343,034 A | 2/1944 | Weber |
| 2,394,173 A | 2/1946 | Harris et al. |
| 2,424,012 A | 7/1947 | Bangham et al. |
| 2,486,199 A | 10/1949 | Nier |
| 2,609,948 A | 9/1952 | Laveley |
| 2,641,575 A | 6/1953 | Otto |
| 2,649,978 A | 8/1953 | Smith |
| 2,667,185 A | 1/1954 | Beavers |
| 2,723,725 A | 11/1955 | Keiffer |
| 2,756,842 A | 7/1956 | Chamberlin et al. |
| 2,765,266 A * | 10/1956 | Throop ............... C10B 57/04 202/262 |
| 2,813,708 A | 11/1957 | Frey |
| 2,827,424 A | 3/1958 | Homan |
| 2,873,816 A | 2/1959 | Emil et al. |
| 2,902,991 A | 9/1959 | Whitman |
| 2,907,698 A | 10/1959 | Schulz |
| 2,968,083 A | 1/1961 | Lentz et al. |
| 3,010,882 A | 11/1961 | Barclay et al. |
| 3,015,893 A | 1/1962 | McCreary |
| 3,026,715 A | 3/1962 | Briggs |
| 3,033,764 A | 5/1962 | Hannes |
| 3,085,582 A * | 4/1963 | Slosman ............... C10B 45/00 198/572 |
| 3,175,961 A | 3/1965 | Samson |
| 3,199,135 A | 8/1965 | Trucker |
| 3,224,805 A | 12/1965 | Clyatt |
| 3,259,551 A | 7/1966 | Thompson, Jr. |
| 3,265,044 A | 8/1966 | Juchtern |
| 3,267,913 A | 8/1966 | Jakob |
| 3,327,521 A | 6/1967 | Briggs |
| 3,342,990 A | 9/1967 | Barrington et al. |
| 3,444,046 A | 5/1969 | Harlow |
| 3,444,047 A | 5/1969 | Wilde |
| 3,448,012 A | 6/1969 | Allred |
| 3,453,839 A | 7/1969 | Sabin |
| 3,462,345 A | 8/1969 | Kernan |
| 3,462,346 A * | 8/1969 | Kernan ............... C10B 9/00 202/113 |
| 3,511,030 A | 5/1970 | Brown et al. |
| 3,542,650 A | 11/1970 | Kulakov |
| 3,545,470 A | 12/1970 | Paton |
| 3,587,198 A | 6/1971 | Hensel |
| 3,591,827 A | 7/1971 | Hall |
| 3,592,742 A | 7/1971 | Thompson |
| 3,616,408 A | 10/1971 | Hickam |
| 3,623,511 A | 11/1971 | Levin |
| 3,630,852 A | 12/1971 | Nashan et al. |
| 3,652,403 A | 3/1972 | Knappstein et al. |
| 3,676,305 A | 7/1972 | Cremer |
| 3,709,794 A | 1/1973 | Kinzler et al. |
| 3,710,551 A | 1/1973 | Sved |
| 3,746,626 A | 7/1973 | Morrison, Jr. |
| 3,748,235 A | 7/1973 | Pries |
| 3,784,034 A | 1/1974 | Thompson |
| 3,806,032 A | 4/1974 | Pries |
| 3,811,572 A | 5/1974 | Tatterson |
| 3,836,161 A | 10/1974 | Pries |
| 3,839,156 A | 10/1974 | Jakobi et al. |
| 3,844,900 A | 10/1974 | Schulte |
| 3,857,758 A | 12/1974 | Mole |
| 3,875,016 A | 4/1975 | Schmidt-Balve |
| 3,876,143 A | 4/1975 | Rossow et al. |
| 3,876,506 A | 4/1975 | Dix et al. |
| 3,878,053 A | 4/1975 | Hyde |
| 3,894,302 A | 7/1975 | Lasater |
| 3,897,312 A | 7/1975 | Armour et al. |
| 3,906,992 A | 9/1975 | Leach |
| 3,912,091 A | 10/1975 | Thompson |
| 3,912,597 A | 10/1975 | MacDonald |
| 3,917,458 A | 11/1975 | Polak |
| 3,928,144 A | 12/1975 | Jakimowicz |
| 3,930,961 A | 1/1976 | Sustarsic et al. |
| 3,933,443 A | 1/1976 | Lohrmann |
| 3,957,591 A | 5/1976 | Riecker |
| 3,959,084 A | 5/1976 | Price |
| 3,963,582 A | 6/1976 | Helm et al. |
| 3,969,191 A | 7/1976 | Bollenbach |
| 3,975,148 A | 8/1976 | Fukuda et al. |
| 3,979,870 A | 9/1976 | Moore |
| 3,984,289 A | 10/1976 | Sustarsic et al. |
| 3,990,948 A | 11/1976 | Lindgren |
| 4,004,702 A | 1/1977 | Szendroi |
| 4,004,983 A | 1/1977 | Pries |
| 4,025,395 A | 5/1977 | Ekholm et al. |
| 4,040,910 A | 8/1977 | Knappstein et al. |
| 4,045,056 A | 8/1977 | Kandakov et al. |
| 4,045,299 A | 8/1977 | McDonald |
| 4,059,885 A | 11/1977 | Oldengott |
| 4,065,059 A | 12/1977 | Jablin |
| 4,067,462 A | 1/1978 | Thompson |
| 4,077,848 A | 3/1978 | Grainer et al. |
| 4,083,753 A | 4/1978 | Rogers et al. |
| 4,086,231 A | 4/1978 | Ikio |
| 4,093,245 A | 6/1978 | Connor |
| 4,100,033 A | 7/1978 | Holter |
| 4,100,491 A | 7/1978 | Newman, Jr. et al. |
| 4,100,889 A | 7/1978 | Chayes |
| 4,111,757 A | 9/1978 | Carimboli |
| 4,124,450 A * | 11/1978 | MacDonald ............... C10B 9/00 201/15 |
| 4,133,720 A | 1/1979 | Franzer et al. |
| 4,135,948 A | 1/1979 | Mertens et al. |

(56) References Cited

U.S. PATENT DOCUMENTS

| | | |
|---|---|---|
| 4,141,796 A | 2/1979 | Clark et al. |
| 4,143,104 A | 3/1979 | van Konijnenburg et al. |
| 4,145,195 A | 3/1979 | Knappstein et al. |
| 4,147,230 A | 4/1979 | Ormond et al. |
| 4,162,546 A | 7/1979 | Shortell et al. |
| 4,176,013 A | 11/1979 | Garthus et al. |
| 4,181,459 A | 1/1980 | Price |
| 4,189,272 A | 2/1980 | Gregor et al. |
| 4,194,951 A | 3/1980 | Pries |
| 4,196,053 A | 4/1980 | Grohmann |
| 4,211,608 A | 7/1980 | Kwasnoski et al. |
| 4,211,611 A | 7/1980 | Bocsanczy |
| 4,213,489 A | 7/1980 | Cain |
| 4,213,828 A | 7/1980 | Calderon |
| 4,222,748 A | 9/1980 | Argo et al. |
| 4,222,824 A | 9/1980 | Flockenhaus et al. |
| 4,224,109 A | 9/1980 | Flockenhaus et al. |
| 4,225,393 A | 9/1980 | Gregor et al. |
| 4,226,113 A | 10/1980 | Pelletier et al. |
| 4,230,498 A | 10/1980 | Ruecki |
| 4,235,830 A | 11/1980 | Bennett et al. |
| 4,239,602 A | 12/1980 | La Bate |
| 4,248,671 A | 2/1981 | Belding |
| 4,249,997 A | 2/1981 | Schmitz |
| 4,263,099 A | 4/1981 | Porter |
| 4,268,360 A | 5/1981 | Tsuzuki et al. |
| 4,271,814 A | 6/1981 | Lister |
| 4,284,478 A | 8/1981 | Brommel |
| 4,285,772 A | 8/1981 | Kress |
| 4,287,024 A | 9/1981 | Thompson |
| 4,289,479 A | 9/1981 | Johnson |
| 4,289,584 A | 9/1981 | Chuss et al. |
| 4,289,585 A | 9/1981 | Wagener et al. |
| 4,296,938 A | 10/1981 | Offermann et al. |
| 4,298,497 A | 11/1981 | Colombo |
| 4,299,666 A | 11/1981 | Ostmann |
| 4,302,935 A | 12/1981 | Cousimano |
| 4,303,615 A | 12/1981 | Jarmell et al. |
| 4,307,673 A | 12/1981 | Caughey |
| 4,314,787 A | 2/1982 | Kwasnik et al. |
| 4,316,435 A | 2/1982 | Nagamatsu et al. |
| 4,324,568 A | 4/1982 | Wilcox et al. |
| 4,330,372 A | 5/1982 | Cairns et al. |
| 4,334,963 A | 6/1982 | Stog |
| 4,336,107 A | 6/1982 | Irwin |
| 4,336,843 A | 6/1982 | Petty |
| 4,340,445 A | 7/1982 | Kucher et al. |
| 4,342,195 A | 8/1982 | Lo |
| 4,344,820 A | 8/1982 | Thompson |
| 4,344,822 A | 8/1982 | Schwartz et al. |
| 4,353,189 A | 10/1982 | Thiersch et al. |
| 4,366,029 A | 12/1982 | Bixby et al. |
| 4,373,244 A | 2/1983 | Mertens et al. |
| 4,375,388 A | 3/1983 | Hara et al. |
| 4,385,962 A | 5/1983 | Stewen et al. |
| 4,391,674 A | 7/1983 | Velmin et al. |
| 4,392,824 A | 7/1983 | Struck et al. |
| 4,394,217 A | 7/1983 | Holz et al. |
| 4,395,269 A | 7/1983 | Schuler |
| 4,396,394 A | 8/1983 | Li et al. |
| 4,396,461 A | 8/1983 | Neubaum et al. |
| 4,406,619 A | 9/1983 | Oldengott |
| 4,407,237 A | 10/1983 | Merritt |
| 4,421,070 A | 12/1983 | Sullivan |
| 4,431,484 A | 2/1984 | Weber et al. |
| 4,439,277 A | 3/1984 | Dix |
| 4,440,098 A | 4/1984 | Adams |
| 4,441,892 A | 4/1984 | Schuster |
| 4,445,977 A | 5/1984 | Husher |
| 4,446,018 A | 5/1984 | Cerwick |
| 4,448,541 A | 5/1984 | Lucas |
| 4,452,749 A | 6/1984 | Kolvek et al. |
| 4,459,103 A | 7/1984 | Gieskieng |
| 4,469,446 A | 9/1984 | Goodboy |
| 4,474,344 A | 10/1984 | Bennett |
| 4,487,137 A | 12/1984 | Horvat et al. |
| 4,498,786 A | 2/1985 | Ruscheweyh |
| 4,506,025 A | 3/1985 | Kleeb et al. |
| 4,508,539 A | 4/1985 | Nakai |
| 4,518,461 A | 5/1985 | Gelfand |
| 4,527,488 A | 7/1985 | Lindgren |
| 4,564,420 A | 1/1986 | Spindeler et al. |
| 4,568,424 A * | 2/1986 | Bauer ............... C10B 21/20 201/1 |
| 4,568,426 A | 2/1986 | Orlando |
| 4,570,670 A | 2/1986 | Johnson |
| 4,614,567 A | 9/1986 | Stahlherm et al. |
| 4,643,327 A | 2/1987 | Campbell |
| 4,645,513 A | 2/1987 | Kubota et al. |
| 4,655,193 A | 4/1987 | Blacket |
| 4,655,804 A | 4/1987 | Kercheval et al. |
| 4,666,675 A | 5/1987 | Parker et al. |
| 4,680,167 A | 7/1987 | Orlando |
| 4,690,689 A | 9/1987 | Malcosky et al. |
| 4,704,195 A | 11/1987 | Janicka et al. |
| 4,720,262 A | 1/1988 | Durr et al. |
| 4,724,976 A | 2/1988 | Lee |
| 4,726,465 A | 2/1988 | Kwasnik et al. |
| 4,732,652 A | 3/1988 | Durselen et al. |
| 4,749,446 A | 6/1988 | van Laar et al. |
| 4,793,981 A | 12/1988 | Doyle et al. |
| 4,821,473 A | 4/1989 | Cowell |
| 4,824,614 A | 4/1989 | Jones et al. |
| 4,889,698 A | 12/1989 | Moller et al. |
| 4,898,021 A | 2/1990 | Weaver et al. |
| 4,918,975 A | 4/1990 | Voss |
| 4,919,170 A | 4/1990 | Kallinich et al. |
| 4,929,179 A | 5/1990 | Breidenbach et al. |
| 4,941,824 A | 7/1990 | Holter et al. |
| 5,013,408 A | 5/1991 | Asai et al. |
| 5,052,922 A | 10/1991 | Stokman et al. |
| 5,062,925 A | 11/1991 | Durselen et al. |
| 5,078,822 A | 1/1992 | Hodges et al. |
| 5,087,328 A | 2/1992 | Wegerer et al. |
| 5,114,542 A | 5/1992 | Childress et al. |
| 5,213,138 A | 5/1993 | Presz |
| 5,227,106 A | 7/1993 | Kolvek |
| 5,228,955 A | 7/1993 | Westbrook, III |
| 5,234,601 A | 8/1993 | Janke et al. |
| 5,318,671 A | 6/1994 | Pruitt |
| 5,370,218 A | 12/1994 | Johnson et al. |
| 5,398,543 A | 3/1995 | Fukushima et al. |
| 5,423,152 A | 6/1995 | Kolvek |
| 5,447,606 A | 9/1995 | Pruitt |
| 5,480,594 A | 1/1996 | Wilkerson et al. |
| 5,542,650 A | 8/1996 | Abel et al. |
| 5,597,452 A | 1/1997 | Hippe et al. |
| 5,603,810 A | 2/1997 | Michler |
| 5,622,280 A | 4/1997 | Mays et al. |
| 5,659,110 A | 8/1997 | Herden et al. |
| 5,670,025 A | 9/1997 | Baird |
| 5,687,768 A | 11/1997 | Albrecht et al. |
| 5,705,037 A | 1/1998 | Reinke et al. |
| 5,715,962 A | 2/1998 | McDonnell |
| 5,720,855 A | 2/1998 | Baird |
| 5,745,969 A | 5/1998 | Yamada et al. |
| 5,752,548 A | 5/1998 | Matsumoto et al. |
| 5,752,993 A | 5/1998 | Eatough et al. |
| 5,787,821 A | 8/1998 | Bhat et al. |
| 5,810,032 A | 9/1998 | Hong et al. |
| 5,816,210 A | 10/1998 | Yamaguchi |
| 5,857,308 A | 1/1999 | Dismore et al. |
| 5,881,551 A | 3/1999 | Dang |
| 5,913,448 A | 6/1999 | Mann et al. |
| 5,928,476 A | 7/1999 | Daniels |
| 5,966,886 A | 10/1999 | Di Loreto |
| 5,968,320 A | 10/1999 | Sprague |
| 6,002,993 A | 12/1999 | Naito et al. |
| 6,003,706 A | 12/1999 | Rosen |
| 6,017,214 A | 1/2000 | Sturgulewski |
| 6,022,112 A | 2/2000 | Isler et al. |
| 6,059,932 A | 5/2000 | Sturgulewski |
| 6,126,910 A | 10/2000 | Wilhelm et al. |
| 6,139,692 A | 10/2000 | Tamura et al. |

(56) References Cited

U.S. PATENT DOCUMENTS

| | | |
|---|---|---|
| 6,152,668 A | 11/2000 | Knoch |
| 6,156,688 A | 12/2000 | Ando et al. |
| 6,173,679 B1 | 1/2001 | Bruckner et al. |
| 6,187,148 B1 | 2/2001 | Sturgulewski |
| 6,189,819 B1 | 2/2001 | Racine |
| 6,290,494 B1 | 9/2001 | Barkdoll |
| 6,412,221 B1 | 7/2002 | Emsbo |
| 6,424,457 B1 | 7/2002 | Koonmen et al. |
| 6,495,268 B1 | 12/2002 | Harth, III et al. |
| 6,539,602 B1 | 4/2003 | Ozawa et al. |
| 6,596,128 B2 | 7/2003 | Westbrook |
| 6,626,984 B1 | 9/2003 | Taylor |
| 6,699,035 B2 | 3/2004 | Brooker |
| 6,712,576 B2 | 3/2004 | Skarzenski et al. |
| 6,758,875 B2 | 7/2004 | Reid et al. |
| 6,786,941 B2 | 9/2004 | Reeves et al. |
| 6,830,660 B1 | 12/2004 | Yamauchi et al. |
| 6,907,895 B2 | 6/2005 | Johnson et al. |
| 6,946,011 B2 | 9/2005 | Snyder |
| 6,964,236 B2 | 11/2005 | Schucker |
| 7,056,390 B2 | 6/2006 | Fratello |
| 7,077,892 B2 | 7/2006 | Lee |
| 7,314,060 B2 | 1/2008 | Chen et al. |
| 7,331,298 B2 | 2/2008 | Barkdoll et al. |
| 7,433,743 B2 | 10/2008 | Pistikopoulos et al. |
| 7,497,930 B2 | 3/2009 | Barkdoll et al. |
| 7,547,377 B2 | 6/2009 | Inamasu et al. |
| 7,611,609 B1 | 11/2009 | Valia et al. |
| 7,644,711 B2 | 1/2010 | Creel |
| 7,722,843 B1 | 5/2010 | Srinivasachar |
| 7,727,307 B2 | 6/2010 | Winkler |
| 7,785,447 B2 | 8/2010 | Eatough et al. |
| 7,803,627 B2 | 9/2010 | Hodges et al. |
| 7,823,401 B2 | 11/2010 | Takeuchi et al. |
| 7,827,689 B2 | 11/2010 | Crane |
| 7,998,316 B2 | 8/2011 | Barkdoll |
| 8,071,060 B2 | 12/2011 | Ukai et al. |
| 8,079,751 B2 | 12/2011 | Kapila et al. |
| 8,080,088 B1 | 12/2011 | Srinivasachar |
| 8,146,376 B1 | 4/2012 | Williams et al. |
| 8,152,970 B2 | 4/2012 | Barkdoll et al. |
| 8,172,930 B2 | 5/2012 | Barkdoll |
| 8,236,142 B2 | 8/2012 | Westbrook |
| 8,266,853 B2 | 9/2012 | Bloom et al. |
| 8,311,777 B2 | 11/2012 | Suguira et al. |
| 8,383,055 B2 | 2/2013 | Palmer |
| 8,398,935 B2 | 3/2013 | Howell et al. |
| 8,409,405 B2 | 4/2013 | Kim et al. |
| 8,500,881 B2 | 8/2013 | Orita et al. |
| 8,515,508 B2 | 8/2013 | Kawamura et al. |
| 8,568,568 B2 | 10/2013 | Schuecker et al. |
| 8,640,635 B2 | 2/2014 | Bloom et al. |
| 8,647,476 B2 | 2/2014 | Kim et al. |
| 8,800,795 B2 | 8/2014 | Hwang |
| 8,956,995 B2 | 2/2015 | Masatsugu et al. |
| 8,980,063 B2 | 3/2015 | Kim et al. |
| 9,039,869 B2 | 5/2015 | Kim et al. |
| 9,057,023 B2 | 6/2015 | Reichelt et al. |
| 9,103,234 B2 | 8/2015 | Gu et al. |
| 9,169,439 B2 | 10/2015 | Sarpen et al. |
| 9,193,913 B2 | 11/2015 | Quanci et al. |
| 9,193,915 B2 | 11/2015 | West et al. |
| 9,200,225 B2 | 12/2015 | Barkdoll et al. |
| 9,238,778 B2 | 1/2016 | Quanci et al. |
| 9,243,186 B2 | 1/2016 | Quanci et al. |
| 9,249,357 B2 | 2/2016 | Quanci et al. |
| 9,273,249 B2 | 3/2016 | Quanci et al. |
| 9,273,250 B2 | 3/2016 | Choi et al. |
| 9,321,965 B2 | 4/2016 | Barkdoll |
| 9,359,554 B2 | 6/2016 | Quanci et al. |
| 9,404,043 B2 | 8/2016 | Kim |
| 9,463,980 B2 | 10/2016 | Fukada et al. |
| 9,476,547 B2 | 10/2016 | Quanci et al. |
| 9,498,786 B2 | 11/2016 | Pearson |
| 9,580,656 B2 | 2/2017 | Quanci et al. |
| 9,672,499 B2 | 6/2017 | Quanci et al. |
| 9,683,740 B2 | 6/2017 | Rodgers et al. |
| 9,708,542 B2 | 7/2017 | Quanci et al. |
| 9,862,888 B2 | 1/2018 | Quanci et al. |
| 9,976,089 B2 | 5/2018 | Quanci et al. |
| 10,016,714 B2 | 7/2018 | Quanci et al. |
| 10,041,002 B2 | 8/2018 | Quanci et al. |
| 10,047,295 B2 | 8/2018 | Chun et al. |
| 10,047,296 B2 | 8/2018 | Chun et al. |
| 10,053,627 B2 | 8/2018 | Sarpen et al. |
| 10,233,392 B2 | 3/2019 | Quanci et al. |
| 10,308,876 B2 | 6/2019 | Quanci et al. |
| 10,323,192 B2 | 6/2019 | Quanci et al. |
| 10,392,563 B2 | 8/2019 | Kim et al. |
| 10,435,042 B1 | 10/2019 | Weymouth |
| 10,526,541 B2 | 1/2020 | West et al. |
| 10,526,542 B2 | 1/2020 | Quanci et al. |
| 10,578,521 B1 | 3/2020 | Dinakaran et al. |
| 10,611,965 B2 | 4/2020 | Quanci et al. |
| 10,619,101 B2 | 4/2020 | Quanci et al. |
| 10,732,621 B2 | 8/2020 | Cella et al. |
| 10,760,002 B2 | 9/2020 | Ball et al. |
| 10,851,306 B2 | 12/2020 | Crum et al. |
| 10,877,007 B2 | 12/2020 | Steele et al. |
| 10,883,051 B2 | 1/2021 | Quanci et al. |
| 10,920,148 B2 | 2/2021 | Quanci et al. |
| 10,927,303 B2 | 2/2021 | Choi et al. |
| 10,947,455 B2 | 3/2021 | Quanci et al. |
| 10,968,393 B2 | 4/2021 | West et al. |
| 10,968,395 B2 | 4/2021 | Quanci et al. |
| 10,975,309 B2 | 4/2021 | Quanci et al. |
| 10,975,310 B2 | 4/2021 | Quanci et al. |
| 10,975,311 B2 | 4/2021 | Quanci et al. |
| 11,008,517 B2 | 5/2021 | Chun et al. |
| 11,008,518 B2 | 5/2021 | Quanci et al. |
| 11,021,655 B2 | 6/2021 | Quanci et al. |
| 11,053,444 B2 | 7/2021 | Quanci et al. |
| 11,060,032 B2 | 7/2021 | Quanci et al. |
| 11,071,935 B2 | 7/2021 | Quanci et al. |
| 11,098,252 B2 | 8/2021 | Quanci et al. |
| 11,117,087 B2 | 9/2021 | Quanci |
| 11,142,699 B2 | 10/2021 | West et al. |
| 11,186,778 B2 | 11/2021 | Crum et al. |
| 11,193,069 B2 | 12/2021 | Quanci et al. |
| 11,214,739 B2 | 1/2022 | Quanci et al. |
| 11,261,381 B2 | 3/2022 | Quanci et al. |
| 11,359,145 B2 | 6/2022 | Ball et al. |
| 11,359,146 B2 | 6/2022 | Quanci et al. |
| 11,365,355 B2 | 6/2022 | Quanci et al. |
| 11,395,989 B2 | 7/2022 | Quanci et al. |
| 11,441,077 B2 | 9/2022 | Quanci et al. |
| 11,441,078 B2 | 9/2022 | Quanci et al. |
| 11,486,572 B2 | 11/2022 | Quanci et al. |
| 11,505,747 B2 | 11/2022 | Quanci et al. |
| 11,508,230 B2 | 11/2022 | Quanci et al. |
| 11,597,881 B2 | 3/2023 | Quanci et al. |
| 11,643,602 B2 | 5/2023 | Quanci et al. |
| 11,680,208 B2 | 6/2023 | Quanci et al. |
| 11,692,138 B2 | 7/2023 | Quanci et al. |
| 11,746,296 B2 | 9/2023 | Choi et al. |
| 11,760,937 B2 | 9/2023 | Quanci et al. |
| 11,767,482 B2 | 9/2023 | Quanci et al. |
| 11,788,012 B2 | 10/2023 | Quanci et al. |
| 11,795,400 B2 | 10/2023 | West et al. |
| 11,807,812 B2 | 11/2023 | Quanci et al. |
| 11,819,802 B2 | 11/2023 | Quanci et al. |
| 11,845,037 B2 | 12/2023 | Quanci et al. |
| 11,845,897 B2 | 12/2023 | Quanci et al. |
| 11,845,898 B2 | 12/2023 | Crum et al. |
| 11,851,724 B2 | 12/2023 | Quanci et al. |
| 2002/0170605 A1 | 11/2002 | Shiraishi et al. |
| 2003/0014954 A1 | 1/2003 | Ronning et al. |
| 2003/0015809 A1 | 1/2003 | Carson |
| 2003/0057083 A1 | 3/2003 | Eatough et al. |
| 2004/0016377 A1 | 1/2004 | Johnson et al. |
| 2004/0220840 A1 | 11/2004 | Bonissone et al. |
| 2005/0087767 A1 | 4/2005 | Fitzgerald et al. |
| 2005/0096759 A1 | 5/2005 | Benjamin et al. |
| 2006/0029532 A1 | 2/2006 | Breen et al. |

(56) References Cited

U.S. PATENT DOCUMENTS

| | | |
|---|---|---|
| 2006/0102420 A1 | 5/2006 | Huber et al. |
| 2006/0149407 A1 | 7/2006 | Markham et al. |
| 2007/0087946 A1 | 4/2007 | Quest et al. |
| 2007/0102278 A1 | 5/2007 | Inamasu et al. |
| 2007/0116619 A1 | 5/2007 | Taylor et al. |
| 2007/0251198 A1 | 11/2007 | Witter |
| 2008/0028935 A1 | 2/2008 | Andersson |
| 2008/0116052 A1 | 5/2008 | Eatough et al. |
| 2008/0179165 A1 | 7/2008 | Chen et al. |
| 2008/0250863 A1 | 10/2008 | Moore |
| 2008/0257236 A1 | 10/2008 | Green |
| 2008/0271985 A1 | 11/2008 | Yamasaki |
| 2008/0289305 A1 | 11/2008 | Girondi |
| 2009/0007785 A1 | 1/2009 | Kimura et al. |
| 2009/0032385 A1 | 2/2009 | Engle |
| 2009/0105852 A1 | 4/2009 | Wintrich et al. |
| 2009/0152092 A1 | 6/2009 | Kim et al. |
| 2009/0162269 A1 | 6/2009 | Barger et al. |
| 2009/0217576 A1 | 9/2009 | Kim et al. |
| 2009/0257932 A1 | 10/2009 | Canari et al. |
| 2009/0283395 A1 | 11/2009 | Hippe |
| 2010/0015564 A1 | 1/2010 | Chun et al. |
| 2010/0095521 A1 | 4/2010 | Kartal et al. |
| 2010/0106310 A1 | 4/2010 | Grohman |
| 2010/0113266 A1 | 5/2010 | Abe et al. |
| 2010/0115912 A1 | 5/2010 | Worley |
| 2010/0119425 A1 | 5/2010 | Palmer |
| 2010/0181297 A1 | 7/2010 | Whysail |
| 2010/0196597 A1 | 8/2010 | Di Loreto |
| 2010/0276269 A1 | 11/2010 | Schuecker et al. |
| 2010/0287871 A1 | 11/2010 | Bloom et al. |
| 2010/0300867 A1 | 12/2010 | Kim et al. |
| 2010/0314234 A1 | 12/2010 | Knoch et al. |
| 2011/0000284 A1 | 1/2011 | Kumar et al. |
| 2011/0014406 A1 | 1/2011 | Coleman et al. |
| 2011/0048917 A1 | 3/2011 | Kim et al. |
| 2011/0083314 A1 | 4/2011 | Baird |
| 2011/0088600 A1 | 4/2011 | McRae |
| 2011/0100273 A1 | 5/2011 | Ptacek |
| 2011/0120852 A1 | 5/2011 | Kim |
| 2011/0144406 A1 | 6/2011 | Masatsugu et al. |
| 2011/0156902 A1 | 6/2011 | Wang et al. |
| 2011/0168482 A1 | 7/2011 | Merchant et al. |
| 2011/0174301 A1 | 7/2011 | Haydock et al. |
| 2011/0192395 A1 | 8/2011 | Kim |
| 2011/0198206 A1* | 8/2011 | Kim .................... C10B 5/06 201/1 |
| 2011/0223088 A1 | 9/2011 | Chang et al. |
| 2011/0253521 A1 | 10/2011 | Kim |
| 2011/0291827 A1 | 12/2011 | Baldocchi et al. |
| 2011/0313218 A1 | 12/2011 | Dana |
| 2011/0315538 A1 | 12/2011 | Kim et al. |
| 2012/0031076 A1 | 2/2012 | Frank et al. |
| 2012/0125709 A1 | 5/2012 | Merchant et al. |
| 2012/0152720 A1 | 6/2012 | Reichelt et al. |
| 2012/0177541 A1 | 7/2012 | Mutsuda et al. |
| 2012/0179421 A1 | 7/2012 | Dasgupta |
| 2012/0180133 A1 | 7/2012 | Ai-Harbi et al. |
| 2012/0195815 A1 | 8/2012 | Moore et al. |
| 2012/0228115 A1 | 9/2012 | Westbrook |
| 2012/0247939 A1 | 10/2012 | Kim et al. |
| 2012/0285080 A1 | 11/2012 | Despen et al. |
| 2012/0305380 A1 | 12/2012 | Wang et al. |
| 2012/0312019 A1 | 12/2012 | Rechtman |
| 2013/0020781 A1 | 1/2013 | Kishikawa |
| 2013/0045149 A1 | 2/2013 | Miller |
| 2013/0213114 A1 | 8/2013 | Wetzig et al. |
| 2013/0216717 A1 | 8/2013 | Rago et al. |
| 2013/0220373 A1 | 8/2013 | Kim |
| 2013/0306462 A1 | 11/2013 | Kim et al. |
| 2014/0039833 A1 | 2/2014 | Sharpe, Jr. et al. |
| 2014/0048402 A1 | 2/2014 | Quanci et al. |
| 2014/0083836 A1* | 3/2014 | Quanci .................... C10B 41/08 201/37 |
| 2014/0156584 A1 | 6/2014 | Motukuri et al. |
| 2014/0208997 A1 | 7/2014 | Alferyev et al. |
| 2014/0224123 A1 | 8/2014 | Walters |
| 2015/0041304 A1 | 2/2015 | Kiim et al. |
| 2015/0075962 A1 | 3/2015 | Shimoyama et al. |
| 2015/0122629 A1 | 5/2015 | Freimuth et al. |
| 2015/0143908 A1 | 5/2015 | Cetinkaya |
| 2015/0175433 A1 | 6/2015 | Micka et al. |
| 2015/0176095 A1 | 6/2015 | Connors et al. |
| 2015/0219530 A1 | 8/2015 | Li et al. |
| 2015/0226499 A1 | 8/2015 | Mikkelsen |
| 2016/0026193 A1 | 1/2016 | Rhodes et al. |
| 2016/0048139 A1 | 2/2016 | Samples et al. |
| 2016/0060536 A1* | 3/2016 | Quanci .................... C10B 35/00 201/40 |
| 2016/0149944 A1 | 5/2016 | Obermeirer et al. |
| 2016/0154171 A1 | 6/2016 | Kato et al. |
| 2016/0186065 A1* | 6/2016 | Quanci .................... C10L 5/36 201/20 |
| 2016/0319198 A1* | 11/2016 | Quanci .................... C10B 15/02 |
| 2016/0370082 A1 | 12/2016 | Olivo |
| 2016/0377430 A1 | 12/2016 | Kalagnanam et al. |
| 2017/0173519 A1 | 6/2017 | Naito |
| 2017/0182447 A1 | 6/2017 | Sappok et al. |
| 2017/0226425 A1 | 8/2017 | Kim et al. |
| 2017/0261417 A1 | 9/2017 | Zhang |
| 2017/0313943 A1 | 11/2017 | Valdevies |
| 2019/0317167 A1 | 10/2019 | LaBorde et al. |
| 2020/0071190 A1 | 3/2020 | Wiederin et al. |
| 2020/0139273 A1 | 5/2020 | Badiei |
| 2020/0173679 A1 | 6/2020 | O'Reilly et al. |
| 2020/0208063 A1 | 7/2020 | Quanci |
| 2021/0198579 A1 | 7/2021 | Quanci et al. |
| 2021/0261877 A1 | 8/2021 | Despen et al. |
| 2021/0363427 A1 | 11/2021 | Quanci et al. |
| 2022/0056342 A1 | 2/2022 | Quanci et al. |
| 2022/0204858 A1 | 6/2022 | West et al. |
| 2022/0298423 A1 | 9/2022 | Quanci et al. |
| 2022/0356410 A1 | 11/2022 | Quanci et al. |
| 2023/0142380 A1 | 5/2023 | Quanci et al. |
| 2023/0258326 A1 | 8/2023 | Quanci et al. |
| 2023/0360511 A1 | 11/2023 | Quanci et al. |
| 2023/0416629 A1 | 12/2023 | Quanci et al. |
| 2024/0110103 A1 | 4/2024 | Quanci et al. |

FOREIGN PATENT DOCUMENTS

| | | |
|---|---|---|
| CA | 2822841 | 7/2012 |
| CA | 2822857 | 7/2012 |
| CA | 2905110 A1 | 9/2014 |
| CN | 87212113 U | 6/1988 |
| CN | 87107195 A | 7/1988 |
| CN | 2064363 U | 10/1990 |
| CN | 2139121 Y | 7/1993 |
| CN | 1092457 A | 9/1994 |
| CN | 1255528 A | 6/2000 |
| CN | 1270983 A | 10/2000 |
| CN | 2528771 Y | 2/2002 |
| CN | 1358822 A | 7/2002 |
| CN | 2521473 Y | 11/2002 |
| CN | 1468364 A | 1/2004 |
| CN | 1527872 A | 9/2004 |
| CN | 2668641 | 1/2005 |
| CN | 1957204 A | 5/2007 |
| CN | 101037603 A | 9/2007 |
| CN | 101058731 A | 10/2007 |
| CN | 101157874 A | 4/2008 |
| CN | 101211495 A | 7/2008 |
| CN | 201121178 Y | 9/2008 |
| CN | 101395248 A | 3/2009 |
| CN | 100510004 C | 7/2009 |
| CN | 101486017 A | 7/2009 |
| CN | 201264981 Y | 7/2009 |
| CN | 101497835 A | 8/2009 |
| CN | 101509427 A | 8/2009 |
| CN | 101886466 A | 11/2010 |
| CN | 101910530 A | 12/2010 |
| CN | 102072829 A | 5/2011 |
| CN | 102155300 A | 8/2011 |
| CN | 2509188 Y | 11/2011 |

(56) References Cited

FOREIGN PATENT DOCUMENTS

| | | |
|---|---|---|
| CN | 202226816 | 5/2012 |
| CN | 202265541 U | 6/2012 |
| CN | 102584294 A | 7/2012 |
| CN | 202415446 U | 9/2012 |
| CN | 202470353 U | 10/2012 |
| CN | 103399536 A | 11/2013 |
| CN | 103468289 A | 12/2013 |
| CN | 103756699 A | 4/2014 |
| CN | 103913193 A | 7/2014 |
| CN | 203981700 U | 12/2014 |
| CN | 104498059 A | 4/2015 |
| CN | 105001914 A | 10/2015 |
| CN | 105137947 A | 12/2015 |
| CN | 105189704 A | 12/2015 |
| CN | 105264448 A | 1/2016 |
| CN | 105467949 A | 4/2016 |
| CN | 106399607 A | 2/2017 |
| CN | 106661456 A | 5/2017 |
| CN | 106687564 A | 5/2017 |
| CN | 107022359 A | 8/2017 |
| CN | 107267183 A | 10/2017 |
| CN | 107445633 A | 12/2017 |
| CN | 108219807 A | 6/2018 |
| CN | 100500619 C | 6/2020 |
| CN | 111778048 A | 10/2020 |
| CN | 113322085 A | 8/2021 |
| CN | 113462415 A | 10/2021 |
| CN | 114517099 A | 5/2022 |
| CN | 101921643 B | 12/2022 |
| DE | 201729 C | 9/1908 |
| DE | 212176 | 7/1909 |
| DE | 1212037 B | 3/1966 |
| DE | 2212544 A | 1/1973 |
| DE | 2720688 A1 | 11/1978 |
| DE | 3231697 C1 | 1/1984 |
| DE | 3328702 A1 | 2/1984 |
| DE | 3315738 C2 | 3/1984 |
| DE | 3329367 C | 11/1984 |
| DE | 3407487 C1 | 6/1985 |
| DE | 19545736 | 6/1997 |
| DE | 19803455 | 8/1999 |
| DE | 10122531 A1 | 11/2002 |
| DE | 10154785 | 5/2003 |
| DE | 102004062936 A1 | 7/2006 |
| DE | 102005015301 | 10/2006 |
| DE | 102006004669 | 8/2007 |
| DE | 102006026521 | 12/2007 |
| DE | 102009031436 | 1/2011 |
| DE | 102011052785 | 12/2012 |
| EA | 010510 B1 | 10/2008 |
| EP | 0126399 A1 | 11/1984 |
| EP | 0208490 A1 | 1/1987 |
| EP | 0903393 A2 | 3/1999 |
| EP | 1538503 A1 | 6/2005 |
| EP | 1860034 A1 | 11/2007 |
| EP | 2295129 A1 | 3/2011 |
| EP | 2468837 A1 | 6/2012 |
| FR | 2339664 | 8/1977 |
| FR | 2517802 | 6/1983 |
| FR | 2764978 | 12/1998 |
| GB | 364236 A | 1/1932 |
| GB | 368649 A | 3/1932 |
| GB | 441784 | 1/1936 |
| GB | 606340 | 8/1948 |
| GB | 611524 | 11/1948 |
| GB | 725865 | 3/1955 |
| GB | 783720 A | 9/1957 |
| GB | 871094 | 6/1961 |
| GB | 923205 A | 5/1963 |
| GB | 2000193 A | 1/1979 |
| JP | S50148405 | 11/1975 |
| JP | S5319301 A | 2/1978 |
| JP | 54054101 | 4/1979 |
| JP | S5453103 A | 4/1979 |
| JP | 57051786 | 3/1982 |
| JP | 57051787 | 3/1982 |
| JP | 57083585 | 5/1982 |
| JP | 57090092 | 6/1982 |
| JP | S57172978 A | 10/1982 |
| JP | 58091788 | 5/1983 |
| JP | 59051978 | 3/1984 |
| JP | 59053589 | 3/1984 |
| JP | 59071388 | 4/1984 |
| JP | 59108083 | 6/1984 |
| JP | 59145281 | 8/1984 |
| JP | 60004588 | 1/1985 |
| JP | 61106690 | 5/1986 |
| JP | 62011794 | 1/1987 |
| JP | 62285980 | 12/1987 |
| JP | 01103694 | 4/1989 |
| JP | 01249886 | 10/1989 |
| JP | H0319127 | 3/1991 |
| JP | 03197588 | 8/1991 |
| JP | 04159392 | 6/1992 |
| JP | H04178494 A | 6/1992 |
| JP | H05230466 A | 9/1993 |
| JP | H0649450 A | 2/1994 |
| JP | H0654753 U | 7/1994 |
| JP | H06264062 | 9/1994 |
| JP | H06299156 A | 10/1994 |
| JP | H0776713 A | 3/1995 |
| JP | 07188668 | 7/1995 |
| JP | 07216357 | 8/1995 |
| JP | H07204432 | 8/1995 |
| JP | H0843314 A | 2/1996 |
| JP | H08104875 A | 4/1996 |
| JP | 08127778 | 5/1996 |
| JP | H08218071 A | 8/1996 |
| JP | H09310074 | 12/1997 |
| JP | H10273672 A | 10/1998 |
| JP | H11131074 | 5/1999 |
| JP | H11256166 A | 9/1999 |
| JP | 2000204373 A | 7/2000 |
| JP | 2000219883 A | 8/2000 |
| JP | 2001055576 A | 2/2001 |
| JP | 2001187887 A | 7/2001 |
| JP | 2001200258 | 7/2001 |
| JP | 2002097472 A | 4/2002 |
| JP | 2002106941 | 4/2002 |
| JP | 2003041258 | 2/2003 |
| JP | 2003051082 A | 2/2003 |
| JP | 2003071313 A | 3/2003 |
| JP | 2003292968 A | 10/2003 |
| JP | 2003342581 A | 12/2003 |
| JP | 2004169016 A | 6/2004 |
| JP | 2005503448 A | 2/2005 |
| JP | 2005135422 A | 5/2005 |
| JP | 2005154597 A | 6/2005 |
| JP | 2005263983 A | 9/2005 |
| JP | 2005344085 A | 12/2005 |
| JP | 2006188608 A | 7/2006 |
| JP | 2007063420 A | 3/2007 |
| JP | 3924064 B2 | 6/2007 |
| JP | 2007169484 A | 7/2007 |
| JP | 2007231326 A | 9/2007 |
| JP | 4101226 B2 | 6/2008 |
| JP | 2008231278 A | 10/2008 |
| JP | 2009019106 A | 1/2009 |
| JP | 2009073864 A | 4/2009 |
| JP | 2009073865 A | 4/2009 |
| JP | 2009135276 A | 6/2009 |
| JP | 2009144121 | 7/2009 |
| JP | 2009209286 A | 9/2009 |
| JP | 2010229239 A | 10/2010 |
| JP | 2010248389 A | 11/2010 |
| JP | 2011504947 A | 2/2011 |
| JP | 2011068733 A | 4/2011 |
| JP | 2011102351 A | 5/2011 |
| JP | 2012072389 A | 4/2012 |
| JP | 2012102302 | 5/2012 |
| JP | 2012102325 A | 5/2012 |

(56) References Cited

FOREIGN PATENT DOCUMENTS

| | | |
|---|---|---|
| JP | 2013006957 A | 1/2013 |
| JP | 2013510910 | 3/2013 |
| JP | 2013189322 A | 9/2013 |
| JP | 2014009284 A | 1/2014 |
| JP | 2014040502 A | 3/2014 |
| JP | 2015094091 A | 5/2015 |
| JP | 2015199791 A | 11/2015 |
| JP | 2016169897 A | 9/2016 |
| JP | 2020007472 A | 1/2020 |
| KR | 1019960008754 | 10/1996 |
| KR | 19990017156 U | 5/1999 |
| KR | 1019990054426 | 7/1999 |
| KR | 20000042375 A | 7/2000 |
| KR | 100296700 B1 | 10/2001 |
| KR | 20030012458 A | 2/2003 |
| KR | 1020040020883 A | 3/2004 |
| KR | 20040107204 A | 12/2004 |
| KR | 20050053861 A | 6/2005 |
| KR | 20060132336 A | 12/2006 |
| KR | 100737393 B1 | 7/2007 |
| KR | 100797852 | 1/2008 |
| KR | 20080069170 A | 7/2008 |
| KR | 20110010452 A | 2/2011 |
| KR | 101314288 | 4/2011 |
| KR | 20120033091 A | 4/2012 |
| KR | 20130050807 | 5/2013 |
| KR | 101318388 | 10/2013 |
| KR | 20140042526 A | 4/2014 |
| KR | 20140076155 A | 6/2014 |
| KR | 20150011084 A | 1/2015 |
| KR | 20150068557 A | 6/2015 |
| KR | 20170038102 A | 4/2017 |
| KR | 20170058808 A | 5/2017 |
| KR | 20170103857 A | 9/2017 |
| KR | 101862491 B1 | 5/2018 |
| RU | 2083532 C1 | 7/1997 |
| RU | 2441898 C2 | 2/2012 |
| RU | 2493233 C2 | 9/2013 |
| SU | 1535880 A1 | 1/1990 |
| TW | 201241166 A1 | 10/2012 |
| TW | 201245431 A1 | 11/2012 |
| UA | 50580 | 10/2002 |
| WO | WO9012074 | 10/1990 |
| WO | WO9945083 | 9/1999 |
| WO | WO02062922 | 8/2002 |
| WO | WO2003025093 | 3/2003 |
| WO | WO2005023649 | 3/2005 |
| WO | WO2005031297 | 4/2005 |
| WO | WO2005115583 | 12/2005 |
| WO | WO2007103649 | 9/2007 |
| WO | WO2008034424 | 3/2008 |
| WO | WO2008105269 | 9/2008 |
| WO | WO2009147983 | 12/2009 |
| WO | WO2010032734 | 3/2010 |
| WO | WO2010103992 | 9/2010 |
| WO | WO2011000447 | 1/2011 |
| WO | WO2011126043 | 10/2011 |
| WO | WO2012029979 | 3/2012 |
| WO | WO2012031726 | 3/2012 |
| WO | WO2013023872 | 2/2013 |
| WO | WO2010107513 | 9/2013 |
| WO | WO2013145679 | 10/2013 |
| WO | WO2013153557 | 10/2013 |
| WO | WO2014021909 | 2/2014 |
| WO | WO2014043667 | 3/2014 |
| WO | WO2014105064 | 7/2014 |
| WO | WO2014153050 | 9/2014 |
| WO | WO2016004106 | 1/2016 |
| WO | 2016033515 A1 | 3/2016 |
| WO | WO2016033511 | 3/2016 |
| WO | WO2016086322 | 6/2016 |
| WO | 2016109854 A1 | 7/2016 |
| WO | WO2022159604 | 7/2022 |
| WO | WO2022235839 | 11/2022 |

OTHER PUBLICATIONS

U.S. Appl. No. 18/313,647, filed May 8, 2023, Quanci et al.
U.S. Appl. No. 18/321,530, filed May 22, 2023, Quanci et al.
U.S. Appl. No. 18/363,465, filed Aug. 1, 2023, Quanci et al.
U.S. Appl. No. 18/363,508, filed Aug. 1, 2023, Choi et al.
U.S. Appl. No. 18/366,244, filed Aug. 7, 2023, Quanci et al.
U.S. Appl. No. 18/466,549, filed Sep. 13, 2023, Quanci et al.
U.S. Appl. No. 18/469,704, filed Sep. 19, 2023, Crum et al.
U.S. Appl. No. 18/473,135, filed Sep. 22, 2023, Quanci et al.
U.S. Appl. No. 18/473,143, filed Sep. 22, 2023, Quanci et al.
U.S. Appl. No. 18/483,019, filed Oct. 9, 2023, West et al.
U.S. Appl. No. 18/486,021, filed Oct. 12, 2023, Quanci et al.
U.S. Appl. No. 18/492,913, filed Oct. 24, 2023, Quanci et al.
U.S. Appl. No. 18/501,488, filed Nov. 3, 2023, Quanci et al.
U.S. Appl. No. 18/506,616, filed Nov. 10, 2023, Quanci et al.
U.S. Appl. No. 18/506,746, filed Nov. 10, 2023, Quanci et al.
U.S. Appl. No. 18/511,148, filed Nov. 16, 2023, Quanci et al.
U.S. Appl. No. 18/511,621, filed Nov. 16, 2023, Quanci et al.
"Asbestos", Virginia Department of Health, https://www.vdh.virginia.gov/environmental-health/public-health-toxicology/asbestos/, updated 2023, 2 pages.
ASTM D5341-99(2010)e1, Standard Test Method for Measuring Coke Reactivity Index (CRI) and Coke Strength After Reaction (CSR), ASTM International, West Conshohocken, PA, 2010.
Astrom, et al., "Feedback Systems: An Introduction for Scientists and Engineers," Sep. 16, 2006, available on line at http://people/duke.edu/-hpgavin/SystemID/References/Astrom-Feedback-2006.pdf ; 404 pages.
Basset et al., "Calculation of steady flow pressure loss coefficients for pipe junctions," Proc Instn Mech Engrs., vol. 215, Part C, p. 861-881 IMechIE 2001.
Beckman et al., "Possibilities and limits of cutting back coking plant output," Stahl Und Eisen, Verlag Stahleisen, Dusseldorf, DE, vol. 130, No. 8, Aug. 16, 2010, pp. 57-67.
Bloom, et al., "Modular cast block—The future of coke oven repairs," Iron & Steel Technol, AIST, Warrendale, PA, vol. 4, No. 3, Mar. 1, 2007, pp. 61-64.
Boyes, Walt. (2003), Instrumentation Reference Book (3rd Edition)—34.7.4.6 Infrared and Thermal Cameras, Elsevier. Online version available at: https://app.knovel.com/hotlink/pdf/id:kt004QMGV6/instrumentation-reference-2/ditigal-video.
"Ceramic fibers wool—to 1,300° C.", gTeek, Dec. 29, 2017 (date obtained from google search tools), https://www.gteek.com/ceramic-fibers-woolp-to1-300-%C2%B0C, 15 pages.
Chaudhari, K., Cupola Furnace, engineersgalary.com Jan. 24, 2016; 4 pages.
Clean coke process: process development studies by USS Engineers and Consultants, Inc., Wisconsin Tech Search, request date Oct. 5, 2011, 17 pages.
"Conveyor Chain Designer Guild", Mar. 27, 2014 (date obtained from wayback machine), Renold.com, Section 4, available online at: http://www.renold/com/upload/renoldswitzerland/conveyor_chain_-_designer_guide.pdf.
Costa, et al., "Edge Effects on the Flow Characteristics in a 90 deg Tee Junction," Transactions of the ASME, Nov. 2006, vol. 128, pp. 1204-1217.
Crelling, et al., "Effects of Weathered Coal on Coking Properties and Coke Quality", Fuel, 1979, vol. 58, Issue 7, pp. 542-546.
Database WPI, Week 199115, Thomson Scientific, Lond, GB; An 1991-107552.
De Cordova, et al. "Coke oven life prolongation—A multidisciplinary approach." 10.5151/2594-357X-2610 (2015) 12 pages.
Diez, et al., "Coal for Metallurgical Coke Production: Predictions of Coke Quality and Future Requirements for Cokemaking", International Journal of Coal Geology, 2002, vol. 50, Issue 1-4, pp. 389-412.
"High Alumina Cement-Manufacture, Characteristics and Uses," TheConstructor.org, https://theconstructor.org/concrete/high-alumina-cement/23686/; 12 pages.
"How Glass Is Made," Corning, https://www.corning.com/worldwide/en/innovation/materials-science/glass/how-glass-made.html, 2 pages.

(56) References Cited

OTHER PUBLICATIONS

Industrial Furnace Design Handbook, Editor-in-Chief: First Design Institute of First Ministry of Machinery Industry, Beijing: Mechanical Industry Press, pp. 180-183, Oct. 1981.
Ishiwata, et al. "Effect of coke diameter and oxygen concentration of blast on cupola operation." ISIJ International, 2011, vol. 51, pp. 1353-1359.
Ivanova, V. A. "Analysis of the requirements for foundry coke." IOP Conference Series: Materials Science and Engineering, 2020, vol. 986, pp. 1-6.
Joseph, B., "A tutorial on inferential control and its applications," Proceedings of the 1999 American Control Conference (Cat. No. 99CH36251), San Diego, CA, 1999, pp. 3106-3118 vol. 5.
Kerlin, Thomas (1999), Practical Thermocouple Thermometry—1.1 The Thermocouple. ISA. Online version available at https:app.knovel.com/pdf/id:kt007XPTM3/practical-thermocouple/the-thermocouple.
Kochanski et al., "Overview of Uhde Heat Recovery Cokemaking Technology," AISTech Iron and Steel Technology Conference Proceedings, Association for Iron and Steel Technology, U.S., vol. 1, Jan. 1, 2005, pp. 25-32.
Knoerzer et al. "Jewell-Thompson Non-Recovery Cokemaking", Steel Times, Fuel & Metallurgical Journals Ltd. London, GB, vol. 221, No. 4, Apr. 1, 1993, pp. 172-173,184.
Kusiorowski, et al., "Thermal decomposition of different types of abestos," Journal of Thermal Analysis and Calorimetry • Feb. 2012, 109, 693-704 (2012).
Lin, Rongying et al., "Study on the synergistic effect of calcium and aluminum on improving ash fusion temperature of semi-coke," International Journal of Coal Preparation and Utilization, May 31, 2019 (published online), vol. 42, No. 3, pp. 556-564.
Lipunov, et al. "Diagnostics of the Heating Systgem and Lining of Coke Ovens," Coke and Chemistry, 2014, Vopl. 57, No. 12, pp. 489-492.
Madias, et al., "A review on stamped charging of coals" (2013). Available at https://www.researchgate.net/publication/263887759_A_review_on_stamped_charging_of_coals.
Metallurgical Coke MSDS, ArcelorMittal, May 30, 2011, available online at http://dofasco.arcelormittal.com/-/media/Files/A/Arcelormittal-Canada/material-safety/metallurgical-coke.pdf.
"Middletown Coke Company HRSG Maintenance BACT Analysis Option 1—Individual Spray Quenches Sun Heat Recovery Coke Facility Process Flow Diagram Middletown Coke Company 100 Oven Case #1-24.5 VM", (Sep. 1, 2009), URL: http://web.archive.org/web/20090901042738/http://epa.ohio.gov/portals/27/transfer/ptiApplication/mcc/new/262504.pdf, (Feb. 12, 2016), XP055249803 [X] 1-13 *p. 7* *pp. 8-11*.
Pearson, D.E., "Influence of Geology on CSR (Coke Strength After Reaction with C02)," 2009, 8 pages.
Practical Technical Manual of Refractories, Baoyu Hu, etc., Beijing: Metallurgical Industry Press, Chapter 6; 2004, 6-30.
Powell, et al. "Cupola Furnaces", ASM International, downloaded from http://dl.asminternational.org/handbooks/edited-volume/chapter-pdf/501030/a0005197.pdf; 9 pages.
Refractories for Ironmaking and Steelmaking: A History of Battles over High Temperatures; Kyoshi Sugita (Japan, Shaolin Zhang), 1995, p. 160, 2004, 2-29.
"Refractory Castables," Victas.com, Dec. 28, 2011 (date obtained from WayBack Machine), https://www/vitcas.com/refactory-castables; 5 pages.
Rose, Harold J., "The Selection of Coals for the Manufacture of Coke," American Institute of Mining and Metallurgical Engineers, Feb. 1926, 8 pages.
Tiwari, et al., "A novel technique for assessing the coking potential of coals/cole blends for non-recovery coke making process," Fuel, vol. 107, May 2013, pp. 615-622.
Waddell, et al., "Heat-Recovery Cokemaking Presentation," Jan. 1999, pp. 1-25.
Walker, et al., "Sun Coke Company's heat recovery cokemaking technology high coke quality and low environmental impact",
Revue De Metallurgie—Cahiers D'Informations Techniques, Revue De Metallurgie. Paris, FR, (Mar. 1, 2003), vol. 100, No. 3, ISSN 0035-1563, p. 23.
Westbrook, "Heat-Recovery Cokemaking at Sun Coke," AISE Steel Technology, Pittsburg, PA, vol. 76, No. 1, Jan. 1999, pp. 25-28.
"What is dead-band control," forum post by user "wireaddict" on AllAboutCircuits.com message board, Feb. 8, 2007, accessed Oct. 24, 2018 at https:/forum.allaboutcircuits.com/threads/what-is-dead-band-control.4728/; 8 pages.
Yu et al., "Coke Oven Production Technology," Lianoning Science and Technology Press, first edition, Apr. 2014, pp. 356-358.
"Resources and Utilization of Coking Coal in China," Mingxin Shen ed., Chemical Industry Press, first edition, Jan. 2007, pp. 242-243, 247.
U.S. Appl. No. 18/584,320, filed Feb. 22, 2024, West et al.
U.S. Appl. No. 18/586,236, filed Feb. 23, 2024, Quanci et al.
Item HT 56107 Briquette, 'H' Type Household or Domestic Use, SECV Brown Coal Mine, Yallourn, Victoria, circa 1925, Museums Victoria Collections, https://collections.museumsvictoria.com.au/items/2286568, published on Mar. 2, 2021; 3 pages.
Office of the Federal Register, National Archives and Records Administration. (Apr. 14, 2005). 70 FR 19992—National Emission Standards for Coke Oven Batteries. [Government]. Office of the Federal Register, National Archives and Records Administration. https://www.govinfo.gov/app/details/FR-2005-04-15/05-6942.
International Search Report and Written Opinion issued by Korean International Search Authority for PCT/US2023/078709 on Mar. 4, 2024, 12 pages.
U.S. Appl. No. 13/730,598, filed Dec. 28, 2012, now U.S. Pat. No. 9,238,778, titled Systems and Methods for Improving Quenched Coke Recovery.
U.S. Appl. No. 14/952,267, filed Nov. 25, 2015, now U.S. Pat. No. 9,862,888, titled Systems and Methods for Improving Quenched Coke Recovery.
U.S. Appl. No. 15/830,320, filed Dec. 4, 2017, now U.S. Pat. No. 10,323,192, titled Systems and Methods for Improving Quenched Coke Recovery.
U.S. Appl. No. 13/730,735, filed Dec. 28, 2012, now U.S. Pat. No, 9,273,249, titled Systems and Methods for Controlling Air Distribution in a Coke Oven.
U.S. Appl. No. 14/655,013, filed Jun. 23, 2015, now U.S. Pat. No. 11,142,699, titled Vent Stack Lids and Associated Systems and Methods.
U.S. Appl. No. 17/471,491, filed Sep. 10, 2021, now U.S. Pat. No. 11,939,526 (Mar. 26, 2024), titled Vent Stack Lids and Associated Systems and Methods.
U.S. Appl. No. 18/584,320, filed Feb. 22, 2024, titled Vent Stack Lids and Associated Systems and Methods.
U.S. Appl. No. 13/843,166, filed Mar. 15, 2013, now U.S. Pat. No. 9,273,250, titled Methods and Systems for Improved Quench Tower Design.
U.S. Appl. No. 15/014,547, filed Feb. 3, 2016, now, U.S. Pat. No. 10,927,303, titled Methods for Improved Quench Tower Design.
U.S. Appl. No. 17/155,818, filed Jan. 22, 2021, now U.S. Pat. No. 11,746,296, titled Methods and Systems for Improved Quench Tower Design.
U.S. Appl. No. 14/655,003, filed Jun. 23, 2015, now U.S. Pat. No. 10,760,002, titled Systems and Methods for Maintaining a Hot Car in a Coke Plant.
U.S. Appl. No. 16/897,957, filed Jun. 10, 2020, now U.S. Pat. No. 11,359,145, titled Systems and Methods for Maintaining a Hot Car in a Coke Plant.
U.S. Appl. No. 13/829,588, filed Mar. 14, 2013, now U.S. Pat. No. 9,193,915, titled Horizontal Heat Recovery Coke Ovens Having Monolith Crowns.
U.S. Appl. No. 15/322,176, filed Dec. 27, 2016, now U.S. Pat. No. 10,526,541, titled Horizontal Heat Recovery Coke Ovens Having Monolith Crowns.
U.S. Appl. No. 17/076,563, filed Oct. 21, 2020, now U.S. Pat. No. 11,186,778, titled System and Method for Repairing a Coke Oven.
U.S. Appl. No. 17/521,061, now U.S. Pat. No. 11,845,898, filed on Nov. 8, 2021, titled System and Method for Repairing a Coke Oven.

(56) References Cited

OTHER PUBLICATIONS

U.S. Appl. No. 18/469,704, filed Sep. 19, 2023, titled System and Method for Repairing a Coke Oven.
U.S. Appl. No. 17/135,483, filed Dec. 28, 2020, titled Oven Health Optimization Systems and Methods.
U.S. Appl. No. 16/729,053, filed Dec. 27, 2019, now U.S. Pat. No. 11,760,937, titled Oven Uptakes.
U.S. Appl. No. 16/729,036, filed Dec. 27, 2019, now U.S. Pat. No. 11,365,355, titled Systems and Methods for Treating a Surface of a Coke Plant.
U.S. Appl. No. 17/747,708, filed May 18, 2022, titled Systems and Methods for Treating a Surface of a Coke Plant.
U.S. Appl. No. 16/729,201, filed Dec. 27, 2019, titled Gaseous Tracer Leak Detection.
U.S. Appl. No. 16/729,122, filed Dec. 27, 2019, now U.S. Pat. No. 11,395,989, titled Methods and Systems for Providing Corrosion Resistant Surfaces in Contaminant Treatment Systems.
U.S. Appl. No. 17/843,164, filed Jun. 17, 2022, now U.S. Pat. No. 11,819,802, titled Methods and Systems for Providing Corrosion Resistant Surfaces in Contaminant Treatment Systems.
U.S. Appl. No. 18/486,021, filed Oct. 12, 2023, titled Methods and Systems for Providing Corrosion Resistant Surfaces in Contaminant Treatment Systems.
U.S. Appl. No. 16/729,068, filed Dec. 27, 2019, now U.S. Pat. No. 11,486,572, titled Systems and Methods for Utilizing Flue Gas.
U.S. Appl. No. 17/947,520, filed Sep. 19, 2022, titled Systems and Methods for Utilizing Flue Gas.
U.S. Appl. No. 16/729,129, filed Dec. 27, 2019, now U.S. Pat. No. 11,008,518, titled Coke Plant Tunnel Repair and Flexible Joints.
U.S. Appl. No. 17/320,343, filed May 14, 2021, now U.S. Pat. No. 11,597,881, titled Coke Plant Tunnel Repair and Flexible Joints.
U.S. Appl. No. 18/168,142, filed Feb. 13, 2023, titled Coke Plant Tunnel Repair and Flexible Joints.
U.S. Appl. No. 16/729,170, now U.S. Pat. No. 11,193,069, filed Dec. 27, 2019, titled Coke Plant Tunnel Repair and Anchor Distribution.
U.S. Appl. No. 17/532,058, now U.S. Pat. No. 11,505,747, filed Nov. 22, 2021, titled Coke Plant Tunnel Repair and Anchor Distribution.
U.S. Appl. No. 17/967,615, filed Oct. 17, 2022, titled Coke Plant Tunnel Repair and Anchor Distribution.
U.S. Appl. No. 16/729,157, filed Dec. 27, 2019, now U.S. Pat. No. 11,071,935, titled Particulate Detection for Industrial Facilities, and Associated Systems and Methods.
U.S. Appl. No. 16/729,057, filed Dec. 27, 2019, now U.S. Pat. No. 11,021,655, titled Decarbonization of Coke Ovens and Associated Systems and Methods.
U.S. Appl. No. 17/321,857, filed May 17, 2021, now U.S. Pat. No. 11,643,602, titled Decarbonization of Coke Ovens and Associated Systems and Methods.
U.S. Appl. No. 18/313,622, filed May 8, 2023, titled Decarbonization of Coke Ovens and Associated Systems and Methods.
U.S. Appl. No. 16/729,212, filed Dec. 27, 2019, now U.S. Pat. No. 11,261,381, titled Heat Recovery Oven Foundation.
U.S. Appl. No. 17/584,672, now U.S. Pat. No. 11,845,897, filed Jan. 26, 2022, titled Heat Recovery Oven Foundation.
U.S. Appl. No. 18/492,913, filed Oct. 24, 2023, titled Heat Recovery Oven Foundation.
U.S. Appl. No. 16/729,219, now U.S. Pat. No. 11,098,252, filed Dec. 27, 2019, titled Spring-Loaded Heat Recovery Oven System and Method.
U.S. Appl. No. 17/388,874, filed Jul. 29, 2021, now, U.S. Pat. No. 11,680,208, titled Spring-Loaded Heat Recovery Oven System and Method.
U.S. Appl. No. 17/736,960, filed May 20, 2022, titled Foundry Coke Products, and Associated Systems and Methods.
U.S. Appl. No. 17/306,895, now U.S. Pat. No. 11,767,482, filed on May 3, 2021, now U.S. Pat. No. 11,767,482, titled High-Quality Coke Products.
U.S. Appl. No. 18/363,465, filed Aug. 1, 2023, titled High-Quality Coke Products.
U.S. Appl. No. 18/466,549, filed Sep. 13, 2023, titled High-Quality Coke Products.
U.S. Appl. No. 18/501,488, filed Nov. 3, 2023, titled Coal Blends, Foundry Coke Products, and Associated Systems, Devices, and Methods.
U.S. Appl. No. 18/052,739, filed Nov. 4, 2022, now U.S. Pat. No. 11,946,108, titled Foundry Coke Products and Associated Processing Methods Via Cupolas.
U.S. Appl. No. 18/586,236, filed Feb. 23, 2024, titled Foundry Coke Products and Associated Processing Methods Via Cupolas.
U.S. Appl. No. 18/052,760, filed Nov. 2, 2022, now U.S. Pat. No. 11,851,724, titled Foundry Coke Products, and Associated Systems, Devices, and Methods.
U.S. Appl. No. 18/506,746, filed Nov. 10, 2023, titled Foundry Coke Products, and Associated Systems, Devices, and Methods.
U.S. Appl. No. 18/511,148, filed Nov. 16, 2023, titled Products Comprising Char and Carbon, and Associated Systems, Devices, and Methods.
U.S. Appl. No. 18/511,621, filed Nov. 16, 2023, titled Pelletized Products and Associated Systems, Devices, and Methods.
U.S. Appl. No. 07/587,742, filed Sep. 25, 1990, now U.S. Pat. No. 5,114,542, titled Nonrecovery Coke Oven Battery and Method of Operation.
U.S. Appl. No. 07/878,904, filed May 6, 1992, now U.S. Pat. No. 5,318,671, titled Method of Operation of Nonrecovery Coke Oven Battery.
U.S. Appl. No. 09/783,195, filed Feb. 14, 2001, now U.S. Pat. No. 6,596,128, titled Coke Oven Flue Gas Sharing.
U.S. Appl. No. 07/886,804, filed May 22, 1992, now U.S. Pat. No. 5,228,955, titled High Strength Coke Oven Wall Having Gas Flues Therein.
U.S. Appl. No. 08/059,673, filed May 12, 1993, now U.S. Pat. No. 5,447,606, titled Method of and Apparatus for Capturing Coke Oven Charging Emissions.
U.S. Appl. No. 08/914,140, filed Aug. 19, 1997, now U.S. Pat. No. 5,928,476, titled Nonrecovery Coke Oven Door.
U.S. Appl. No. 09/680,187, filed Oct. 5, 2000, now U.S. Pat. No. 6,290,494, titled Method and Apparatus for Coal Coking.
U.S. Appl. No. 10/933,866, filed Sep. 3, 2004, now U.S. Pat. No. 7,331,298, titled Coke Oven Rotary Wedge Door Latch.
U.S. Appl. No. 11/424,566, filed Jun. 16, 2006, now U.S. Pat. No. 7,497,930, titled Method and Apparatus for Compacting Coal for a Coal Coking Process.
U.S. Appl. No. 12/405,269, filed Mar. 17, 2009, now U.S. Pat. No. 7,998,316, titled Flat Push Coke Wet Quenching Apparatus and Process.
U.S. Appl. No. 13/205,960, filed Aug. 9, 2011, now U.S. Pat. No. 9,321,965, titled Flat Push Coke Wet Quenching Apparatus and Process.
U.S. Appl. No. 11/367,236, filed Mar. 3, 2006, now U.S. Pat. No. 8,152,970, titled Method and Apparatus for Producing Coke.
U.S. Appl. No. 12/403,391, filed Mar. 13, 2009, now U.S. Pat. No. 8,172,930, titled Cleanable in Situ Spark Arrestor.
U.S. Appl. No. 12/849,192, filed Aug. 3, 2010, now U.S. Pat. No. 9,200,225, titled Method and Apparatus for Compacting Coal for a Coal Coking Process.
U.S. Appl. No. 13/631,215, filed Sep. 28, 2012, now U.S. Pat. No. 9,683,740, titled Methods for Handling Coal Processing Emissions and Associated Systems and Devices.
U.S. Appl. No. 13/730,692, filed Dec. 28, 2012, now U.S. Pat. No. 9,193,913, titled Reduced Output Rate Coke Oven Operation With Gas Sharing Providing Extended Process Cycle.
U.S. Appl. No. 14/655,204, now U.S. Pat. No. 10,016,714, filed Jun. 24, 2015, titled Systems and Methods for Removing Mercury From Emissions.
U.S. Appl. No. 16/000,516, now U.S. Pat. No. 11,117,087, filed Jun. 5, 2018, titled Systems and Methods for Removing Mercury From Emissions.
U.S. Appl. No. 17/459,380, now, U.S. Pat. No. 11,845,037, filed Jun. 5, 2018, titled Systems and Methods for Removing Mercury From Emissions.

(56) References Cited

OTHER PUBLICATIONS

U.S. Appl. No. 18/506,616, filed Nov. 10, 2023, titled Systems and Methods for Removing Mercury From Emissions.
U.S. Appl. No. 13/830,971, filed Mar. 14, 2013, now U.S. Pat. No. 10,047,296, titled Non-Perpendicular Connections Between Coke Oven Uptakes and a Hot Common Tunnel, and Associated Systems and Methods, now U.S. Pat. No. 10,047,295.
U.S. Appl. No. 16/026,363, filed Jul. 3, 2018, now U.S. Pat. No. 11,008,517, titled Non-Perpendicular Connections Between Coke Oven Uptakes and a Hot Common Tunnel, and Associated Systems and Methods.
U.S. Appl. No. 13/730,796, filed Dec. 28, 2012, now U.S. Pat. No. 10,883,051, titled Methods and Systems for Improved Coke Quenching.
U.S. Appl. No. 17/140,564, filed Jan. 4, 2021, now U.S. Pat. No. 11,807,812, titled Methods and Systems for Improved Coke Quenching.
U.S. Appl. No. 18/473,143, filed Sep. 22, 2023, titled Methods and Systems for Improved Coke Quenching.
U.S. Appl. No. 17/471,491, filed Sep. 10, 2021, now U.S. Pat. No. 11,142,699, titled Vent Stack Lids and Associated Systems and Methods.
U.S. Appl. No. 18/363,508, filed Aug. 1, 2023, titled Methods and Systems for Improved Quench Tower Design.
U.S. Appl. No. 15/511,036, filed Mar. 14, 2017, now U.S. Pat. No. 10,968,383, titled Coke Ovens Having Monolith Component Construction.
U.S. Appl. No. 17/190,720, now U.S. Pat. No. 11,795,400, filed Mar. 3, 2021, titled Coke Ovens Having Monolith Component Construction.
U.S. Appl. No. 18/483,019, filed Oct. 9, 2023, titled Coke Ovens Having Monolith Component Construction.
U.S. Appl. No. 13/589,009, filed Aug. 17, 2012, now U.S. Pat. No. 9,359,554, titled Automatic Draft Control System for Coke Plants.
U.S. Appl. No. 15/139,568, filed Apr. 27, 2016, now U.S. Pat. No. 10,947,455, titled Automatic Draft Control System for Coke Plants.
U.S. Appl. No. 17/176,391, now U.S. Pat. No. 11,692,138, filed Feb. 16, 2021, titled Automatic Draft Control System for Coke Plants.
U.S. Appl. No. 18/321,530, filed May 22, 2023, titled Automatic Draft Control System for Coke Plants.
U.S. Appl. No. 13/588,996, filed Aug. 17, 2012, now U.S. Pat. No. 9,243,186, titled Coke Plant Including Exhaust Gas Sharing.
U.S. Appl. No. 14/959,450, filed Dec. 4, 2015, now U.S. Pat. No. 10,041,002, titled Coke Plant Including Exhaust Gas Sharing.
U.S. Appl. No. 16/047,198, filed Jul. 27, 2018, now U.S. Pat. No. 10,611,965, titled Coke Plant Including Exhaust Gas Sharing.
U.S. Appl. No. 16/828,448, filed Mar. 24, 2020, now U.S. Pat. No. 11,441,077, titled Coke Plant Including Exhaust Gas Sharing.
U.S. Appl. No. 13/589,004, filed Aug. 17, 2012, now U.S. Pat. No. 9,249,357, titled Method and Apparatus for Volatile Matter Sharing in Stamp-Charged Coke Ovens.
U.S. Appl. No. 13/730,673, filed Dec. 28, 2012, now U.S. Pat. No. 9,476,547, titled Exhaust Flow Modifier, Duct Intersection Incorporating the Same, and Methods Therefor.
U.S. Appl. No. 15/281,891, filed Sep. 30, 2016, now U.S. Pat. No. 10,975,309, titled Exhaust Flow Modifier, Duck Intersection Incorporating the Same, and Methods Therefor.
U.S. Appl. No. 17/191,119, filed Mar. 3, 3021, titled Exhaust Flow Modifier, Duck Intersection Incorporating the Same, and Methods Therefor.
U.S. Appl. No. 13/598,394, filed Aug. 29, 2012, now U.S. Pat. No. 9,169,439, titled Method and Apparatus for Testing Coal Coking Properties.
U.S. Appl. No. 14/865,581, filed Sep. 25, 2015, now U.S. Pat. No. 10,053,627, titled Method and Apparatus for Testing Coal Coking Properties, now U.S. Pat. No. 10,053,627.
U.S. Appl. No. 14/839,384, filed Aug. 28, 2015, now U.S. Pat. No. 9,580,656, titled Coke Oven Charging System.
U.S. Appl. No. 15/443,246, filed Feb. 27, 2017, now U.S. Pat. No. 9,976,089, titled Coke Oven Charging System.
U.S. Appl. No. 14/587,670, filed Dec. 31, 2014, now U.S. Pat. No. 10,619,101, titled Methods for Decarbonizing Coking Ovens, and Associated Systems and Devices.
U.S. Appl. No. 16/845,530, filed Apr. 10, 2020, now U.S. Pat. No. 11,359,146, titled Methods for Decarbonizing Coking Ovens, and Associated Systems and Devices.
U.S. Appl. No. 14/984,489, filed Dec. 30, 2015, now U.S. Pat. No. 10,975,310, titled Multi-Modal Beds of Coking Material.
U.S. Appl. No. 14/983,837, filed Dec. 30, 2015, now U.S. Pat. No. 10,968,395, titled Multi-Modal Beds of Coking Material.
U.S. Appl. No. 14/986,281, filed Dec. 31, 2015, now U.S. Pat. No. 10,975,311, titled Multi-Modal Beds of Coking Material.
U.S. Appl. No. 17/222,886, filed Apr. 12, 2021, titled Multi-Modal Beds of Coking Material.
U.S. Appl. No. 14/987,625, filed Jan. 4, 2016, now U.S. Pat. No. 11,060,032, titled Integrated Coke Plant Automation and Optimization Using Advanced Control and Optimization Techniques.
U.S. Appl. No. 17/172,476, filed Feb. 10, 2021, now U.S. Pat. No. 11,788,012, titled Integrated Coke Plant Automation and Optimization Using Advanced Control and Optimization Techniques.
U.S. Appl. No. 18/473,143, filed Sep. 22, 2023, titled Integrated Coke Plant Automation and Optimization Using Advanced Control and Optimization Techniques.
U.S. Appl. No. 14/839,493, filed Aug. 28, 2015, now U.S. Pat. No. 10,233,392, titled Method and System for Optimizing Coke Plant Operation and Output.
U.S. Appl. No. 16/251,352, filed Jan. 18, 2019, now U.S. Pat. No. 11,053,444, titled Method and System for Optimizing Coke Plant Operation and Output.
U.S. Appl. No. 14/839,551, filed Aug. 28, 2015, now U.S. Pat. No. 10,308,876, titled Burn Profiles for Coke Operations.
U.S. Appl. No. 16/428,014, filed May 31, 2019, now U.S. Pat. No. 10,920,148, titled Improved Burn Profiles for Coke Operations.
U.S. Appl. No. 17/155,719, filed Jan. 22, 2021, now U.S. Pat. No. 11,441,078, titled Improved Burn Profiles for Coke Operations.
U.S. Appl. No. 14/839,588, filed Aug. 28, 2015, now U.S. Pat. No. 9,708,542, titled Method and System for Optimizing Coke Plant Operation and Output.
U.S. Appl. No. 15/392,942, filed Dec. 28, 2016, now U.S. Pat. No. 10,526,542, titled Method and System for Dynamically Charging a Coke Oven.
U.S. Appl. No. 16/735,103, filed Jan. 6, 2020, now U.S. Pat. No. 11,214,739, titled Method and System for Dynamically Charging a Coke Oven.
U.S. Appl. No. 15/614,525, filed Jun. 5, 2017, now U.S. Pat. No. 11,508,230, titled Methods and Systems for Automatically Generating a Remedial Action in an Industrial Facility.
U.S. Appl. No. 18/047,916, filed Oct. 19, 2022, titled Methods and Systems for Automatically Generating a Remedial Action in an Industrial Facility.
U.S. Appl. No. 15/987,860, filed May 23, 2018, now U.S. Pat. No. 10,851,306, titled System and Method for Repairing a Coke Oven.
U.S. Appl. No. 18/366,244, filed Aug. 7, 2023, titled Oven Uptakes.
U.S. Appl. No. 17/532,058, now U.S. Pat. No. 11,505,747, filed on Nov. 22, 2021, titled Coke Plant Tunnel Repair and Anchor Distribution.
U.S. Appl. No. 17/306,895, now U.S. Pat. No. 11,767,482, filed May 3, 2021, now U.S. Pat. No. 11,767,482, titled High-Quality Coke Products.
U.S. Appl. No. 18/052,739, filed Nov. 4, 2022, titled Foundry Coke Products and Associated Processing Methods Via Cupolas.
U.S. Appl. No. 18/770,274, filed Jul. 11, 2024, Quanci et al.
U.S. Appl. No. 18/793,631, filed Aug. 2, 2024, Quanci et al.
U.S. Appl. No. 18/892,228, filed Sep. 20, 2024, Quanci et al.
Schlueter, R. "What's so good about coke made from coal, Aug. 29, 2016," Belleview News-Democrat, Rschuleter@bnd.com; 4 pages.
Seal School, Coal v. Coke|Fast differences and Comparison. Viewable on YouTube (Year:2020).

* cited by examiner

| Breeze | T1 | T2 | T3 | T4 | T5 | T6 | T7 | T8 | T9 |
|---|---|---|---|---|---|---|---|---|---|
| V8 | 0 | 0 | 0 | 0 | 1.2 | 0 | 1.2 | 0.7 | 6.7 |
| V9 | 0 | 0 | 0 | 0 | 16.2 | 0 | 16.2 | 11.4 | 31.6 |
| V10 | 0 | 0 | 0 | 0 | 40.3 | 0.7 | 40.3 | 43.7 | 24.9 |
| V11 | 0 | 0 | 1.4 | 0 | 2.4 | 17.4 | 2.4 | 10.1 | 4 |
| V12 | 0 | 0.7 | 15.2 | 20.4 | 0 | 44.8 | 0 | 1.3 | 0 |
| V13 | 0 | 8.2 | 43.5 | 47.5 | 0 | 4 | 0 | 0 | 0 |
| V14 | 2.9 | 4.8 | 8.3 | 7.5 | 0 | 0 | 0 | 0 | 0 |
| V15 | 30.1 | 22.6 | 0.7 | 0 | 0 | 0 | 0 | 0 | 0 |
| V16 | 31.5 | 30.9 | 0 | 0 | 0 | 0 | 0 | 0 | 0 |
| V17 | 6.4 | 1.4 | 0 | 0 | 0 | 0 | 0 | 0 | 0 |
| V18 | 0.7 | 0 | 0 | 0 | 0 | 0 | 0 | 0 | 0 |

FIG. 3

| | Breeze | T1 | T2 | T3 | T4 | T5 | T6 | T7 | T8 | T9 |
|---|---|---|---|---|---|---|---|---|---|---|
| VM | 0.5 | 18.79 | 19.77 | 21.27 | 22.28 | 32.87 | 25.38 | 30.47 | 30.01 | 33.77 |
| Ash | 9.15 | 5.4 | 6.12 | 8.23 | 2.51 | 4.59 | 8.31 | 4.59 | 7.29 | 6.82 |
| sulfur | 0.68 | 0.73 | 0.85 | 0.75 | 0.55 | 0.7 | 0.69 | 0.7 | 0.78 | 0.96 |
| total inerts | 90 | 25.9 | 28.6 | 28.4 | 22.6 | 26.8 | 30.2 | 26.8 | 26.5 | 23.6 |
| F ddpm | 1 | 89 | 98 | 536 | 2612 | 30000 | 3390 | 30000 | 22000 | 30000 |
| log F | 0 | 1.95 | 1.99 | 2.73 | 3.42 | 4.48 | 3.53 | 4.48 | 4.34 | 4.48 |
| plastic range | 0 | 59 | 62 | 78 | 103 | 95 | 97 | 95 | 101 | 99 |
| ash fusion | 2526 | 2210 | 2700 | 2360 | 2426 | 2700 | 2670 | 2823 | 2630 | 2680 |
| model ash fusion (book) | 2535 | 2193 | 2663 | 2545 | 2607 | 2689 | 2596 | 2689 | 2566 | 2648 |
| model ash fusion (Other) | 2526 | 1866 | 2807 | 2543 | 2576 | 2823 | 2655 | 2823 | 2591 | 2766 |
| mineral matter | 3.6 | 3.1 | 3.8 | 4.9 | 1.5 | 2.6 | 4.9 | 2.6 | 4.5 | 3.7 |
| reflectance | 0 | 1.61 | 1.57 | 1.44 | 1.43 | 1.02 | 1.23 | 1.02 | 1.05 | 0.99 |
| CBI | 0 | 3.49 | 3.42 | 2.39 | 1.74 | 0.92 | 1.45 | 0.92 | 0.91 | 0.78 |
| RI | 0 | 7.17 | 6.93 | 6.64 | 6.71 | 3.92 | 4.76 | 3.92 | 4.01 | 3.76 |
| maxF Temp | 0 | 475 | 474 | 480 | 473 | 450 | 463 | 450 | 458 | 446 |
| softening Temp | 0 | 444 | 439 | 432 | 409 | 395 | 404 | 395 | 398 | 393 |
| solidfication Temp | 0 | 503 | 501 | 510 | 512 | 490 | 501 | 490 | 499 | 492 |
| dilatation% | 0 | 57 | 54 | 95 | 124 | 228 | 214 | 252 | 300 | 283 |

FIG. 4

|  | Breeze | T1 | T2 | T3 | T4 | T5 | T6 | T7 | T8 | T9 |
|---|---|---|---|---|---|---|---|---|---|---|
| Ash* | 9.15 | 5.40 | 6.12 | 8.23 | 2.51 | 4.59 | 8.31 | 4.59 | 7.29 | 6.82 |
| $SiO_2$ | 439.57 | 202.39 | 329.38 | 445.82 | 123.62 | 260.62 | 412.09 | 260.62 | 367.27 | 370.60 |
| $Al_2O_3$ | 251.63 | 118.26 | 176.93 | 194.80 | 72.46 | 127.10 | 242.65 | 127.10 | 201.50 | 189.87 |
| $Fe_2O_3$ | 109.43 | 62.86 | 41.55 | 59.59 | 32.25 | 25.15 | 59.67 | 25.15 | 59.71 | 56.13 |
| $TiO_2$ | 15.65 | 6.37 | 10.89 | 12.76 | 3.06 | 7.21 | 12.80 | 7.21 | 10.94 | 10.16 |
| CaO | 23.24 | 56.65 | 9.67 | 36.38 | 4.34 | 4.09 | 29.00 | 4.09 | 19.39 | 7.30 |
| MgO | 8.69 | 9.72 | 5.45 | 9.71 | 3.16 | 5.37 | 9.81 | 5.37 | 9.70 | 6.00 |
| $Na_2O$ | 5.49 | 3.19 | 4.41 | 2.14 | 3.89 | 4.73 | 3.07 | 4.73 | 4.59 | 6.27 |
| $K_2O$ | 17.20 | 7.51 | 9.06 | 12.92 | 3.66 | 11.70 | 14.71 | 11.70 | 14.07 | 14.05 |
| $P_2O_5$ | 2.47 | 0.43 | 1.47 | 0.49 | 0.25 | 0.41 | 5.98 | 0.41 | 2.77 | 1.50 |
| $SO_3$ | 3.57 | 56.70 | 9.06 | 31.44 | 2.99 | 4.64 | 20.36 | 4.64 | 17.64 | 6.14 |
| Undetermined | 38.06 | 15.93 | 14.14 | 16.95 | 1.31 | 7.99 | 20.86 | 7.99 | 21.43 | 13.98 |

*FIG. 5*

Coal Blend Properties

| | Sample Value | Estimated Minimum | Estimated Maximum |
|---|---|---|---|
| ash | 6.37 | 5.50 | 7.01 |
| SiO2 | 45.39 | 40.08 | 50.89 |
| Al2O3 | 25.52 | 22.15 | 29.11 |
| Fe2O3 | 9.97 | 8.56 | 11.25 |
| TiO2 | 1.46 | 1.25 | 1.66 |
| CaO | 5.62 | 4.90 | 6.20 |
| MgO | 1.37 | 1.23 | 1.51 |
| Na2O | 0.63 | 0.56 | 0.70 |
| K2O | 1.62 | 1.42 | 1.85 |
| P2O5 | 0.21 | 0.19 | 0.24 |
| SO3 | 5.18 | 4.48 | 5.87 |
| ash fusion (book) | 2,517 | 2,245 | 2,832 |
| ash fusion (model) | 2,326 | 1,993 | 2,578 |
| Reactivity (%) | 34.1% | 29.1% | 38.6% |
| Volatile Matter (VM) (%) | 19.0% | 17.0% | 25.0% |

*FIG. 6*

|  | Batch 1 | Batch 2 | Batch 3 | Batch 4 | Batch 4 (production |
|---|---|---|---|---|---|
| Total Ash (wt %) | 9.54 | 8.79 | 8.45 | 8.13 | 8.04 |
| Ash Fusion IDT (°F) | N/A | 2420 | 2370 | 2233 | 2150 |
| Ash Fusion ST (°F) | N/A | 2500 | 2510 | 2377 | 2370 |
| $Al_2O_3$ in Coal Blend Ash Composition (wt %) | 28.5 | 26.3 | 26.1 | 24.9 | 24.1 |
| $SiO_2$ in Coal Blend Ash Composition (wt %) | 49.4 | 48.9 | 48.8 | 49.1 | 46.0 |
| Ash Fusion (calculated by Formula (IA) or (IB)) | 2604 | 2544 | 2517 | 2494 | 2408 |
| CRI (wt %) | 30 | 36 | 32 | 36.5 | 35.5 |
| CSR (wt %) | 41 | 16 | 26 | 15.3 | 15.6 |

COAL BLENDS, FOUNDRY COKE PRODUCTS, AND ASSOCIATED SYSTEMS, DEVICES, AND METHODS

CROSS-REFERENCE TO RELATED APPLICATIONS

This application claims priority to U.S. Provisional Patent Application No. 63/382,446 filed Nov. 4, 2022, the disclosure of which is incorporated herein by reference in its entirety.

TECHNICAL FIELD

This disclosure relates to coal blends, foundry coke products, and associated systems, devices, and methods.

BACKGROUND

Coke can be divided into various subcategories. Foundry coke has a large size relative to blast coke and is of exceptional quality, including relatively low impurities, and relatively high carbon content, strength, and stability. Foundry coke is used in foundry cupolas to melt iron and produce cast iron and ductile iron products. However, the production cost, including the manufacturing cost, transportation cost, and environmental cost, for foundry coke is high. Therefore, there is a need in the art to improve the production process thereby to obtain high quality foundry coke at a higher yield or a lower cost.

Coke is a solid carbon fuel and carbon source produced from coal that is used in the production of steel. The coal can be obtained from a combination of different coal sources and often possess vastly different qualities and compositions. These resources can be used as fuel or feedstock for a diverse array of applications, such as steel production, cement production, and electricity generation. Furthermore, the diverse array of regulatory environments or economic incentives can further create additional requirements for the types of coal that a specific foundry, factory, or plant is permitted to use.

BRIEF DESCRIPTION OF THE DRAWINGS

Features, aspects, and advantages of the presently disclosed technology can be better understood with regard to the following drawings.

FIG. 3 is a table indicating volatile matter (VM) fractions for different types of coals usable in a coal blend, in accordance with one or more embodiments of the present technology.

FIG. 4 is a table indicating properties associated with different types of coals used in a coal blend, in accordance with one or more embodiments of the present technology.

FIG. 5 is a table indicating the composition associated with different types of coals used in a coal blend, in accordance with one or more embodiments of the present technology.

FIG. 6 is a table indicating additional measurements associated with different types of coals used in a coal blend, in accordance with one or more embodiments of the present technology.

Figure 1:
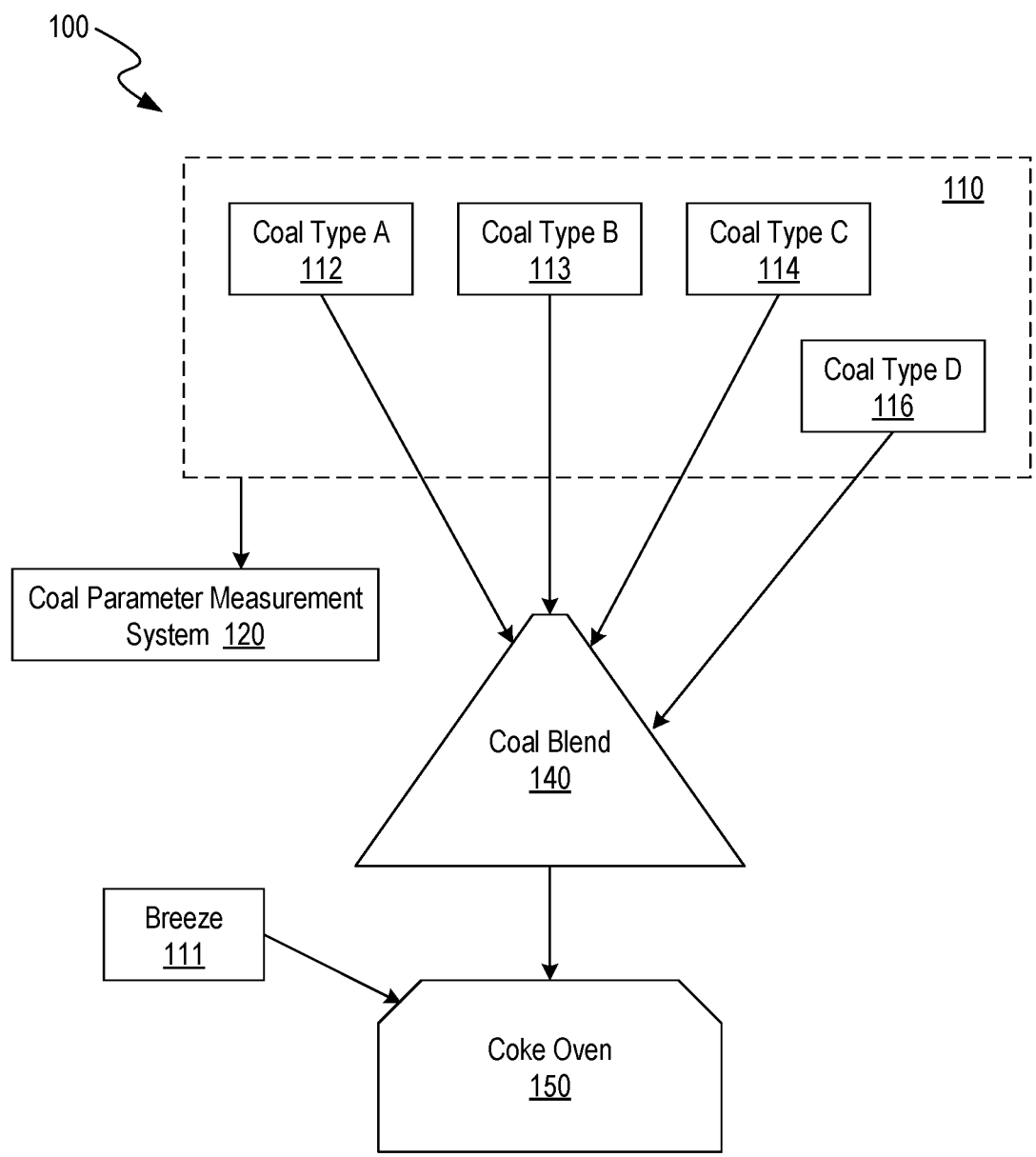
FIG. 1 shows an illustrative schematic system for obtaining coal parameters for multiple coal types and determining a coal blend formulation, in accordance with one or more embodiments of the present technology.

A person skilled in the relevant art will understand that the features shown in the drawings are for purposes of illustrations, and variations, including different or additional features and arrangements thereof, are possible.

DETAILED DESCRIPTION

I. Overview

Foundry coke is coke of a relatively large size, and of exceptional quality, such as very low content of impurities, and very high fixed carbon content, strength, and stability. Foundry coke is used in cupola furnaces to melt iron and recycled steel and as a carbon source to produce cast iron and ductile iron products. However, the production cost, including the manufacturing cost, transportation cost, and environmental cost, for foundry coke is high. Therefore, there is a need in the art to improve the production process thereby to obtain high quality foundry coke at a higher yield or a lower cost. Traditionally made coke typically has an ash fusion temperature (AFT) above 2650 degrees Fahrenheit (° F.). Due to this high temperature, the ash melts deeper in the cupola which reduces the available surface area for coke exposed to molten metal. As a result, less carbon is transferred to the iron.

The coke products disclosed herein for the present technology have an AFT lower than 2600° F. and therefore melt higher in the cupola, thereby increasing the amount of carbon surface exposed to the molten metal. Moreover, from a viscosity standpoint, a low AFT allows the melted ash to move through the carbon bed more quickly and results in a better phase separation in the well section of the cupola to allow more carbon and molten metal contact. As used herein, the term "molten metal" refers to molten iron, molten steel, or the final molten mixture of molten iron and molten steel.

An AFT can be obtained in various ways and can be separated into different types of AFTs. In some embodiments, an AFT can be measured from a sample of ash created by burning a coal, coal blend, or coke product to completion. The ash elemental analysis can be performed on each element, for example, individual silicon atoms create a signal in the analytical instrument. To obtain a mass percentage value used for model ash fusion calculation, some embodiments of the present technology can treat all elements as fully oxidized and determine a mass percentage is based oxidized forms. For example, some embodiments of the present technology can determine the $SiO_2$ mass but not the Si mass. In some embodiments, the mass percentages of $SiO_2$, $Al_2O_3$, $FeO_3$, CaO, other compounds, etc., can be normalized to sum up to 100%.

Alternatively or additionally, an AFT can be measured by an AFT test, such as a standard American Society for Testing and Materials (ASTM) method D1857. For example, some embodiments of the present technology can determine an initial deformation temperature (IDT), softening temperature (ST), hemispherical temperature (HT), and flow temperature (FT). These measured temperatures can have different values with respect to each other, and can be used to characterize a particular coal, coal blend, or coke product. Furthermore, as discussed elsewhere, the composition of the ash remaining from combustion of a coal or coal blend is considered to be the same as the ash remaining after combustion of a coke product produced from the coal or coal blend. Some embodiments can characterize a coal blend ash composition as the weighted average of the ash compositions of the coal components weighted by their respective mass fractions in the coal blend.

Further, traditional operation can also add $CaCO_3$-containing rocks to the charge to use as a flux to remove ash. The $CaCO_3$ penetrates into the ash to lower the AFT, or the ash itself dissolves into the $CaCO_3$ containing rocks. Given the very low surface to volume ratio for the fluxing to occur, this is an inefficient way to introduce a fluxing agent. Based on the unexpected discovery of the impact of a low AFT on the desired carbon transfer disclosed herein, the coke can be "pre-fluxed" by selecting coals or coal blends having ashes that are proportionally higher in the low melting oxides, such as CaO, MgO, $Fe_2O_3$, $Na_2O$, and $K_2O$, than in the high melting oxides of $Al_2O_3$ and $SiO_2$.

In a foundry cupola, coke is used as a fuel and carbon source to produce cast iron. Coke provides four functions in the cupola: (1) providing heat from the combustion to melt the iron or steel; (2) supplying carbon to the iron; (3) providing structural support for the iron or steel burden; and (4) creating gas permeable layers that allow the gases to travel upward and spread to provide good contact with the iron or steel.

Some embodiments can perform operations described in this disclosure to produce coke products that permit a higher carbon transfer rate to the iron or steel during foundry operations, which can result in better cupola performance. Some embodiments can use one of various types of ovens to produce coke products, such as a heat recovery oven, a non-recovery oven, a Thompson oven, another type of horizontal oven, a vertical byproduct oven, etc.

II. Coal Blends for Producing Foundry Coke Products, and Associated Systems and Methods Some embodiments of the present technology can perform operations to increase the efficiency of coke product production operations in a manner that can reduce energy consumption and increase yield. These operations can include determining the composition of coal blends used to produce a coke product, where the composition of a coal blend can include coals from different coal sources. Some embodiments can select specific coals for their VM content, where VM content and distribution can determine affect coke product yield, coke product properties, etc. Some embodiments can further perform specific processes when producing a coke product with a coke oven, where such processes can include opening or closing valves of a coke oven to maintain certain temperature relationships within sections of the coke oven. These outputs can result in coking products that are unique in comparison to other coking products with respect to reactivity, size, or other properties.

FIG. 1 shows an illustrative system 100 for obtaining coal parameters for multiple type of coals 112, 113, 114, 116 (collectively referred to as "coals 110") and determining a coal blend 140 formulation, in accordance with one or more embodiments. Various facilities and equipment can be used to blend the 110 coals from various sources to form the coal blend 140. In some embodiments, not all of the coal types shown in FIG. 1 are utilized to form the coal blend 140 (e.g., only type A coal 112 and type B coal 113 are used). Each of the coals 110 can be tested using a coal parameter measurement system 120 to determine coal parameters, such as a VM mass fraction, ash composition measurement, sulfur composition measurement, inert matter composition, etc. Some embodiments can also use other properties of the coal, such as a fluidity of tar in the coal, and AFT for the coal, vitrinite reflectance, etc., when selecting the type or amount of coals to use for a coal blend. Alternatively or additionally, some embodiments of the present technology can obtain coal parameters from a third-party data source (e.g., a database application program interface (API), or a user's manual input into an input device, such as a keyboard or touchscreen, etc.).

In some embodiments, the coal parameters can consider measurements of reactive components or subtypes of reactive components, such as vitrinite, liptinite, and reactive semifusinite. The coal parameters can also include measurements or select an amount of inert material to include into a coal blend, such as breeze, inert semifusinite, fusinite, macrinite, and mineral matter. In some embodiments, the inert content of a coal blend can be greater than or equal to 32.0%, or can be restricted to a particular range, such as between 28.0%-40.0%, or between 33.0%-35.0%. Some embodiments can determine the type and quantity of coals, breeze, and other components of a coal blend to satisfy a set of target coal blend parameters or corresponding target coke blend parameter, such as a target coal blend parameter, indicating a strong uniform coke. For example, some embodiments of the present technology can select the types of vitrinites that are present in a coal blend, where the types of vitrinite can include one or more of V9, V10, V11, V12, V13, V14, V15, V16, V17, V18, and V19.

After obtaining coal parameters for the coals 110, some embodiments of the present technology can determine combinations of coal types of the coals 110. For example, a first combination of coal types can include 20% type A coal 112, 30% type B coal 113, 40% type C coal 114, and 10% type D coal 115. Some embodiments can represent each combination of coal types with a vector in an n-dimensional mixture space, where "n" can represent an integer equal to or less than the number of available coal types usable to generate a coal blend. For example, some embodiments of the present technology can represent the first combination with a vector [0.2, 0.3, 0.4, 0.1] to represent a mixture point, where the mixture point can indicate the proportional amount of each coal in the coal blend. Furthermore, some embodiments of the present technology can add additives to a coal blend. Such additives can include calcium oxide, limestone, a calcium-containing material, trona, soda ash, caustic soda, slag (e.g., low ash fusion slag, a basic oxygen furnace (BOF) slag, a cupola slag, etc.), iron, nickel, potassium, magnesium, sodium, calcium sulfate, rockwool, biochar, or biomass (e.g., a low-AFT biomass). Alternatively or additionally, some embodiments of the present technology can add mineral additives, such as dolomite, various other calcium-containing minerals, iron-containing minerals, magnesium-containing minerals, or sodium-containing minerals. Some embodiments can use metal oxides as additives to a coal blend, such as $Al_2O_3$, $SiO_2$, $Fe_2O_3$, MgO, $Na_2O$, or TiO, transition metal oxides, calcined minerals. Some embodiments can add metal halide additives, such as $CaCl_2$, $MgCl_2$, NaCl. Some embodiments can add metal sulfates additives to a coal blend, such as $CaSO_4$. Some embodiments can add aluminum or silicon mineral additives to a coal blend, such as Quartz, Muscovite, or Feldspar. Some embodiments can add additives from industrial waste or recycling streams, such as blast furnace slag, foundry cupola slag, metal fines, wallboard waste, flue gas desulfurization plant gas byproduct (e.g., fly ash), coal burning plant fly ash, heat recovery steam generator wash mud, or unwashed coal.

Once an additive is added, the coal blend can have a calcium mass fraction, a lime mass fraction, a trona mass fraction, a soda ash mass fraction, a caustic soda mass fraction, a low ash fusion slag mass fraction, a BOF slag mass fraction, a cupola slag mass fraction, an iron mass fraction, a nickel mass fraction, a potassium mass fraction, a magnesium mass fraction, a sodium mass fraction, a calcium sulfate mass fraction, a rockwool mass fraction, a biochar mass fraction, a biochar mass fraction, a biomass mass fraction, or another additive mass fraction that is greater than 0% but less than a predetermined threshold. The threshold can vary based on particular embodiments, and can be configured such that the additive mass fraction is less than 10.0%, less than 5.0%, less than 3.0%, less than 1.0%, etc. By using a small amount of the additives, some embodiments of the present technology can significantly lower an ash fusion value or another property that increases the efficiency of a coke product. Alternatively or additionally, some embodiments of the present technology can include a greater amount of additives, where the coal blend can include more than 10.0% of an additive. For example, some embodiments of the present technology can use an additive having a calcium oxide mass fraction greater than 70.0%, where inclusion of the additive can raise a calcium oxide mass fraction of a coal blend to be greater than 10.0%. Unless otherwise indicated, an element mass fraction can refer to the element itself, compounds containing the element, or both. For example, a calcium mass fraction can refer to a mass fraction of only calcium in a material, a mass fraction of calcium oxide, or a mass fraction of another calcium-containing compound, or a combined mass fraction of any combinations thereof, etc.

In many cases, the VM of coal includes vitrinite, where vitrinite can be categorized based on its reflectance or other physical properties. Some systems can categorize vitrinite by vitrinite types V8 to V18, where different coals can include different distributions of vitrinite types. As used in this disclosure, a high volatility coal can be characterized by having a VM mass fraction that is greater than a VM mass fraction threshold, where different systems can define a high volatility coal using different threshold. For example, some embodiments of the present technology can characterize a high volatility coal as a coal having a VM mass fraction that is greater than or equal to 28.0%. Some embodiments can use other VM mass fraction thresholds to characterize a high volatility VM, such as 25.0%, 27.0%, 30.0%, 31.0%, or some other threshold greater than or equal to 25.0%.

As used in this disclosure, a low volatility coal can be characterized by having a VM mass fraction that is less than a VM mass fraction threshold, where different systems can define a low volatility coal using different thresholds. For example, some embodiments of the present technology can characterize a low volatility coal as a coal having a VM mass fraction that is less than or equal to 20.0%, though a different value other than 20% can be used, such as 14.0%, 15.0%, 17.0%, 21.0%, etc. Some embodiments of the present technology can use other VM mass fraction thresholds to characterize a high volatility VM as a VM greater than the mass fraction threshold. The mass fraction threshold can be equal to a value such as 14.0%, 15.0%, 21.0%, 22.0%, 23.0%, or some other threshold less than or equal to 25.0%.

Some embodiments of the present technology can characterize or partially characterize a low volatility coal with respect to a high volatility coal by using a pre-determined difference, where the pre-determined difference can include a value greater than 1.0%, such as 2.0%, 3.0%, 4.0%, 8.0%, or some other value. For example, some embodiments of the present technology can set the difference between a first threshold used as the threshold for a high volatility coal and a second threshold used as the threshold for a low volatility coal as being equal to 4.0%, where a selection of 30% as the first threshold can cause a system to automatically select 26% as the second threshold. Alternatively, some embodiments of the present technology can determine or permit an alternative value to be the second threshold, such as 21%. By setting the thresholds used to define a high volatility coal and a low volatility coal or defining a difference between the two thresholds, some embodiments of the present technology can also automatically define a middle volatility coal as those coals that are not high volatility coals or low volatility coals.

This disclosure refers to the AFT of coal blends or coke products. An AFT of a coke product can be determined in various ways, such as via experimental observation (observed AFT) or determined using an empirical model (model AFT). Unless otherwise specified, the term "ash fusion" can refer to either an empirical model for ash fusion or an observed ash fusion. As will be discussed elsewhere, an AFT can be less than or equal to 2600° F., less than or equal to 2450° F., less than or equal to 2400° F., less than or equal to 2350° F., less than or equal to 2300° F., less than or equal to 2250° F., less than or equal to 2200° F., less than or equal to 2150° F., less than or equal to 2100° F., less than or equal to 2050° F., less than or equal to 2000° F., less than or equal to 1950° F., less than or equal to 1900° F., less than or equal to 1850° F., or less than or equal to 1800° F.

In some embodiments, an empirical model of AFT can be determined from remaining compounds of an ash generated from combustion of a coke product. When the value of the AFT is constrained to a range, these empirical models can serve to form a composition boundary in a multi-dimensional composition parameter space. The composition parameters of the parameter space can represent amounts of an element or compound in a material or group of materials, where the amounts can include compound mass fractions of their corresponding compounds, volumetric fractions, etc. By using different empirical models or different ranges for an AFT, some embodiments constrain the ash of a coke product to different regions in a composition parameter space, which can then constrain the composition of the coke product itself. For example, empirical models for the ash fusion can be defined in Equations 1-3 below, where "AFT" can be a model ash fusion temperature in degrees Celsius (° C.), "$SiO_2$_mass_fraction" can be a $SiO_2$ mass fraction of the ash of the coke product ("coke product ash"), "$Al_2O_3$_mass_fraction" is a $Al_2O_3$ mass fraction of the coke product ash, "$Fe_2O_3$_mass_fraction" is a $Fe_2O_3$ mass fraction of the coke product ash; "CaO_mass_fraction" is a CaO mass fraction of the coke product ash; "MgO_mass_fraction" is a MgO mass fraction of the coke product ash; and "$K_2O$_mass_fraction" is a $K_2O$ mass fraction of the coke product ash:

AFT=19×($Al_2O_3$_mass_fraction)+15× ($SiO_2$_mass_fraction+$TiO_2$_mass_fraction)+10× (CaO_mass_fraction+MgO_mass_fraction)+6× ($Fe_2O_3$_mass_fraction+$Na_2O$_mass_fraction)  Equation 1

AFT=19×($Al_2O_3$_mass_fraction)+15× ($SiO_2$_mass_fraction+$TiO_2$_mass_fraction)+10× (CaO_mass_fraction+MgO_mass_fraction)+6× ($Fe_2O_3$_mass_fraction+$Na_2O$_mass_fraction+ $K_2O$_mass_fraction)  Equation 2

AFT=401.5+(26.3×$SiO_2$_mass_fraction+40.7× $Al_2O_3$_mass_fraction)−11.0× $Fe_2O_3$_Mass_Fraction−7.9×CaO_mass_fraction− 112×MgO_mass_fraction  Equation 3

Some embodiments can apply different models based on different compositions. For example, based on a determination that an $Al_2O_3$ and SiO 2 mass fraction in the ash composition of a coal blend is between 65% and 80%, some embodiments of the present technology can use Equation 3 to compute a model AFT, and use Equation 2 to compute the model AFT otherwise. Some embodiments can use different models for different optimization operations. For example, some embodiments of the present technology can use Equation 3 to optimize a coal blend selected for coke production to have a lower content of $Al_2O_3$ and $SiO_2$ while having a greater content of $Fe_2O_3$ and CaO. Furthermore, while some embodiments of the present technology can use a known model AFT, some embodiments of the present technology can use novel model AFT equations. For example, some embodiments of the present technology can use Equation 1 to determine an AFT, where Equation 1 can be found in Chapter 8 of *Cupola Handbook*, 6th ed., © 1999, American Foundrymen's Society, Inc., which is incorporated by reference herein, some embodiments of the present technology can use other AFT models, such as those described by Equation 2 or Equation 3. Various other limitations on the mass fractions of components of a coal blend can be imposed. For example, some embodiments of the present technology can produce a coal blend having an alumina $Al_2O_3$ content of ash of a coal blend as being less than 10.0%, less than 7.0%, less than 6.0%, less than 5.0%, etc.

By constraining an AFT to a specific boundary, some embodiments of the present technology can restrict the composition of an ash. In some embodiments, the specific boundary can encompass a temperature region such as 982° C. (1800° F.) to 1204° C. (2200° F.), 1204° C. (2200° F.) to 1426° C. (2600° F.), or 982° C. to 1426° C. If the ash is an ash product generated by combusting a coke product, restrictions on the composition of the ash results in a constraint on the coke product of the coke product itself. For example, some embodiments of the present technology can generate a coke product having certain amounts of Al, Si, Ti, Ca, Mg, Fe, Na, or K such that combustion of the coke product results in an ash having the composition that satisfies Equation 2. Various composition boundaries on a coke product ash can be used. For example, some embodiments of the present technology can generate a coke product such that a model AFT of the coke product as determined by Equation 3 is within an AFT boundary. For example, the AFT boundary can be a temperature range between 1260° C. (2300° F.) and 1427° C. (2600° F.), between 1260° C. and 1371° C. (2500° F.), between 1260° C. and 1316° C. (2400° F.), or between 1260° C. and 1427° C. In some embodiments, a lower bound on the temperature can be a different value, such as 982° C. (1800° F.) or a value less than 1288° C., such as 816° C. (1500° F.), 649° C. (1200° F.), or some other value less than 1288° C.

Furthermore, some embodiments of the present technology can constrain an AFT to be approximately a target value, wherein a parameter is approximately a target value if the parameter is within 10% of the absolute value of the target value. For example, some embodiments of the present technology can constrain an AFT to be approximately 982° C. (1800° F.), 1204° C. (2200° F.), 1260° C. (2300° F.), 1288° C. (2350° F.), 1316° C. (2400° F.), 1343° C. (2450° F.), 1371° C. (2500° F.), 1399° C. (2550° F.), or 1427° C. (2600° F.).

In some embodiments, a coal blend formulation can include specific properties, such as an ash fusion value less than or equal to 2400° F., which is equivalent to being less than 1316° C. Some embodiments can recommend or produce a coal blend that contains low-VM mass fraction coals and high-VM mass fraction coals without necessarily including middle-VM mass fraction coals. For example, a coal blend can have a bimodal profile of high-VM and low-VM coals within the coal blend. In such a bimodal profile, the coals of a coal blend can include only first and second sets of coals, where a first set of coals of the coal blend can include only high-VM coals having a VM mass fraction greater than 30.0%, and a second set of coals of the coal blend can include only low-VM coals having a VM mass fraction less than 22.0%.

Some embodiments can map the mixture point to a corresponding coal parameter point in a coal parameter space ("coal parameter point"), where each dimension in the coal parameter space can represent a coal parameter. In some embodiments, a dimension of a coal parameter point can be determined as a linear combination of the coals 110 weighted by the values of the corresponding mixture point. For example, a coal blend can include a two-coal-type mixture that includes 50% type A coal 112 and 50% type B coal 113. If the type A coal 112 has a VM mass percentage equal to 15% and the type B coal has a VM mass percentage equal to 25%, the VM mass percentage of the coal blend can be equal to the mean average of the two VM mass percentages, 20%.

Some embodiments can obtain a set of target coal parameters, where a target coal parameter can be provided as a default value, provided by manual data entry, obtained from a third-party data store, provided via an electronic message, etc. For example, the target coal parameter can include a coke reactivity index (CRI) or a coke strength after reaction (CSR) value. In some embodiments, the CRI or CSR can be manually entered by a user, obtained from a database, received via an API, etc. Some embodiments can use a model based on a set of coal parameters to determine a corresponding set of coke parameters. The model can include a statistical model, a semi-empirical analytical model, a neural network model, a physical simulation model, etc. As described elsewhere in this disclosure, some embodiments of the present technology can use a model that accounts for non-linear relationships between coal parameters and coke parameters. For example, some embodiments of the present technology can use a neural network, such as feed forward neural network, to predict a set of coke parameters.

In some embodiments, the neural network can be trained with past data. For example, some embodiments of the present technology can train a neural network based on past blends and outcomes of the blends where the outcomes can include coke properties such as a CSR, a percentage weight loss, a CRI, or another coke parameter that is non-linear with respect to a related coal parameter. Alternatively, or additionally, some embodiments of the present technology can use an analytical physics-based model or semi-analytical model to predict a coke parameter. The use of a neural network, or other non-linear methods to predict coke parameters based on coal parameters can be advantageous due to non-linear effects associated between coal parameters and coke parameters. Furthermore, some embodiments of the present technology can provide additional inputs to the neural network model, such as a breeze parameter, an amount of breeze used, etc.

Some embodiments can adapt to changes in the availability of different coal types. For example, a source mine for type A coal 112 can be shut down, a transportation line carrying type A coal 112 can be significantly delayed, a regulatory environment can make the use of certain coals infeasible for use, etc. In response to a determination that a coal type used in a coal blend is unavailable or expected to become unavailable, some embodiments of the present technology can generate an alternative coal blend formulation that maps to a position in a coal parameter space that is within a distance threshold of a first point in the coal parameter space. For example, some embodiments of the present technology can originally use a first coal blend that is 20% type A coal by weight, where the first coal blend maps to a first point in a coal parameter space that includes a VM mass ratio of 25%, a sulfur mass ratio of 0.4%, and ash mass ratio of 6%, etc. After receiving a message indicating that type A coal is restricted to 5% (e.g., as a result of an inventory drop), some embodiments of the present technology can perform a set of operations to determine one or more additional combinations that satisfy the coal type use restrictions and the coal parameter space. In cases where the first coal parameter point is not achievable while constrained by coal type availability, some embodiments of the present technology can determine an alternative coal blend formulation that maps to a coal parameter point that is within a coal parameter space distance threshold of the first coal parameter point.

Some embodiments can use the mixture point to determine mixture of coals to add and process for the coal blend 140. For example, some embodiments of the present technology can use operations described in this disclosure to determine a mixture point indicating a coal mixture that includes 20% type A coal 112, 30% type B coal 113, 40% type C coal 114, and 10% type D coal 115 and combine coal in these respective proportions into the coal blend 140. Some embodiments can then provide the mixed coal into a coke oven 150, where some embodiments of the present technology can add coke breeze 111 to the coke oven 150 to create a coke product having coke properties similar to or the same as a set of target coke properties.

Figure 2:
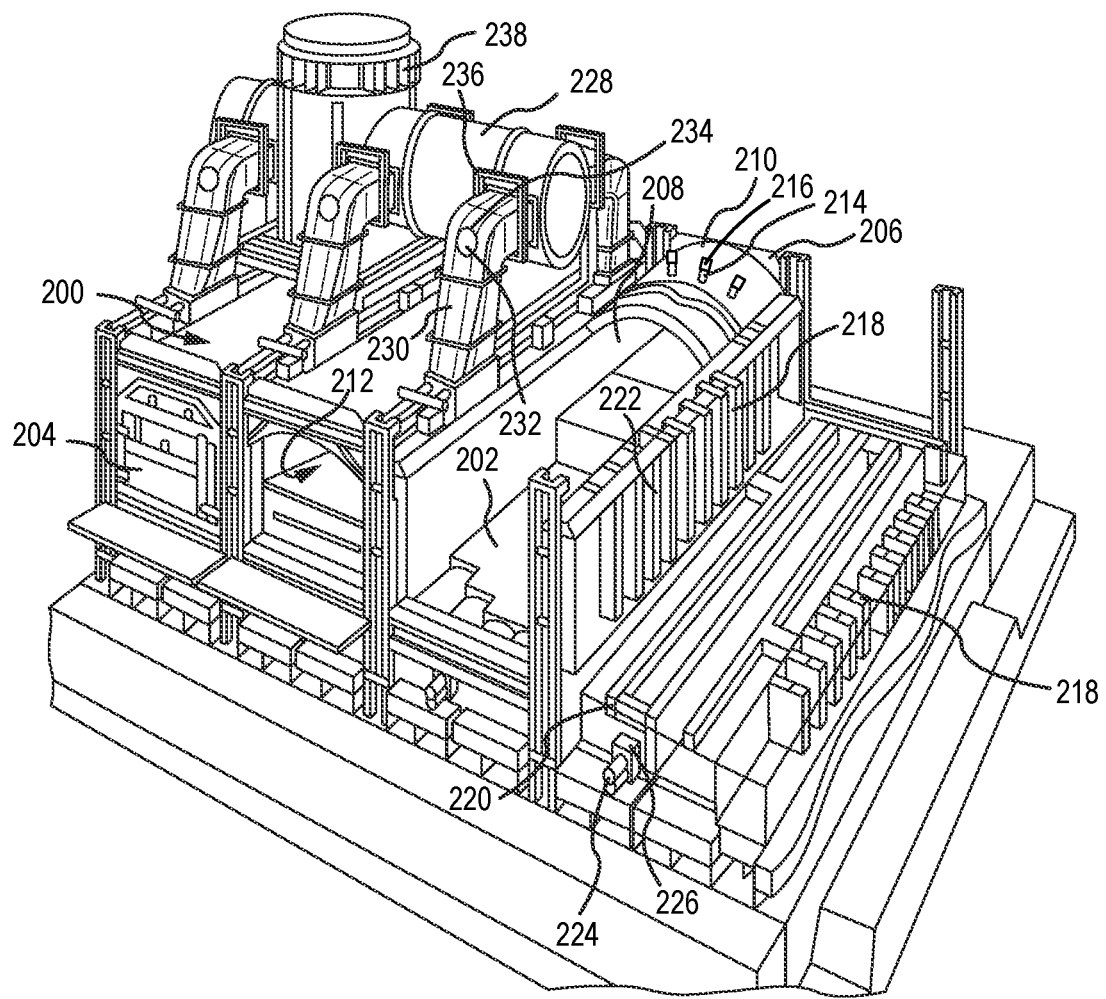
FIG. 2 depicts an isometric, partial cut-away view of a portion of a horizontal heat recovery coke plant, in accordance with one or more embodiments of the present technology.

FIG. 2 depicts an isometric, partial cut-away view of a portion of a horizontal heat recovery coke plant, in accordance with one or more embodiments of the present technology. An oven 200 of the coke plant can include various ducts, chambers, valves, sensors, or other components. For example, the oven 200 can include an open cavity defined by an oven floor 202, a pusher side oven door 204, a coke side oven door 206 opposite the pusher side oven door 204, opposite sidewalls 208 that extend upwardly from the oven floor 202 and between the pusher side oven door 204 and coke side oven door 206, and an oven crown 210, which forms a top surface of the open cavity of an oven chamber 212. Furthermore, the oven 200 can include a set of crown air inlets 214 that allows primary combustion air into the oven chamber 212. In some embodiments, the set of crown air inlets 214 can penetrate the oven crown 210 and permit open fluid communication between the oven chamber 212 and the environment outside the oven 200. In some embodiments, air flow through air inlets or air ducts (e.g., an uptake duct) can be controlled by dampers, which can be configured at any of a number of states between a fully open state and a fully closed state to vary an amount of air flow. For example, the crown air inlets 214 can include a damper that can be configured into different states to permit air flow into the oven crown 210, such as a crown inlet air damper 216, that operate in a similar manner. While embodiments of the present technology can use crown air inlets 214, exclusively, to provide primary combustion air into the oven chamber 212, other types of air inlets, such as the door air inlets, can be used in particular embodiments without departing from aspects of the present technology.

As discussed above, control of the draft in the oven 200 or other operations in the oven 200 can be implemented by control systems. Such operations can include operations of a coking cycle, which can include charging a coal blend into the oven 200, controlling the uptake damper 236 to be configured at any one of a number of states between fully open and fully closed, etc. Upon completion of the coking cycle, some embodiments of the present technology can coke out a coal blend to produce a coke product useful for producing steel with a cupola furnace. In some embodiments, foundry coke products may be used in a cupola furnace using operations described in U.S. application Ser. No. 18/052,739, titled "FOUNDRY COKE PRODUCTS AND ASSOCIATED SYSTEMS AND PROCESSING METHODS VIA CUPOLAS," the disclosure of which is included herein as Appendix A. In some embodiments, the coke product can be removed from the oven 200 through the coke side oven door 206 with a pusher ram or another mechanical extraction system. In some embodiments, the coke can be quenched (e.g., wet or dry quenched) and sized before delivery to a user.

FIG. 3 is a table indicating volatile matter (VM) fractions for different types of coals usable in a coal blend, in accordance with one or more embodiments of the present technology. The vitrinite content and their corresponding categories for various types of coal is shown in table 300. The coals listed in row 301 include coal types, "T1," "T2," "T3," "T4," "T5," "T6," "T7," and "T8." As shown by the table 300, some coals can be considered low volatility coal, where a low volatility coal includes primarily vitrinites having low volatility, such as vitrinites V14, V15, V16, V17, or V18. As shown by the table 300, some coals can be considered high volatility coal, where a high volatility coal includes primarily vitrinites having high volatility, such as vitrinites V8, V9, or V10. Some coals can be considered middle volatility coals, where a middle volatility coal includes primarily vitrinites having volatilities that would not be considered high volatility or low volatility, such as vitrinites V11, V12, or V13.

As described elsewhere in this disclosure, some embodiments of the present technology can select a coal blend that includes primarily high volatility or low volatility coals. For example, some embodiments of the present technology can determine, recommend, or select coals indicated in the table 300 for inclusion in a coal blend, where the selected coals include the low volatility coals T1 and T2 and the high volatility coals T8 and T9. As shown in the columns 311-312, low volatility coals can be characterized by a proportionally higher amount of low volatility of vitrinites, such as V15 vitrinites and V16 vitrinites, relative to higher volatility vitrinites, such as V13 vitrinites. Similarly, as shown in the column 313, high volatility coals can be characterized by having a relatively higher amount of V8, V9, and V10 vitrinites relative to other vitrinites of the coal.

As described elsewhere in this disclosure, some embodiments of the present technology can generate unique coal blends by omitting middle volatility coals from a coal blend to increase the yield of coke products produced with the coal blend. Such coal blend can be unique for lacking middle volatility coals despite conventional methods which produce and use coal blends that include middle volatility coals due to conventional assumptions about the need for middle volatility coals to balance vitrinites during a coke-producing pyrolysis reaction. For example, a coal blend can include high volatility coals and low volatility coals. The high volatility coals can have a high volatility vitrinite fraction such that the majority of the vitrinite fraction of a high volatility vitrinite fraction is made of high volatility vitrinites such that the sum of the V8 vitrinite fraction, V9 vitrinite fraction, V10 vitrinite fraction, and V11 vitrinite fraction is greater than 50%. The low volatility coals can have a low volatility vitrinite fraction such that the majority of the vitrinite fraction of a low volatility vitrinite fraction is made of low volatility vitrinites such that the sum of the V14 vitrinite fraction, V15 vitrinite fraction, V16 vitrinite fraction, V17 vitrinite fraction, and V18 vitrinite fraction is greater than 50%. As used in this disclosure, a V16 vitrinite fraction (which can include having a volumetric fraction greater than 50%, a mass fraction grater 50%, etc.), where a vitrinite fraction can be relative to the total amount of maceral content of the coal or the total mass of the coal.

In some embodiments coals of the coal blend can have different ash fusion values, as shown by table 400. As will be indicated elsewhere in this disclosure, and output ash fusion can be lower in a coal blend compared to one or more constituent coals of the coal blend. For example, as described elsewhere herein, a coal blend comprising coal type T1, coal type T2, and coal type T9 can have an ash fusion value that is different from any of these values. As discussed elsewhere in this disclosure, some embodiments of the present technology can consider various coal parameters when determining a mixture of coals for a coal blend. For example, some embodiments of the present technology can obtain coal parameters for a set of coal types T1-T9, as indicated in the table 400. Some embodiments can then determine an amount of coals, breeze, or other additives for a coal blend. For example, some embodiments of the present technology can obtain a set of sulfur values shown in row 413 of the table 400 and a set of ash fusion values shown in row 420. Some embodiments can then obtain a target ash fusion value as a target coal blend parameter and determine a coal blend composition from the coals T1-T9.

As described elsewhere in this disclosure, some embodiments of the present technology can constrain or otherwise restrict the coals being used to low volatility or high volatility coals without using middle volatility coals. For example, if the coals of coal type TI are low volatility coals, the coals of coal type T5 are a middle volatility coal, and the coal of coal type T9 are a high volatility coal, some embodiments of the present technology can be restricted from using coals of coal type T5 when determining which coals to use for a coal blend. Furthermore, some embodiments of the present technology can restrict the use of coals of specific coal types or require the use of coals a specific coal types. For example, some embodiments of the present technology can receive instructions requiring the use of coals having a VM mass fraction between 0% and 20%, which can restrict a coal blend to including coals of at least one of coal type T1 or coal type T2. Furthermore, some embodiments of the present technology can obtain a plurality of target coal blend parameters or a range or plurality of ranges of target coal blend parameters. Some embodiments can provide a corresponding number of possible combinations of coals of different coal types that satisfy these sets of target coal blend parameters or ranges of coal blend parameters.

FIG. 4 is a table indicating properties associated with different types of coals used in a coal blend, in accordance with one or more embodiments of the present technology. As shown in the table 400, coals of different coal types can have different properties, where some embodiments of the present technology can use properties as coal parameters for use in satisfying a target parameter. For example, some embodiments of the present technology can receive program instructions to satisfy a target parameter representing a required VM for a coal blend. In response some embodiments of the present technology can determine a range of VM values represented by a row 411 of the table 400 that satisfy the required VM for the coal blend or a range required VM value. Some embodiments of the present technology can perform similar operations for each of the coal properties listed in rows 411 to 428.

FIG. 5 is a table indicating the composition associated with different types of coals used in a coal blend, in accordance with one or more embodiments of the present technology. As shown in the table 500, coals of different coal types can have different compositions. Some embodiments can use material compositions as coal parameters for use in satisfying a target coal parameter. For example, some embodiments of the present technology can receive program instructions to satisfy a target coal parameter representing a required calcium oxide value or range of calcium oxide values. In response, some embodiments of the present technology can determine a range of coal compositions of the coal types T1-T9 that satisfy the required calcium oxide value or range of calcium oxide values.

FIG. 6 is a table indicating additional measurements associated with different types of coals used in a coal blend, in accordance with one or more embodiments of the present technology. As shown in the table 600, a coal blend can include various compounds. Due to heterogeneity and sources of variation within coal sources, coal blends of the same coal type at the same ratios can yield different sample values for each coal blend sample that is tested.

Figure 7:
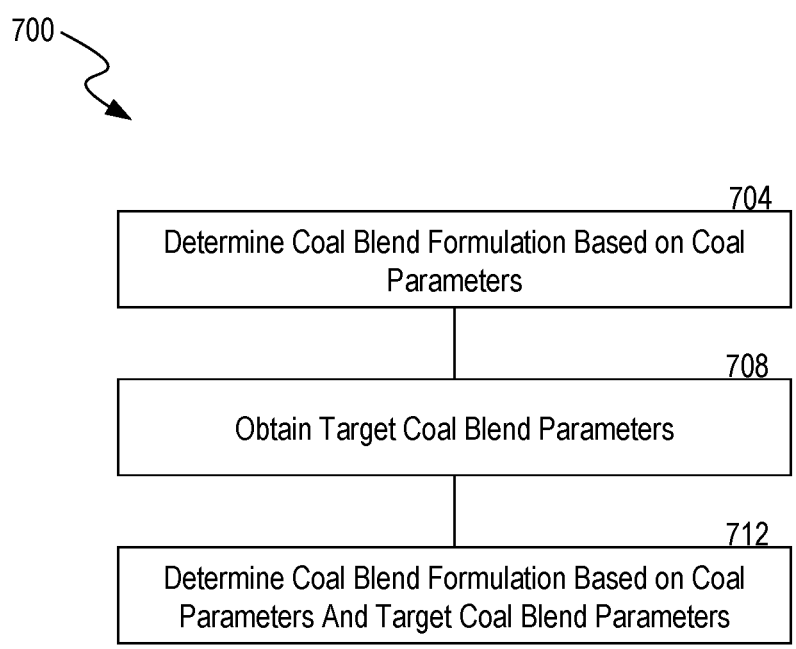
FIG. 7 is a flowchart for a process to determine a coal blend formulation, in accordance with one or more embodiments of the present technology.

FIG. 7 is a flowchart for a process to determine a coal blend formulation, in accordance with one or more embodiments of the present technology. Some embodiments can obtain a set of coal parameters for an available set of coals, as indicated by block 704. As described elsewhere, coal parameters can include various properties or compositions associated with a specific type of coal. For example, a coal blend can include a relative or absolute measure of VM, ash, sulfur, total inert material, mineral matter, model AFT, an AFT ST value, an AFT HT value, a solidification temperature, a dilation, an amount of a specific type of volatile material (e.g., an amount of V8 vitrinite, V9 vitrinite, etc.) or other coal parameter. Some embodiments can obtain coal parameters from a user input, from an historic record of values stored in a database, from an application program interface (API), etc.

Some embodiments of the present technology can obtain a set of target coal blend parameters, as indicated by block 708. For example, some embodiments of the present technology can obtain a target coal blend parameter based on an input provided by a user via a graphical user interface (GUI). Alternatively, or additionally, some embodiments of the present technology can obtain a target coal blend parameter from a stored configuration file, a record of historical values, or an API. Some embodiments can estimate, predict, or otherwise determine a target coal blend parameter from a target coke parameter. For example, some embodiments of the present technology can obtain a target reactivity and sulfur mass fraction as a target coke parameter. Some embodiments can then provide a machine learning prediction model with the target coke parameter to determine a set of target coal blend parameters.

Some embodiments of the present technology can determine a coal blend formulation based on the set of coal parameters and set of target coal blend parameters, as indicated by block 712. Some embodiments can determine a percentage or other type of ratio indicating an amount of a coal type to use in a coal blend by manipulating the type and amount of coals to use to match a set of target coal parameters. For example some embodiments of the present technology can receive program instructions or parameters of the configuration files indicating a target coal parameter for a target VM content. Some embodiments can then perform a set of operations to compute a mixture point representing the mixture of different coals corresponding with different coal types. For example, some embodiments of the present technology can perform an optimization operation to determine a region in a coal parameter space that can be satisfied by selecting different coals from a set of available coals.

Some embodiments of the present technology can be restricted from determining coal blends that include middle volatility coals, such as a coal having a VM mass fraction such that V11, V12, or V13 vitrinites are the primary components of the VM mass fraction or coal blend maceral content. For example, some embodiments of the present technology can first receive a target coal parameter indicating that a target VM mass fraction is 0.25 or some other value that is greater than or equal to 10%, 20%, 25%, etc. Some embodiments can then explore a coal parameter space formed by possible mixtures of different coal types to satisfy this target VM mass fraction, where the exploration can include low volatility coal types or high volatility coal types while excluding middle volatility coal types. Some embodiments can determine a coal blend formulation such that a mass fraction of low volatility coals of the coal blend is greater than or equal to a first mass fraction threshold and a mass fraction of high volatility coals of the coal blend is greater than or equal to a second mass fraction threshold, where the first mass fraction threshold can be greater than or equal to 50% and the second mass fraction threshold can be less than or equal to 50%. For example, some embodiments of the present technology can determine a coal blend formulation such that a mass fraction of low volatility coals of the coal blend is greater than or equal to 60% and a mass fraction of high volatility coals of the coal blend is greater than or equal to a 15%. Alternatively, or additionally, some embodiments of the present technology can determine a coal blend formulation such that a mass fraction of high volatility coals of the coal blend is greater than or equal to a first mass fraction threshold and a mass fraction of low volatility coals of the coal blend is greater than or equal to a second mass fraction threshold, where the first mass fraction threshold can be greater than or equal to 50% and the second mass fraction threshold can be less than or equal to 50%. For example, some embodiments of the present technology can determine a coal blend formulation such that a mass fraction of high volatility coals of the coal blend is greater than or equal to 60% and a mass fraction of low volatility coals of the coal blend is greater than or equal to 15%.

As described elsewhere in this disclosure, a low volatility coal type can have a corresponding volatility that is less than or equal to a first volatility threshold, and a high volatility coal type can have a corresponding volatility that is greater than or equal to a second volatility threshold, where the first volatility threshold can be less than the second volatility threshold. With reference to FIG. 3, some embodiments of the present technology can generate a coal blend formulation indicating a coal blend that includes breeze, coal type T1, coal type T2, and coal type T9. However, despite such unconventional mixtures for a coal blend, some embodiments of the present technology can produce a resulting coke product having an ash fusion value within a useful parameter range, such as an ash fusion value equal to 2526° F., or a coke product having an enhanced CRI, such as a CRI that is greater than or equal to 30%, greater than or equal to 35%, or greater than or equal to 40%.

As described elsewhere in this disclosure, some embodiments of the present technology can recommend a coal blend formulation that includes coke breeze. Some embodiments can select coke breeze or an amount of coke breeze for inclusion based on breeze parameters associated with the coke breeze. For example, some embodiments of the present technology can obtain a VM mass fraction of breeze, an ash mass fraction of the breeze, or a sulfur mass fraction of the breeze. Some embodiments can then determine an amount of coke breeze to include in a coal blend based on the obtained set of breeze parameters. In some embodiments, the range for an amount of coke breeze to include in a coal blend can be between 1% to 20% coke breeze, though other ranges are possible. For example, some embodiments of the present technology can recommend a coal blend formulation that includes 10% coke breeze based on a determination that this amount of coke breeze, in combination with other coals, satisfy a set of target coal blend parameters.

Some embodiments of the present technology can determine a coal blend having a relatively high ash mass fraction. While some embodiments of the present technology can use a low ash mass fraction in a coal blend (e.g., less than 10.0%), some embodiments of the present technology can recommend a coal blend formulation having an ash mass fraction that is greater than or equal to 10.0%, where an ash mass fraction that is greater than 10.0% can be considered a high ash content for a coal blend. For example, some embodiments of the present technology can determine a coal blend formulation that has an ash mass fraction that is greater than or equal 10.0%, 11.0%, 15.0%, or 20%. By increasing the use of ash in a coal blend, some embodiments of the present technology can increase the effective strength of a coke product produced from a coal blend. Furthermore, recycling ash byproduct from a coking operation increases the resource efficiency of operations to produce coke product from a coal blend by reducing the reliance on additional additives for a coal blend.

Some embodiments of the present technology can recommend a coal blend formulation that includes coke breeze that is restricted to a specific size or a range of sizes. For example, some embodiments of the present technology can recommend a first coal blend formulation that includes coke breeze that is restricted to being a 10-mesh coke breeze or larger coke breeze or a second coal blend formulation that includes coke breeze that is restricted to being a 20-mesh coke breeze or larger coke breeze. In some embodiments, different coal blend formulations can be recommended, where size restrictions can be negatively correlated with an amount of coke breeze being recommended for inclusion in a coal blend formulation. For example, some embodiments of the present technology can restrict a coal blend to using a coke breeze characterized as a 10 mesh coke breeze or larger coke breeze such that less than 5.0% of the coke breeze being used is characterized as the 10 mesh coke breeze or larger. Alternatively, or additionally, some embodiments of the present technology can use a coke breeze characterized as having a 20 mesh coke breeze or larger coke breeze such that less than 10.0% of the coke breeze being used is characterized as a 20 mesh coke breeze or larger. Alternatively, or additionally, some embodiments of the present technology can use a coke breeze characterized as having a 90 mesh coke breeze or smaller coke breeze such that less than 10.0%, less than 15.0%, or less than 25.0% of the coke breeze being used is characterized as a 90 mesh coke breeze or smaller.

As described elsewhere, some embodiments of the present technology can determine a coal blend formulation that includes multiple coal types, such as a first, second, and third coal type. Some embodiments can select the use of a coal type using optimization operations that satisfy one or more target coal blend parameters, where these optimization operations can compensate for limitations in coal availability, coal quantity, or coal variation between different batches of coal. For example, some embodiments of the present technology can recommend a coal formulation having a first amount of a first coal and a second amount of a second coal. The first coal can be a low volatility coal such that the mass fraction of V16 vitrinite is greater than 25% of the total VM mass fraction of the first coal, and the second coal can be a high volatility coal such that the sum of higher-volatility vitrinites, such as a sum of the fractions of V8 vitrinite, V9 vitrinite, and V10 vitrinite is greater than 40% of the total VM mass of the second coal. While some embodiments of the present technology can use 40%, as a threshold, other values are possible, such as 50%, 60%, 70%, or some other percentage greater than 40%.

While VM content is a significant concern for coal blend formulation, other properties such as ash fusion values, sulfur mass fraction, calcium mass fraction, or ash mass fraction can also be considered for the coal blend. For example, some embodiments of the present technology can provide a coal blend formulation indicating a sulfur oxide mass fraction of the coal blend that is greater than 5.0%, or a calcium oxide mass fraction of the coal blend that is greater than 5.0%. As will be discussed elsewhere in this disclosure, some embodiments of the present technology can benefit by using coal blends with higher reactivity or greater dimensions to compensate for elevated calcium or sulfur values. By permitting greater values of components, such as sulfur or calcium during coal blend formulation, some embodiments of the present technology can provide additional robustness that would not be viable for previous coal blend operations because the coal blends produced from such previous operations would have calcium or sulfur content that can be too high for foundry operations. Furthermore, while some target properties can be compositions, some properties can be based on other physical phenomena. For example, some embodiments of the present technology can produce a coal blend having a fluidity between 100 dial divisions per minute (ddpm) and 1200 ddpm or some other fluidity range, such as 200 ddpm and 1200 ddpm. Other ranges of fluidity for a coal blend is possible. For example, a fluidity of a coal blend can be greater than or equal to 100 ddpm.

As described elsewhere, some embodiments of the present technology can use a coke oven to produce a coke product or a population of coke products from a coal blend. As used in this disclosure, an ash fusion of a coal blend can be equivalent to an ash fusion of a coke product produced from the coal blend, and the two terms can be used interchangeably. Some embodiments can recommend a coal blend having an AFT that is within a range. For example, some embodiments of the present technology can recommend a coal blend having an AFT equal to 2326° F. or another temperature that is less than 2500° F. or another AFT threshold. In some embodiments, the AFT threshold can vary based on other target coke product parameters. In many cases, a coal blend that can be used to produce a coke product with a relatively reduced ash fusion, where a reduced ash fusion can provide downstream advantages during foundry operations in requiring fewer foundry resources or less coke product to produce steel or other foundry products.

Various types of optimization algorithms can be used to determine a mixture point for a coal blend of various components in order to satisfy a target coal blend parameter when confined within a parameter space of coal parameters.

Some embodiments can use a linear solver to determine for vectors representing mixture points in a parameter space. For example, a set of coke parameters can include a first subset of coke parameters and a second subset of coke parameters, where the first subset of coke parameters is non-linear with respect to any parameter of a coal parameter space, and where the second subset of coke parameters is linear with respect to at least one coal parameter. Some embodiments can determine a mixture point using a lower-upper (LU) decomposition of a matrix representing coal parameters to solve for a vector representing the second subset of coke parameters, where the solution vector can represent a first mixture point. Some embodiments can then predict a coke parameter, such as a CSR, based on the first mixture point. A determination that the predicted non-linear coke parameter does not satisfy a criterion based on a target non-linear coke parameter (e.g., not being equal to the target parameter, being greater or lesser than the target parameter by a value greater than a tolerance threshold, etc.) can cause some embodiments to select additional mixture points. Some embodiments can then determine a set of coal parameters corresponding with each additional mixture point and simulate or otherwise predict additional coke parameters based on the set of coal parameters. Some embodiments can then select one or more of the additional mixture points for use as a coal blend formulation based on the predicted additional coke parameters.

Some embodiments of the present technology can determine the coal blend formulation such that an aggregated VM mass fraction of the resulting coal blend will satisfy a target VM mass fraction or a range of target values. In some embodiments, a range of target values for a target VM mass fraction can be pre-determined. For example, some embodiments of the present technology can receive program instructions to recommend a coal blend formulation such that the aggregated VM mass fraction is between 17.0% and 25.0%. Some embodiments can then recommend a coal blend formulation that satisfies the range. For example, with reference to FIG. 3 and FIG. 5, some embodiments of the present technology can recommend a coal blend formulation including 12% coke breeze, 48% T1 coal, 20% T2 coal, and 20% T9 coal. While the above describes a VM range of 17.0% to 25.0%, other thresholds are possible. For example, some embodiments of the present technology can limit a VM mass fraction of a coal blend to be less than 27.0%, 30.0%, or some other value.

Some embodiments of the present technology can control a blending system to produce a coal blend based on the coal blend recommendation. Some embodiments can implement control systems to retrieve, process, and mix coals of different types to produce a coal blend in accordance with the ratios and materials indicated by a coal blend formulation. For example, some embodiments of the present technology can determine a coal blend formulation including 12% coke breeze, 48% T1 coal, 20% T2 coal, and 20% T9 coal. Some embodiments can then actuate a set of control mechanisms to mix 12 tons of coke breeze, 48 tons of T1 coal, 20 tons of T2 coal, and 20 tons of T9 coal into a mixing chamber to produce a coal blend.

Figure 8:
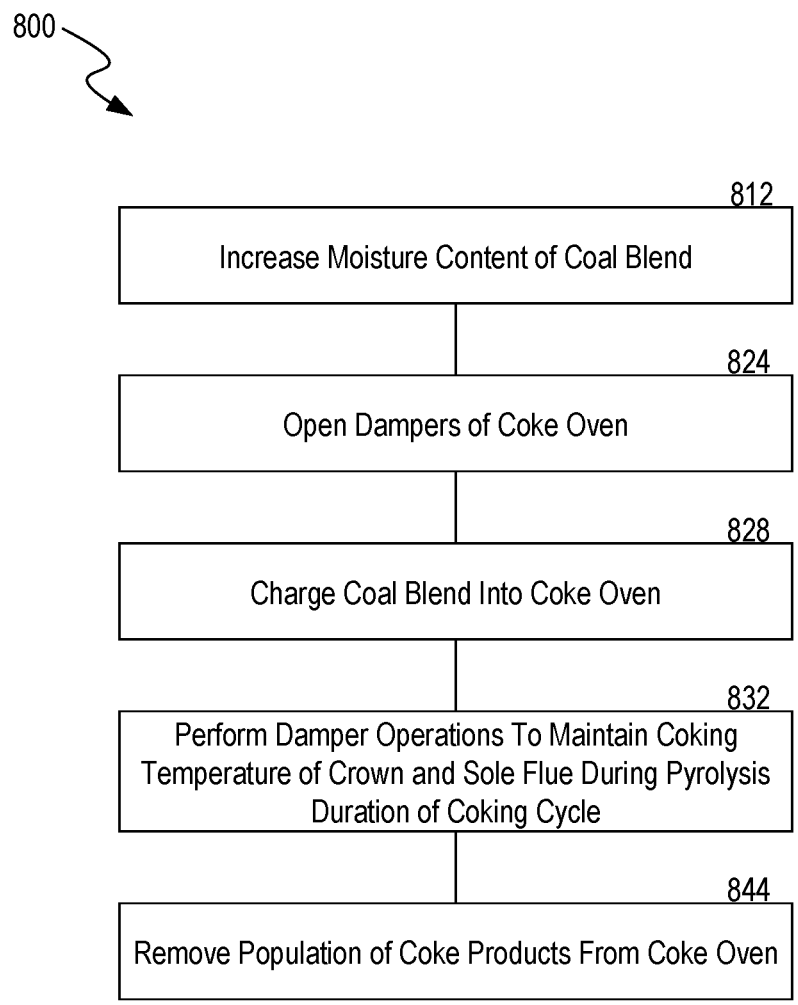
FIG. 8 is a flowchart for a process to produce a coke product using a coke oven, in accordance with one or more embodiments of the present technology.

III. Coking Coal Blends to Produce Foundry Coke Products, and Associated Systems and Methods FIG. 8 is a flowchart for a process to produce a coke product using a coke oven, in accordance with one or more embodiments of the present technology. Some embodiments can increase the moisture of a coal blend, as indicated by block 812. With reference to FIG. 2, a coal blend that is being charged into the oven chamber 212 can first be exposed to water to increase the moisture of the coal blend. For example, some embodiments of the present technology can activate a pump or valve to spray a coal blend with water or another fluid to increase the moisture of a coal blend as the coal blend is transported along a conveyor belt. It should be understood that a fluid that includes water can be described as water in this disclosure.

In some embodiments, a pump, valve or other mechanism can be controlled to spray fluid or otherwise expose a coal blend to a fluid to increase a moisture mass fraction of the coal blend to a value between 1.0% and 20.0%. Some embodiments can permit a degree of tolerance when increasing a moisture mass fraction of a coal blend. For example, some embodiments of the present technology can increase the moisture mass fraction of a coal blend to be greater than or equal to 8.0% and less than or equal to 13%. Some embodiments can use stricter tolerances, such as exposing a coal blend to an amount of water such that the moisture mass fraction of the coal blend is set to be between 10% and 12%. Some embodiments can determine an amount of water to spray based on a VM mass fraction of the coal blend. Some embodiments can add water such that a 1% decrease in moisture mass fraction from a baseline moisture content permits a 1% decrease in VM from a baseline value. For example, some embodiments of the present technology can add water to a coal blend such that a moisture mass fraction for the coal blend is equal to a VM mass fraction of the coal blend minus a preset value, such as 10%. Furthermore, though some embodiments use 10% as a preset value, other values are possible, such as 15%, 14%, 10%, 8%, 5%, or some other threshold value less than 50%.

Some embodiments of the present technology can include sensors to test the moisture of a coal blend and further increase or change a moisture mass fraction of a coal blend based on the measured moisture. For example, some embodiments of the present technology can determine that a measured moisture of a coal blend is less than a first moisture threshold and, in response, add additional fluid to a coal blend. Alternatively, some embodiments of the present technology can determine that a measured moisture is greater than a second moisture and, in response, add additional dry coal blend to the moistened coal blend. In some embodiments, the first moisture threshold can be a value greater than or equal to 1.0%, such as 5.0%, 10.0%, 12.0%, etc., and the second moisture threshold can be a value less than or equal to 15.0%, such as 15.0%, 13.0%, etc.

Some embodiments of the present technology can open the dampers of the coke oven, as indicated by block 824. Some embodiments can keep the dampers of a coke oven open during an initial heating period of the coke oven. For example, some embodiments of the present technology can use a set of controllers to send instructions to a damper actuator to open a set of sole flue dampers. Once set in an open state, the set of sole flue dampers can enable fluid communication between open atmosphere and a sole flue of a coke oven before a coal blend is placed into the coke oven and while the coal blend is placed into the coke oven. Furthermore, as described elsewhere in this disclosure, some embodiments of the present technology can use the set of controller sent instructions to the same actuator or a different actuator to change the state of the damper to a partially closed state or a fully closed state.

Some embodiments of the present technology can charge the coal blend into the coke oven, as indicated by block 828. As described elsewhere in this disclosure, some embodiments of the present technology can use a coke oven to produce coke products from a coal blend. Some embodiments can charge the coal blend by using a pusher charger machine and operations associated with the pusher charger machine.

Some embodiments of the present technology can take advantage of a heat recovery coke oven to reduce the fuel or power consumption of a coke oven. For example, some embodiments of the present technology can determine that a minimum temperature associated with the coke oven has been achieved by a measured temperature of coke oven. The minimum temperature can vary based on a specific implementation or coke oven and can be a temperature greater than 500° F., such as 1000° F., 1500° F., or some other temperature greater than 500° F. In response to a determination that a measured temperature of the coke oven has reached the minimum temperature, some embodiments of the present technology can initiate heat recovery operations, such as steam recovery operations, and reduce fuel consumption of the coke oven.

Some embodiments of the present technology can perform damper operations to maintain a coking temperature of the crown and sole flue of the coke oven during a pyrolysis duration of the coking cycle, as indicated by block 832. Some embodiments can perform a set of opening operations and closure operations of a set of dampers during a cycle. For example, some embodiments of the present technology can initially heat an oven during a coking cycle while a set of uptake dampers of the coke oven is in a fully open configuration. Some embodiments can then initiate a closure operation that causes the set of uptake dampers to switch to a second configuration, where the second configuration can be a partially open configuration or fully closed configuration. In some embodiments, the pyrolysis duration (sometimes called a coking duration) can be considered to have started once a lower bound coking temperature has been achieved, where the lower bound coking temperature can be a value that characterizes foundry coking temperatures, where the coking temperature can be a temperature greater than a byproduct temperature of 1800° F. or a temperature less than a blast temperature of 2500° F. For example, the lower bound coking temperature can be a value within a range, where the range can be within 1200-2300° F., 1800-2300° F., or 2000-2400° F. For example, the lower bound coking temperature can be 1990° F. In some embodiments, the pyrolysis duration can be considered to have ended once a coking reaction has ended, where a coal or coal blend that has reached the end of the coking reaction can be referred to as being "coked out." Some embodiments of the present technology can detect an end to a coking reaction in an oven based on a temperature reduction in a crown temperature or sole flue temperature. In some embodiments, the duration of a coking cycle can be determined as the sum of the duration of the pyrolysis time and a soak time, where a soak time represents the amount of time that a coke product is left in an oven at the conclusion of a pyrolysis duration before the coke product is removed from the oven.

Some embodiments can use sensor measurements to determine whether or not to open or close a valve. For example, some embodiments of the present technology can retrieve a set of crown temperature measurements from a crown temperature sensor. Some embodiments can then determine whether the set of crown temperature measurements satisfies a set of crown temperature criteria by determining whether a crown temperature threshold has been satisfied by one or more temperature measurements. Alternatively, or additionally, some embodiments of the present technology can determine whether the set of crown temperature measurements satisfies a set of crown temperature criteria by determining whether a temperature rate threshold is satisfied by changes to a sequence of crown temperature measurements. For example, some embodiments of the present technology can determine whether a temperature change rate of a crown temperature has increased to become greater than a temperature rate threshold of 50° F. per hour or some other value that is less than or equal to 50° F. per hour (e.g., a temperature rate threshold that is 35° F. per hour). In response to a determination that the temperature change rate satisfies the temperature rate threshold by being greater than or equal to the temperature rate threshold, some embodiments of the present technology can use a controller to actuate a damper to close or partially close in order to reduce an amount of air flow into a coke oven.

Some embodiments can maintain a temperature inequality between a crown temperature of the coke oven and the sole flue temperature of the coke oven during the pyrolysis duration. For example, some embodiments of the present technology can maintain a crown temperature between a range of 2000-2400° F. during a pyrolysis duration, where the crown temperature can vary within a pre-determined range. Furthermore, narrower temperature ranges for a crown temperature are possible. For example, a crown temperature can vary between 1149° C. (2100° F.) and 1316° C. (2300° F.). In addition, a target temperature can be changed for different coking operations. For example, some embodiments of the present technology can maintain a temperature range that is within 100° F. of a first target temperature equal to 2000° F., such that a crown temperature or another coking temperature in a coke oven does not vary by more than 100° F. from 2000° F. during a pyrolysis duration or a pre-determined sub-duration of the pyrolysis duration. Furthermore, other temperature differences or target temperatures are possible for an approximate isothermal pyrolysis duration or sub-duration, where the temperature difference can be less than 200° F. and the target temperature can be a temperature between 1300° F. and 2600° F. For example, the temperature difference can be less than 25° F., 50° F., 100° F., 150° F., or 200° F., and the target temperature can be less than 1850° F., 1950° F., 2050° F., 2200° F., 2400° F., or 2600° F.

Despite variations in the crown temperature, some embodiments of the present technology can regulate a crown temperature and sole flue temperature such that the crown temperature is greater than the sole flue temperature throughout the pyrolysis duration. Some embodiments can achieve this control by actuating an uptake damper that controls flow through an uptake duct or a sole flue damper that controls flow through a sole flue. Some embodiments can control the period between changes in the state of a damper and the specific states of the damper for each respective sub-period of a pyrolysis duration. For example, some embodiments of the present technology can execute a sequence of closing an uptake damper or a sole flue damper from a fully open configuration into a partially closed configuration before reopening the damper into the fully open configuration. In some embodiments, the sequence of damper closure and damper opening operations can be more complex than a simplistic opening and closing operation. For example, some embodiments of the present technology can keep a damper open for a first period, partially close the damper within four hours of closure (e.g., initiate closure operations within two hours of the start of a pyrolysis duration), reopen the damper to a full open configuration, close the damper into a fully closed configuration, reopen the damper to a partially open configuration, fully open the damper into a fully open duration, and then fully close the damper to a fully closed configuration.

In some embodiments, a pyrolysis duration or a coking cycle can be greater than or equal to 12 hours, greater than or equal to 24 hours, greater than or equal to 48 hours, greater than or equal to 72 hours, greater than or equal to 96 hours. In some embodiments, operations to increase the moisture of a coal blend can permit an oven to maintain a longer pyrolysis duration, such as approximately 96 hours, approximately 72 hours, approximately 48 hours or another duration greater than 24 hours. For example, after increasing the moisture of a coal blend as described in block 812, some embodiments of the present technology can be capable of increasing the amount of time that the coal blend is exposed to a coking temperature from 24 hours to 48 hours or more than 48 hours.

Some embodiments can maintain a relatively isothermal temperature profile for a crown temperature during a pyrolysis duration, where a relatively isothermal temperature profile can mean that the crown temperature is within a predefined range that is within 10% or 20% of a median value or average value. For example, some embodiments of the present technology can maintain a crown temperature that satisfies a 50° F. temperature range of 2000° F. during a duration such that the crown temperature is between 1950° F. and 2050° F. during a pyrolysis duration. Alternatively, some embodiments of the present technology can maintain a crown temperature that is within a crown temperature range during a sub-duration of the pyrolysis duration. For example, during a 24 hour pyrolysis duration, some embodiments of the present technology can operate a set of valves to maintain a crown temperature between 2000° F. and 2080° F. for a sub-duration when the pyrolysis duration is at least 12 hours long. The temperature range boundary can include various temperature ranges, such as a 20° F. temperature, 40° F. temperature, or some other value less than 200° F. Furthermore, the temperature range can be centered around a specific value, such as 1900° F., 2000° F., 2100° F., or some other temperature value. Furthermore, some embodiments of the present technology can be pre-configured to use a specific temperature range.

Some embodiments can retrieve a population of coke products from the coke oven, as indicated by block 844. A coke oven can produce a population of coke products that include foundry coke products, egg coke products, and coke breeze. The operations described in this disclosure can result in various favorable properties, dimensions, or other attributes of the population of coke products, for example, a foundry coke product. Some embodiments can control a coke oven to engineer a targeted distribution of coke products among a population of coke products. For example, operations to maintain an approximately isothermal pyrolysis duration such that at least 60.0% of the population is foundry coke product, and at least 20% of the population is breeze product or egg coke products. By using operations that convert a majority of the output of a coking operation to foundry coke products, some embodiments of the present technology can increase the efficiency of downstream foundry operations. Furthermore, as used in this disclosure, an egg coke product can include a coke product that remains after being screened between 2 inches to 4 inches.

As will be discussed elsewhere in this disclosure, some embodiments of the present technology can generate a foundry coke product with advantageous drop shatter properties. Coke products with greater drop shatter survival rates can retain useful product shapes during downstream foundry operations. For example, some embodiments of the present technology can produce a coke product that has a 4-inch drop shatter that is greater than or equal to 80%, where a 4-inch drop shatter indicates the expected fraction of coke products that do not show significant breakage when dropped from a 4-inch height. Similarly, the same coke products or different coke products can have a 2-inch drop shatter that is greater than or equal to 90%, where a drop shatter that is greater than 90% can indicate significant product strength.

As will be discussed elsewhere in this disclosure, some embodiments of the present technology can generate a foundry coke product with advantageous fluidity values. Products with greater drop shatter survival rates can help preserve useful product shapes during downstream foundry operations. For example, some embodiments of the present technology can produce a coke product that has a fluidity that is greater than a fluidity threshold, such as a fluidity that is greater than or equal to 200 ddpm. A greater fluidity can increase the reaction efficiency during downstream foundry operations.

As will be discussed elsewhere in this disclosure, some embodiments of the present technology can generate a foundry coke product with advantageous AFTs and coke products with lesser AFTs. For example, some embodiments of the present technology can produce a coke product that has a fluidity that is greater than a fluidity threshold, such as a fluidity that is greater than or equal to 100 dial divisions per minute (ddpm) greater than or equal to 150 ddpm, or greater than or equal to some other value, 200 ddpm, such as 250 ddpm, 260 ddpm, 270 ddpm, 280 ddpm, 290 ddpm, or within a range of 250-300 ddpm. A greater fluidity can increase the reaction efficiency during downstream foundry operations.

Figure 9:
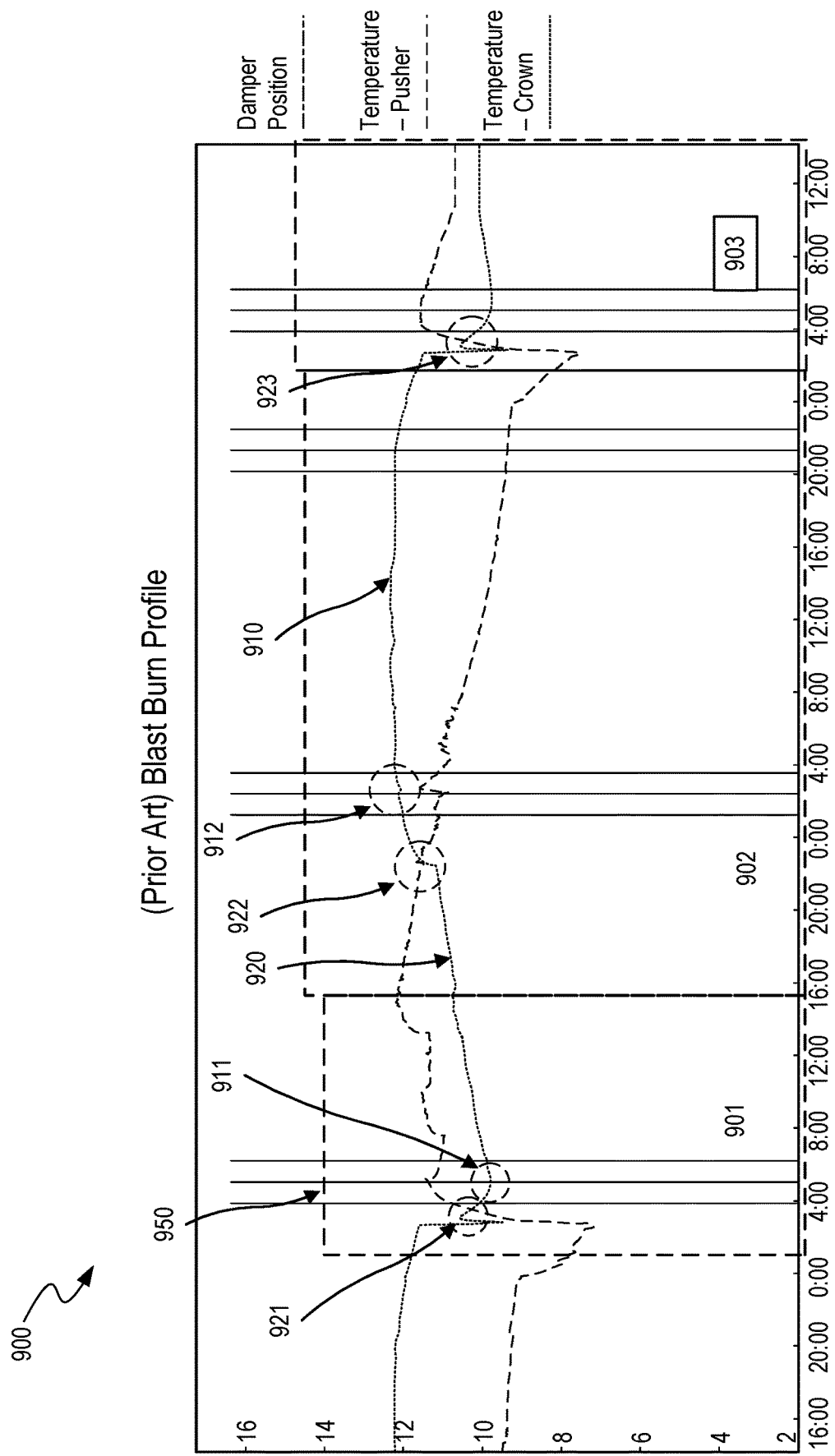
FIG. 9 is a chart showing a burn profile for a blast coke product operation.

FIG. 9 is a chart showing a burn profile for a blast coke product operation. The chart 900 shows blast operations of a coke oven during a coking cycle. A line 950 demonstrates the positions of an uptake damper of the coke oven. As shown in a first sub-duration outlined by a first region 901, the oven damper remains in a fully open state for over 12 hours. As shown by the drop of line 950 at the end of the first sub-duration, the damper can be controlled and positioned into different partially closed states over the next 36 hours, as shown in a second sub-duration outlined in a second region 902. The damper is then fully closed, as shown by the third sub-duration outlined in a third region 903.

As shown by the crown temperature measurement line 910, the crown temperature of the blast coke can vary significantly over time, and can vary by more than 400° F. For example, the crown temperature can be 2004° F. at timepoint 911 and 2449° F. at timepoint 912. Furthermore, relative difference of the crown temperature to an uptake temperature can switch during the coking cycle represented by the chart 900. As seen by the uptake temperature line 920, the uptake temperature is less than the crown temperature until a time represented by the timepoint 921, remains greater than the crown temperature until a time represented by the timepoint 922, and remains less than the crown temperature until a time represented by the timepoint 923. Both the temperature variation in the crown temperature and the repeated switching of relative temperatures can result in inhomogeneities and lower crystallization in any coke products produced by operations represented by the chart 900.

Figure 10:
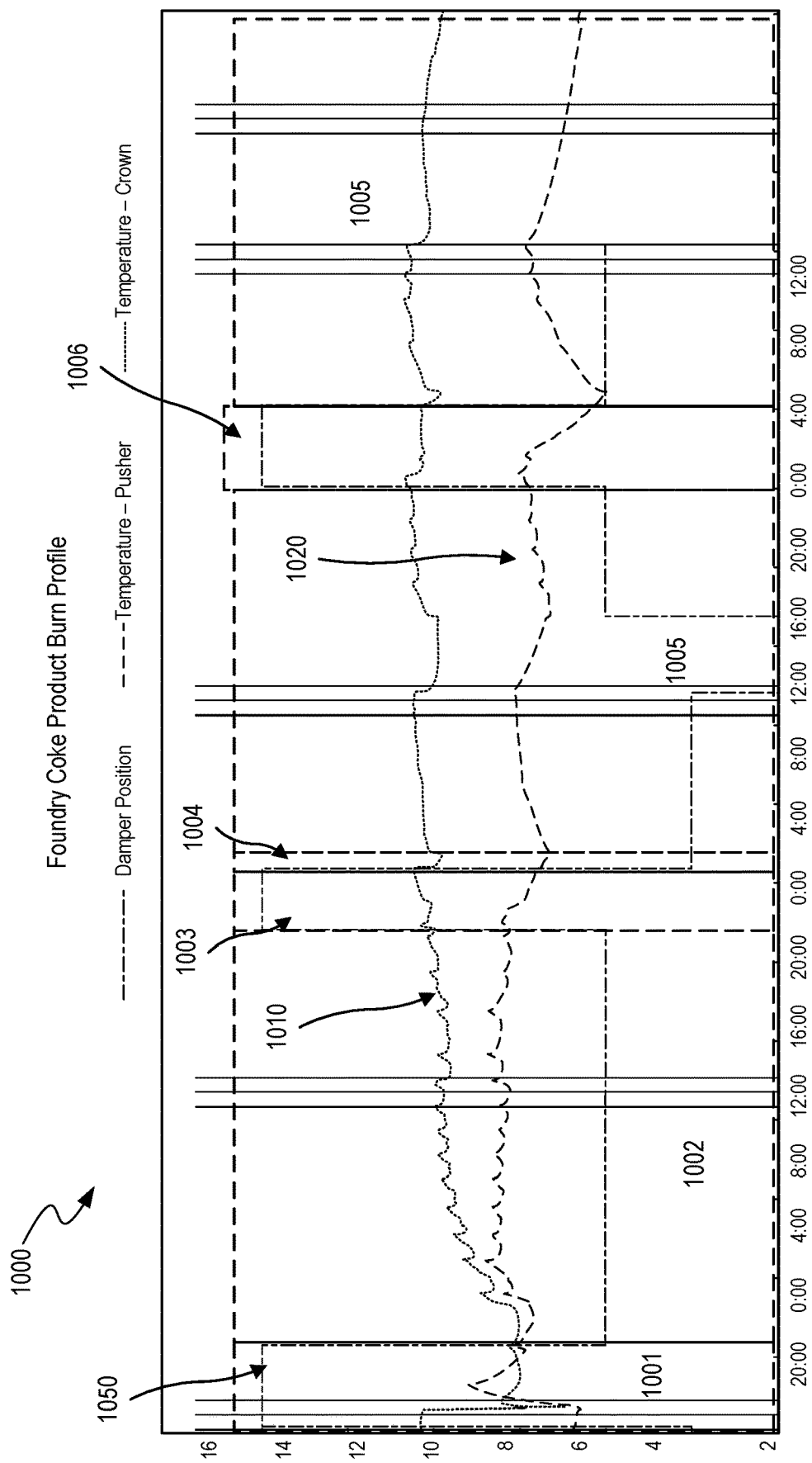
FIG. 10 is a chart showing a burn profile for a foundry coke product operation, in accordance with one or more embodiments of the present technology.

FIG. 10 is a chart showing a burn profile for a foundry coke product operation, in accordance with one or more embodiments of the present technology. The chart 1000 shows foundry coke operations of a coke oven during a coking cycle. A line 1050 demonstrates the positions of an uptake damper of the coke oven. As shown in a first sub-duration outlined by a first region 1001, the oven damper remains in a fully open state for approximately two hours. As shown by the drop of line 1050 at the end of the first sub-duration, the damper can be controlled and positioned into a first partially closed state that is at a closed state greater than 50% closure and held in this state for a second sub-duration represented by a second region 1002.

After an initial closure operation, the damper can be held for a pre-determined period of time (e.g., 10 hours, 20 hours, or another duration greater than 2 hours). Alternatively, or additionally, the damper can be triggered to reopen later based on a temperature measurement. For example, some embodiments of the present technology can detect that the crown temperature represented by the line 1050 satisfies a temperature threshold (e.g., exceeding a maximum value threshold or being less than a minimum value threshold) and, in response, perform an opening operation of the damper. As shown by the times represented by the regions 1003, 1004, 1005, 1006, and 1007, the damper can be repeatedly operated in accordance with a pre-determined schedule or a set of thresholds to open and close the damper, where the opening operation or closure operations can change a damper to a fully open state, partially closed state, or full closed state. The operations shown by the line 1050 to open or close a damper are shown in the chart 1000 to (1) close a damper to a first partially closed state, (2) reopen the damper to a fully open state, (3) close the damper to a second partially closed state, (4) reopen the damper to the fully open state, (5) close the damper to a second partially closed state, (6) close the damper to a fully closed state, (7) reopen the damper to the second partially closed state, (8) reopen the damper to the fully open state, and then (9) close the damper to a fully closed state. However, other sequences of damper operation are possible, such as a closure to a fully closed state at the second sub-duration represented by the second region 1002.

Some embodiments can treat the time at which an oven temperature reaches a lower bound coking temperature threshold to be the start of a pyrolysis duration, during which the bulk of the coking reaction to produce coke products from a coal blend in a coke oven is occurring. Some embodiments can have multiple criteria to determine that the start of a pyrolysis duration has occurred, such as a first criterion requiring that a temperature threshold is reached by a crown temperature and a second criterion requiring that the crown temperature be greater than a sole flue temperature. As can be seen by a comparison of the crown temperature 1010 with the sole flue temperature 1020, the crown temperature can be greater than the sole flue temperatures for the entirety of the pyrolysis duration when implementing a foundry coke product operation. Furthermore, as can be seen in the chart 1000, the crown temperature 1010 can be relatively isothermal with respect to a target temperature of 2100° F. and an allowable temperature difference of 100° F. in the pyrolysis sub-duration represented by the regions 1003-1006. By maintaining this relatively isothermal temperature, some embodiments of the present technology can increase a crystallization efficiency, which can permit more efficient carbon release during a foundry operation.

IV. Foundry Coke Products and Associated Systems, Devices, and Methods

Figure 11:
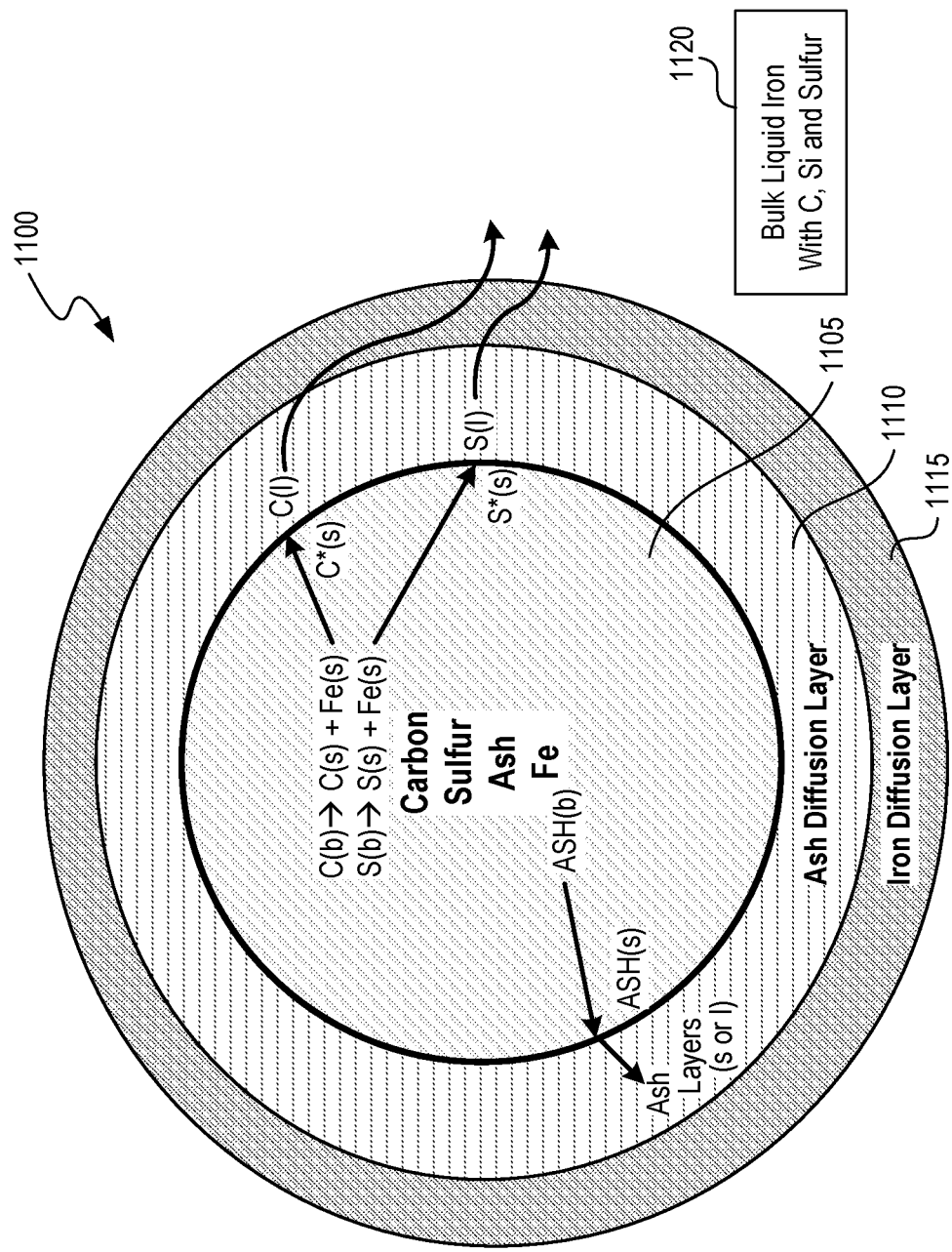
FIG. 11 illustrates a coke particle configured to be heated in a foundry cupola, in accordance with one or more embodiments of the present technology.

FIG. 11 illustrates a coke particle configured to be heated in a foundry cupola, in accordance with one or more embodiments of the present technology. As shown in FIG. 11, C(b)=carbon bulk, S(b)=sulfur bulk, Ash (b)=ash in bulk, C(s)=surface carbon, S(s)=surface sulfur, Ash(s)=surface ash (which builds up from the shrinking core), Fe(s) =surface Fe, C*(s)=active carbon surface, FeC, S*(s)=active sulfur surface, FeS, C(l)=carbon in liquid, and S(l)=sulfur in liquid. The coke particle 1100 includes a core 1105 that shrinks due to carbon dissolution in a cupola, where the coke particle 1100 can be surrounded by a bulk liquid 1120. As the core 1105 of the coke particle 1100 shrinks, e.g., due to oxidation and/or combustion of the carbon of the coke particle 1100, diffusion layers comprising ash and iron that are radially outward of the core 1105 begin to form. For example, the coke particle 1100 can include a first or ash diffusion layer 1110 ("first diffusion layer 1110") comprising ash that is radially outward of the core 1105 and at least partially surrounds the core 1105, and a second or iron diffusion layer 1115 ("second diffusion layer 1115") that is radially outward of the core 1105 and first diffusion layer 1110 and at least partially surrounds the first diffusion layer 1110.

The first diffusion layer 1110 layer can be solid or liquid, and can effectively block the coke surface, or lower the mass transfer area across the coke surface into the surrounding liquid metal. Additionally or alternatively, the first diffusion layer 1110 enables oxidation and/or combustion of the carbon of the coke particle to be time and/or temperature delayed, such that the coke does not produce carbon monoxide in the drying region and instead is oxidized and combusted in the reaction region of the cupola. The first diffusion layer 1110 comprising ash is formed in part due to the ash fusion temperature of the coke product, which is directly correlated to the composition of the coke particle 1100. As described elsewhere herein, the ash fusion temperature of the coke is lower than traditional coke products, and can no more than 2650° F., 2600° F., 2550° F., 2500° F., 2450° F., 2400° F., 2350° F., 2300° F., 2250° F., 2200° F., 2150° F., 2100° F., 2050° F., 2000° F., 1950° F., 1900° F., 1850° F., or within a range of 1800-2600° F., 1800-2500° F., 1900-1300° F., or 2000-2200° F. This relatively low ash fusion temperature can enable formation of the diffusion ash layer, e.g., in the drying region of the cupola, that prevents cooking of the coke, or more particularly the core 1105, prior to the reaction region. Additionally or alternatively, this relatively low ash fusion temperature can optimize contact time between the coke 1100 and the metal within the cupola once the metal melts and becomes molten at the reaction region of the cupola. As a result, more carbon can be transferred from the coke 1100 to the metal. This is in contrast to conventional coke products, which can have a higher ash fusion temperature that results in ash being formed deeper (i.e., downstream) of the reaction region and thus limits the contact time between the coke and the molten metal, thereby resulting in relatively less carbon transfer.

The second diffusion layer 1115 is formed as the coke particle 1100 is heated within the cupola and the coke core 1105 shrinks. The second diffusion layer can further limit cooking of the coke within the drying region and/or help ensure the vast majority of combustion and oxidation of the coke does not occur until the coke 1100 reaches the reaction region. Additionally or alternatively, carbon and sulfur may compete with one another to pass through the second diffusion layer 1115. That is, the presence of sulfur can undesirably decrease the transfer rate of carbon from and out of the coke 1100.

In some embodiments, the coke can be pre-fluxed and/or include (e.g., doped with) an additive (e.g., calcium, iron, calcium oxide, magnesium oxide, iron oxide, sodium oxide, and potassium oxide, and/or other oxides having a relatively low melting point) that acts as a catalytic material. As an example, sodium can act as a pre-fluxing agent, and iron can act as a pre-fluxing and catalytic agent. The catalytic material can trap sulfur and therein be utilized to flux the sulfur out of the coke. In some embodiments, the pre-fluxed coke is a result of selecting coals to produce the coke that have ash materials proportionally higher in the oxides described above. This is in contrast to coke products that may add calcium oxide or calcium carbonate particles/rocks as a flux to remove ash, as such methods are inefficient due to the very low surface to volume ratio for the fluxing to actually occur. Additionally, the pre-fluxed coke and/or catalytic agents can promote the carbon deposition via the Boudouard reaction, thereby generating more heat and increasing the amount of carbon that is present within the reaction region (e.g., the combustion zone) of the cupola. Without being bound by theory, the pre-fluxing agents can alter the liquidis temperature of the slag (e.g., slag 116; FIG. 1) or, more particularly, can alter the liquidis temperature of the ash at the surface or interior of the coke that is blended into the bulk slag.

Improved coke chemistry aims at increasing carbon dissolution from the coke particle 1100 into the metal (i.e., the iron or steel) within the cupola. In operation, as carbon dissolves into the bulk liquid iron within the cupola, the coke core 1105 shrinks and the ash and impurities are built up at the surface. Additionally, carbon and sulfur both dissociate from the surface, which can be aided by catalytic activity of Fe, Ni and other metals. A lower ash melting temperature, represented by an ash fusion temperature (as described elsewhere herein), allows improved ash removal by faster conversion of ash into a liquid phase and reduces ash resistance. Carbon and sulfur diffuse through the thin iron diffusion layer. Additionally, carbon and sulfur are competitive and resistant to dissolving or transferring of each other. As such, a low sulfur content of the coke improves carbon transfer. In addition, coke products having a high coke reactivity index (CRI) or a low coke strength after reaction (CSR) (as described elsewhere herein) allows more reactive carbon forms to dissociate from the surface thereby increasing the carbon dissolution rate.

Various metals added to a foundry coke product produced from a coal blend via ash in the coal blend or otherwise introduced into the foundry coke product can provide catalytic functions that increases a carbon dissolution rate. In some embodiments, a multi-oxidation state element (e.g., a metal) may change oxidation states in a coke product to provide catalytic activity. For example, a coke product may include sodium, which may transition from an unoxidized state Na into a first ionic oxidation state $Na^+$. Alternatively, or additionally, a coke product may include iron, which may transition from an unoxidized state Fe into the oxidized states $Fe^{2+}$ or $Fe^{3+}$. Furthermore, the coke product may include the multi-oxidation state elements in an oxidized form. For example, the coke product may include $Na^+$ in the form of a salt or $Fe^{3+}$ in the form of $Fe_2O_3$. The coke product may also include other types of metals, such as nickel, copper, etc. The catalytic material embedded in the coke product increases carbon dissolution during steel production because at least some of the catalytic material will remain in contact with the interface between the coke product and a liquid iron bath during steel production.

Figure 12:
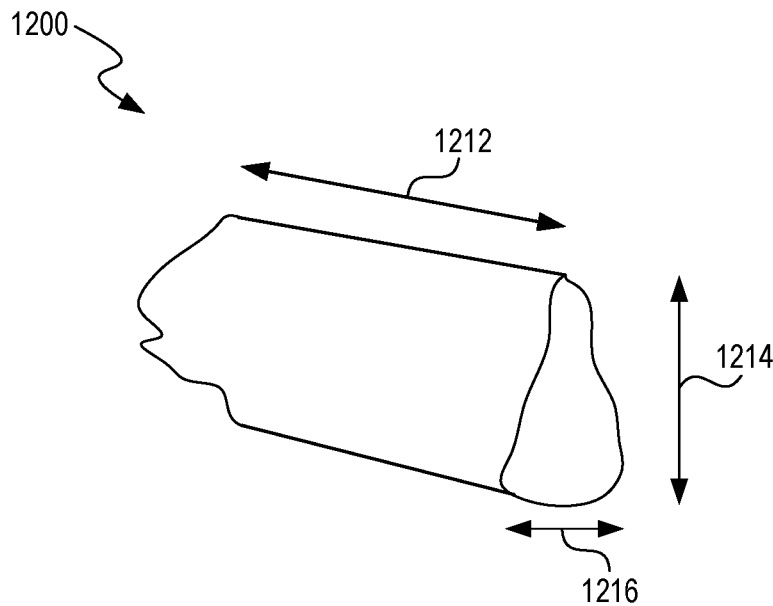
FIG. 12 depicts an example foundry coke product and a table of foundry coke properties, in accordance with one or more embodiments of the present technology.

FIG. 12 depicts an example foundry coke product and a table of foundry coke properties, in accordance with one or more embodiments of the present technology. Some embodiments can use a coke oven, such as the oven 200 of FIG. 2, to produce a foundry coke product 1200. In some embodiments, the foundry coke product 1200 can be generally oblong shaped and can have different or similar dimensions along a first length 1212, a second length 1214, or a third length 1216. For example, the first length 1212 can be greater than 6.0 inches (e.g., 9.0 inches), the second length can be greater than 2.5 inches (e.g. 4.0 inches), and the third length can be greater than 2.5 inches (e.g., 4.0 inches). In some embodiments, one or more lengths of the shape of the foundry coke product 1200 can be limited to a maximum value. For example, the first length 1212 can be between 6.0 inches and 12.0 inches.

Due to variations in the specific shape of foundry coke products, a foundry coke product can be characterized by a range of hydraulic diameters. For example, the foundry coke product 1200 can have a hydraulic diameter that is greater than or equal to 1.0 inches, greater than or equal to 2.0 inches, or greater than or equal to 3.0 inches, etc. In some embodiments, the hydraulic diameter of a foundry coke product can be greater than an actual diameter of the foundry coke product due to the cross-sectional geometry of the foundry coke product.

The table 1250 includes a set of attributes of the foundry coke product 1200. The attributes of foundry coke products shown in the table 1250 can characterize coke products produced by the operations described in this disclosure. Such attributes can be advantageous for foundry operations, such as having lower AFT values in comparison to conventional coke products. Such lower AFT values can be represented in various forms, such as the IDT or ST values. For example, sample "S4" shown in the table 1250 has an ash fusion IDT equal to 2150° F. (1177° C.). Some embodiments can perform operations to reduce a low ash fusion to a coke product based on an AFT threshold or target ash fusion range.

In some embodiments, a target AFT value or AFT range can vary based on the type of ash fusion value being used. In some embodiments, a produced coke product can have an IDT that is between 2100° F. and 2400° F. Some embodiments can include stricter limits on coke products. For example, some embodiments of the present technology can include a coke product having an IDT that is between 2100° F. (1149° C.) and 2250° F. (1232° C.). Some embodiments can change coal blends, soak times, or durations at different damper positions to satisfy a target IDT. For example, some embodiments of the present technology can select a coal blend or determine oven operations based on a target IDT value of approximately 2100° F., approximately 2150° F., approximately 2200° F., approximately 2250° F., approximately 2300° F., approximately 2350° F., or approximately 2400° F. In some embodiments, a soak time can be established as starting after a peak crown temperature or other peak temperature is reached. Alternatively, a soak time can be established as starting after a sole flue temperature or crown temperature begins decreasing without any gas flow. Furthermore, the soak time can be reduced due to the increased coking time of a pyrolysis duration, where the soak time can be less than 10.0 hours, less than 5.0 hours, or even less than 1.0 hour. Furthermore, some embodiments of the present technology can use various total cycle times, and can characterize an operation based on a ratio of a soak time to a pyrolysis duration, where the ration can be less than 33.0%, less than 15.0%, less than 5.0%, or less than some other threshold that is less than 50%.

Similarly, some embodiments of the present technology can produce coke products using operations described in this disclosure having an ST that is within a specified range, such as between 2150° F. and 2500° F. Some embodiments can implement operations that satisfy a stricter range for an ST, such as modifying operations to produce coke products having an ST between 2150° F. and 2300° F. Furthermore, some embodiments of the present technology can change coal blends, soak times, or durations at different damper positions to satisfy a target ST. For example, some embodiments of the present technology can select a coal blend or determine oven operations based on a target ST value of approximately 2100° F., approximately 2150° F., approximately 2200° F., approximately 2250° F., approximately 2300° F., approximately 2350° F., approximately 2400° F., approximately 2450° F., or approximately 2500° F. Furthermore, some embodiments of the present technology can set a target IDT value as a function of a target ST value.

Similarly, some embodiments of the present technology can produce coke products using operations described in this disclosure having an HT that is within a specified range, such as between 2200° F. and 2350° F. Some embodiments can implement operations that satisfy a stricter range for an HT, such as modifying operations to produce coke products having an HT between 2150° F. and 2300° F. Furthermore, some embodiments of the present technology can change coal blends, soak times, or durations at different damper positions to satisfy a target HT. For example, some embodiments of the present technology can select a coal blend or determine oven operations based on a target HT value of approximately 2200° F., approximately 2250° F., approximately 2300° F., approximately 2350° F., approximately 2400° F., approximately 2450° F., or approximately 2500° F.

Similarly, some embodiments of the present technology can produce coke products using operations described in this disclosure having an FT that is within a specified range, such as an FT between 2250° F. and 2600° F. Some embodiments can implement operations that satisfy a stricter range for an FT, such as modifying operations to produce coke products having an FT between 2250° F. and 2400° F. Furthermore, some embodiments of the present technology can change coal blends, soak times, or durations at different damper positions to satisfy a target FT. For example, some embodiments of the present technology can select a coal blend or determine oven operations based on a target FT value of approximately 2250° F., approximately 2300° F., approximately 2350° F., approximately 2400° F., approximately 2450° F., approximately 2500° F., approximately 2550° F., or approximately 2600° F.

Some embodiments can produce coke products that satisfy multiple target ranges for different types of AFT values. For example, some embodiments of the present technology can include a coke product having an IDT between 2100° F. and 2250° F., an ST between 2150° F. and 2300° F., an HT between 2200° F. and 2350° F., or an FT between 2250° F. and 2400° F. Alternatively, or additionally, various other combination of target ranges for a coke product are possible. For example, some embodiments of the present technology can include a coke product having an IDT between 2100° F. and 2250° F., an ST between 2150° F. and 2300° F., an HT between 2200° F. and 2350° F., and an FT between 2250° F. and 2400° F.

Some embodiments can generate coke products having AFTs that are within various composition boundaries to satisfy an AFT value. For example, some embodiments produce coke products having an AFT that is greater than 2300° F. or less than 2600° F. Some embodiments can include stricter tolerances for the production or selection of coke products for downstream use, such as being between 1800° F. and 2600° F., between 2200° F. and 2500° F., between 2300° F. and 2400° F., between 2400° F. and 2600° F., or between 2500° F. and 2600° F.

Some embodiments can use operations described in this disclosure to produce a coke product characterized by specific types of AFT values. For example, some embodiments of the present technology can produce a coke product having an AFT ST between 982° C. (1800° F.) and 1427° C. (2600° F.), 1177° C. (2150° F.) and 1371° C. (2500° F.) or a coke product having an AFT HT between 1204° C. (2200° F.) and 1371° C. (2500° F.), or an AFT flow temperature (FT) between 1232° C. (2250° F.) and 1371° C. (2500° F.).

As shown in the table 1250, the CRI value of the foundry coke products can be 36.5% or another value that is greater than 35%. Some embodiments can implement coke production operations that produce batches of foundry coke that satisfy one or more CRI thresholds. For example, some embodiments of the present technology can change durations between changes in damper configurations or select between different damper positions based on a CRI threshold. For example, some embodiments of the present technology can produce foundry having a CRI that is at least 25.0%, at least 30.0%, at least 35.0%, at least 40.0%, at least 45.0%, or another value that is at least 30.0%. Some embodiments can perform operations to select coke products that have CRI greater than a minimum CRI threshold for downstream use. In some embodiments, a CRI for a coke product may indicate a mass loss from a reaction, where a greater CRI for a coke product may indicate a greater efficiency or usefulness of the coke product. In some embodiments, the CRI may be computed using a model based on known properties of a coke product or the coal blend used to generate the coke product. Alternatively, or additionally, a CRI may be experimentally obtained as a measured weight loss using an established testing protocol. For example, some embodiments may use a CRI-measuring method such as the ASTM method D5341 to determine a CRI value.

As shown in the table 1250, the CSR value of the foundry coke products can be 26%, 15.6%, or another value that is greater than a CSR threshold such as 7.0%. Some embodiments can implement coke production operations that produce batches of foundry coke that satisfy one or more CSR thresholds. For example, some embodiments of the present technology can change durations between changes in damper configurations or select between different damper positions based on satisfying a target CSR threshold, such as a CSR threshold requiring that foundry coke have a CSR that is less than or equal to 40.0%, less than or equal to 35.0%, less than or equal to 30.0%, less than or equal to 25.0%, less than or equal to 20.0%, less than or equal to 15.0%, less than or equal to 10.0%, or less than or equal to 7.0%.

As shown in the table 1250, an $SiO_2$ composition in coke product ash can include 49.4%, 48.9%, 48.8%, 49.1%, or 46.0%. Other embodiments can include other $SiO_2$ mass fractions in ash, such as other values less than 70%, less than 50.0%, less than 45.0%, etc. In some embodiments, a mass fraction of approximately 50.0% $SiO_2$ in coke product ash can correspond with a low amount of $SiO_2$ in the coke product itself.

Furthermore, some embodiments of the present technology can generate coke products having a fixed carbon content (e.g., a fixed carbon mass fraction) that is greater than or equal to a fixed carbon threshold. For example, some embodiments of the present technology can produce foundry coke products having a fixed carbon mass fraction that is greater than 80.0%, 85.0%, 90.0%, 90.5%, 91.0%, or some other value. In some embodiments, the fixed carbon content can be a targeted range. For example, some embodiments of the present technology can perform a set of operations to generate coke products having a fixed carbon content that is less than or equal to 94.5% but greater than or equal to 85.0% (though other ranges of values are possible) such as between 94.5% and 85.0%. Various other target ranges are possible, such as coke products having a range between 90.0% and 95.0%, 85% and 99%, etc.

Furthermore, some embodiments of the present technology can generate coke products having an ash mass fraction within a targeted bounded or unbounded range. For example, some embodiments of the present technology can produce foundry coke products having an ash mass fraction that is greater than or equal to 1.0%, 5.0%, 8.0%, 9.0%, 10.0%, or a value greater than 10.0%. Furthermore, some embodiments of the present technology can include an upper bound to an ash mass fraction. For example, some embodiments of the present technology can produce foundry coke products having an ash mass fraction that is less than 1.0%, 5.0%, 9.0%, 10.0%, or a value greater than 10.0%. Some embodiments can combine these upper and lower limits of ash mass fractions such that a produced coke product has a range of 5.0% to 10.0%, 8.5% to 9.0%, 8.0% to 10.0%, 5.0% to 15.0%, etc.

Figure 13:
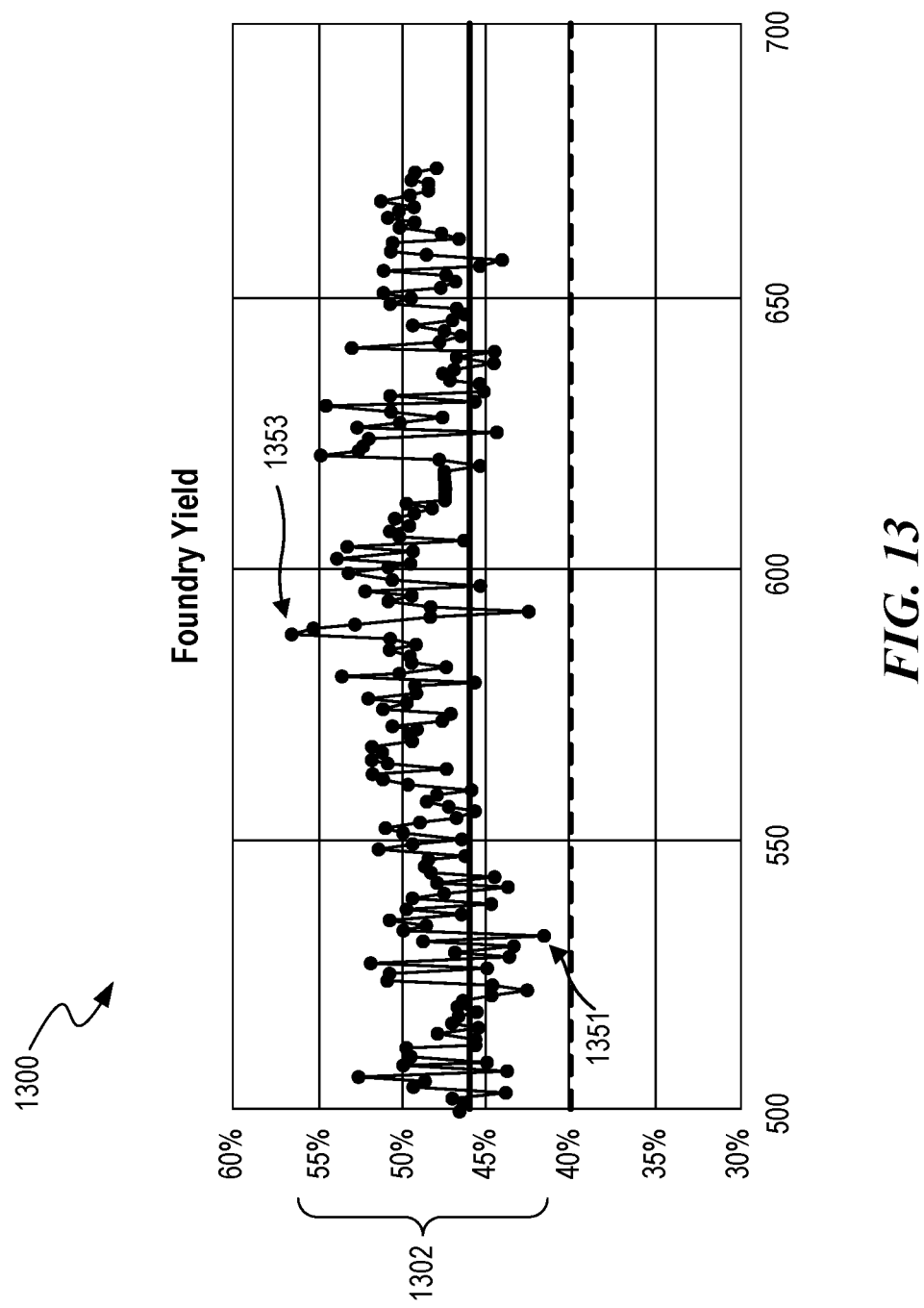
FIG. 13 is a chart indicating foundry coke product yield in accordance with one or more embodiments of the present technology.

FIG. 13 is a chart indicating foundry coke product yield in accordance with one or more embodiments of the present technology. As shown in the chart 1300, the foundry yield for different batches of coke products produced from a coal blend using operations described in this disclosure can vary. As shown by the range 1302, the yield can range between approximately 40% and 60% in some embodiments, where this yield can be a dry yield (i.e., the dry mass fraction of foundry coke product can be 40% or 60% of the dry mass fraction of the total population of coke products). As shown by the data point 1353, some embodiments perform operations that result in a yield that is approximately 57%, though the yield can be lower in other cases. For example, as shown by the data point 1351, the yield in some coke production operations can be lower, such as being as low as 41%. In many cases, some embodiments of the present technology can implement operations that satisfy a minimum yield threshold, such as operations that result in a yield that is at least 25%, at least 30%, at least 40%, at least 50%, at least 60%, etc. While some embodiments of the present technology can implement controller optimization operations to increase a yield, some embodiments of the present technology can permit a predicted yield to be less than an expected maximum yield in order to satisfy other target coke product parameters.

Figure 14:
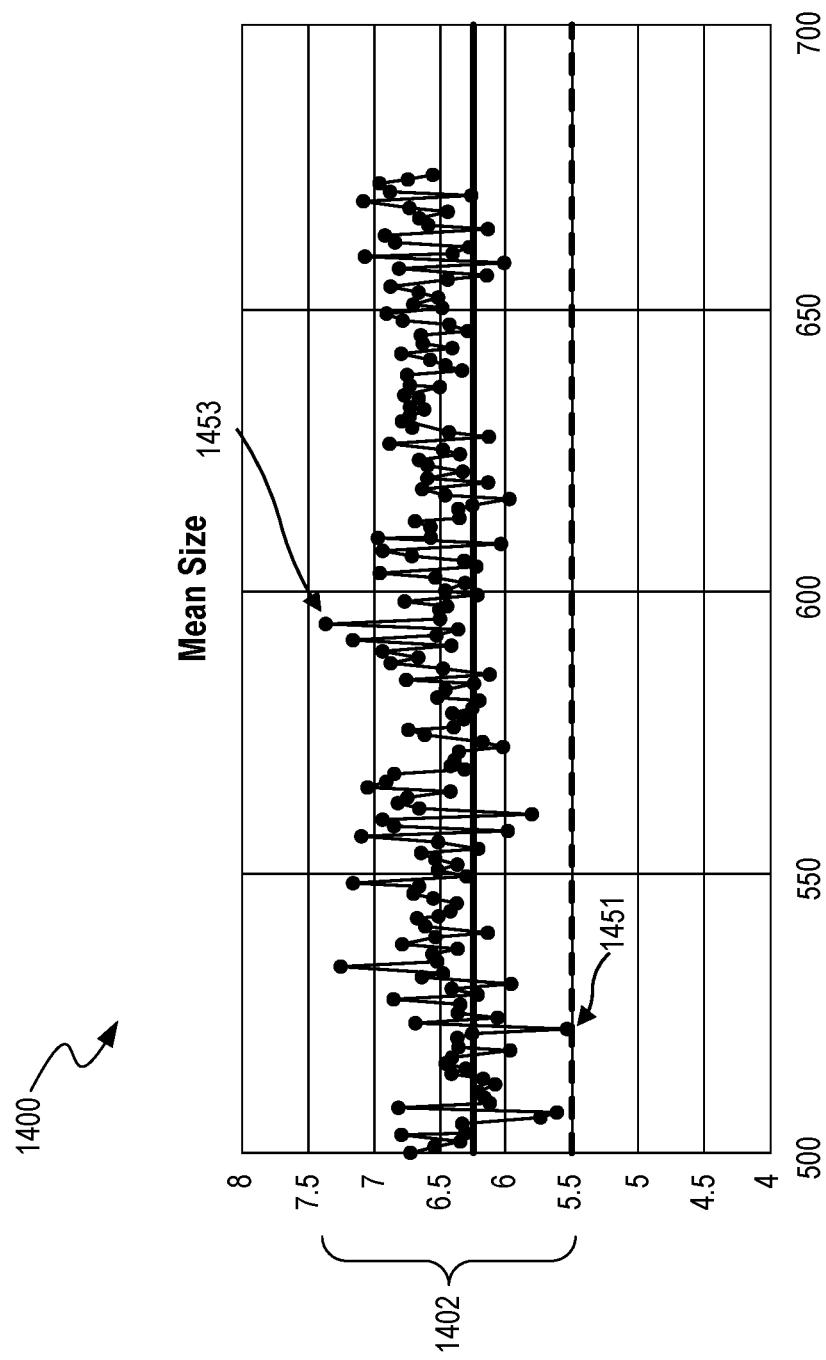
FIG. 14 is a chart indicating particle size, in accordance with one or more embodiments of the present technology.

FIG. 14 is a chart indicating particle size, in accordance with one or more embodiments of the present technology. As shown in the chart 1400, the mean batch lengths in inches for different batches of coke products produced from a coal blend using operations described in this disclosure can vary. As shown by a range 1402, the coke product mean length can range between approximately 5.5 inches to approximately 7.5 inches in some embodiments. As shown by a data point 1453, some embodiments perform operations that result in a coke product mean length that is approximately 7.4 inches, though the coke product mean length can be lower in other cases. For example, as shown by a data point 1451, the coke product mean length in some coke production operations can be lower, such as being as low as 5.5 inches. In many cases, some embodiments of the present technology can implement operations that satisfy a minimum coke product mean length threshold, such as operations that result in a coke product mean length that is at least 2.5 inches, 4.0 inches, 5.0 inches, 6.0 inches, 7.0 inches, 8.0 inches, 9.0 inches, or some other length. In some embodiments, a larger coke product can result in more efficient foundry operations as a result. While some embodiments of the present technology can implement controller optimization operations to increase a coke product mean length, some embodiments of the present technology can permit a predicted coke product mean length to be less than an expected maximum coke product mean length in order to satisfy other target coke product parameters.

Figure 15:
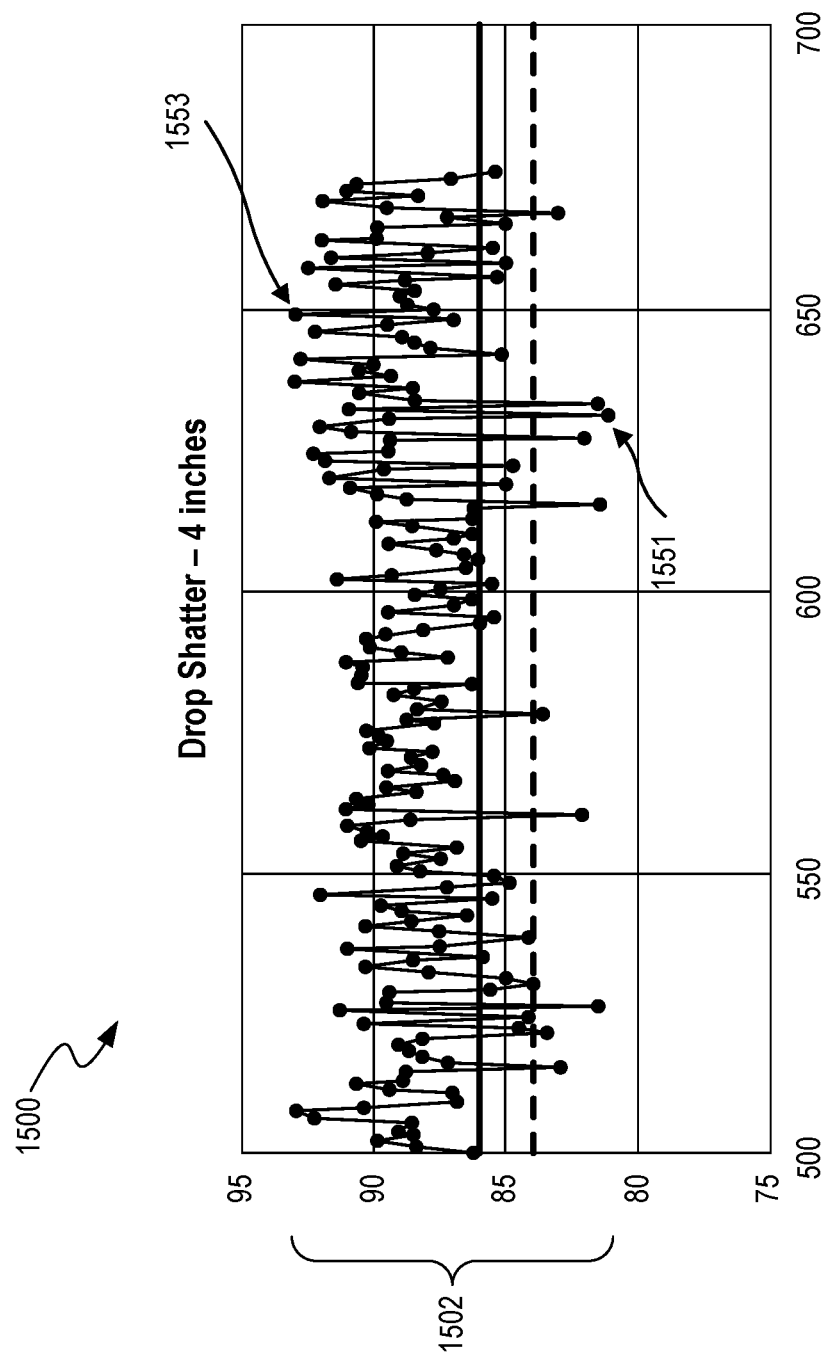
FIG. 15 is a chart indicating 4-inch drop shatter properties, in accordance with one or more embodiments of the present technology.

FIG. 15 is a chart indicating 4-inch drop shatter properties, in accordance with one or more embodiments of the present technology. As shown in the chart 1500, the 4-inch drop shatter survival rates for different batches of coke products produced from a coal blend using operations described in this disclosure can vary. As shown by a range 1502, the 4-inch drop shatter survival rate can range between approximately 80% to approximately 95% in some embodiments. As shown by a data point 1553, some embodiments perform operations that result in a 4-inch drop shatter survival rate that is approximately 93%, though the 4-inch drop shatter survival rate can be lower in other cases. For example, as shown by a data point 1551, the 4-inch drop shatter survival rate in some coke production operations can be lower, such as being as low as 81%. In many cases, some embodiments of the present technology can implement operations that satisfy a minimum 4-inch drop shatter survival rate threshold, such as operations that result in a 4-inch drop shatter survival rate that is at least 80%, at least 85%, at least 90%, or at least 95%, or at least some other 4-inch drop shatter threshold. In many cases, a greater drop shatter survival rate is useful for downstream foundry operations because more coke products survive transportation and downstream processing.

Figure 16:
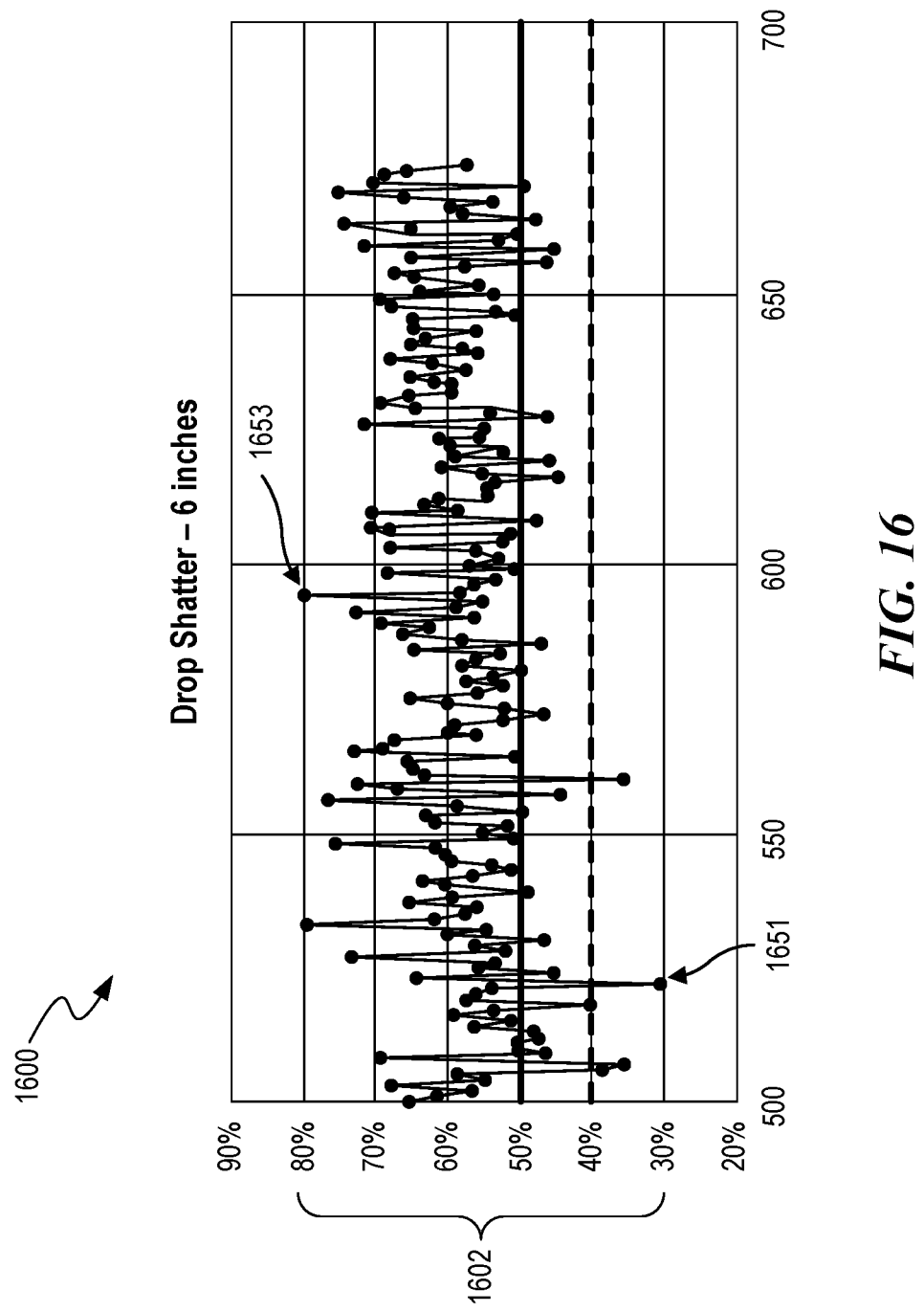
FIG. 16 is a chart indicating 6-inch drop shatter properties, in accordance with one or more embodiments of the present technology.

FIG. 16 is a chart indicating 6-inch drop shatter properties, in accordance with one or more embodiments of the present technology. As shown in the chart 1600, the 6-inch drop shatter survival rates for different batches of coke products produced from a coal blend using operations described in this disclosure can vary. As shown by a range 1602, the 6-inch drop shatter survival rate can range between approximately 30% to approximately 80% in some embodiments. As shown by a data point 1653, some embodiments perform operations that result in a 6-inch drop shatter survival rate that is approximately 80%, though the 6-inch drop shatter survival rate can be lower in other cases. For example, as shown by a data point 1651, the 6-inch drop shatter survival rate in some coke production operations can be lower, such as being as low as 30%. In many cases, some embodiments of the present technology can implement operations that satisfy a minimum 6-inch drop shatter survival rate threshold, such as operations that result in a 6-inch drop shatter survival rate that is at least 60%, at least 70%, at least 80%, or at least some other 6-inch drop shatter threshold, where the 6-inch drop shatter threshold can be less than a 4-inch drop shatter threshold.

Figure 17:
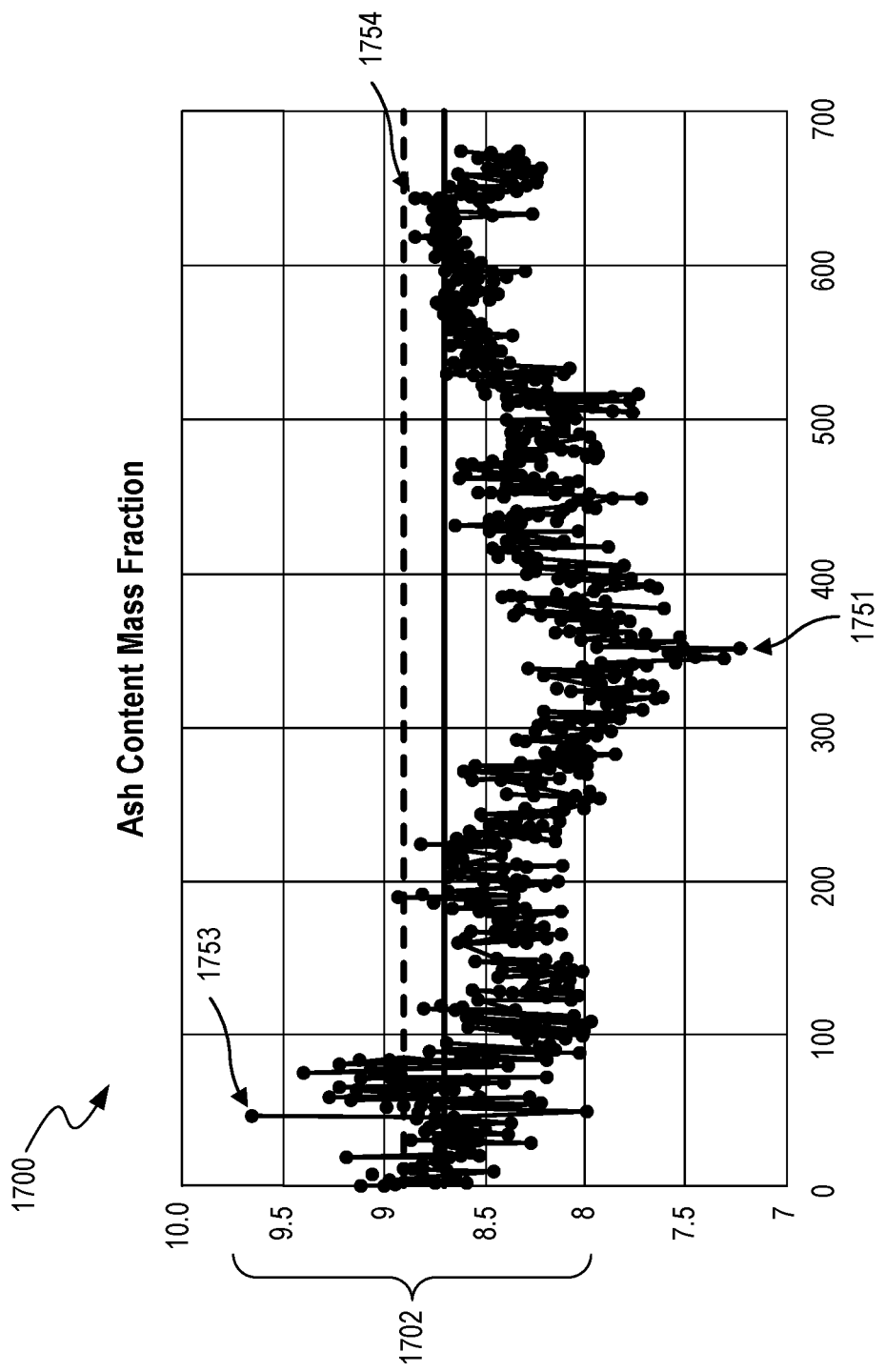
FIG. 17 is a chart indicating an ash mass fraction, in accordance with one or more embodiments of the present technology.

FIG. 17 is a chart indicating an ash mass fraction, in accordance with one or more embodiments of the present technology. As shown in the chart 1700, the ash mass fractions for different batches of coke products produced from a coal blend using operations described in this disclosure can vary. As shown by a range 1702, the ash mass fraction can range between approximately 7% to approximately 10% in some embodiments. As shown by a data point 1753, some embodiments perform operations that result in an ash mass fraction that is approximately 9.7%, though the ash mass fraction can be lower in other cases. For example, as shown by a data point 1754, the ash mass fraction in some coke production operations can be 8.8%. Additionally, or alternatively, as shown by the data point 1751, the ash mass fraction in some coke production operations can be lower, such as being as low as 7.2%.

In some embodiments, an ash content of a coke product produced using operations described in this disclosure can be less than an ash mass fraction threshold, where the ash mass fraction threshold can be 10.0%, 9.0%, 8.5%, 8.0%, 7.5%, or another value less than 50.0%. In some embodiments, the ash mass fraction can be unconventionally high, such as greater than 10.0%. Alternatively, or additionally, some embodiments of the present technology can produce a coke product having an ash mass fraction threshold that satisfies an ash mass fraction threshold that is less than 10.0%, less than 9.0%, less than 8.5%, less than 8.0%, less than 7.5%, or less than 7.0%. Some embodiments can include ash within a range, such as between 5.5% and 7.0%, 6.0% and 6.5%, between 8.0% and 10.0%, or between some other values. Furthermore, some embodiments of the present technology can produce a set of coke products that satisfies a target mass fraction value. For example, some embodiments of the present technology can produce a coke product having an ash mass fraction that satisfies a target ash mass fraction, where the target ash mass fraction can be approximately 9.0%, approximately 8.5%, approximately 8.0%, approximately 7.5%, or approximately 7.0%.

In some embodiments, some embodiments of the present technology can implement operations that produce coke products which satisfies a minimum ash mass fraction threshold, such as coke products having an ash mass fraction that is at least 7.0%, at least 8.0%, at least 9.0%, or at least some other ash mass fraction. Furthermore, some embodiments of the present technology can determine coal blend formulations or perform coke oven operations that have an ash mass fraction that is within a pre-defined range, such as between 7.0% and 10.0%.

Figure 18:
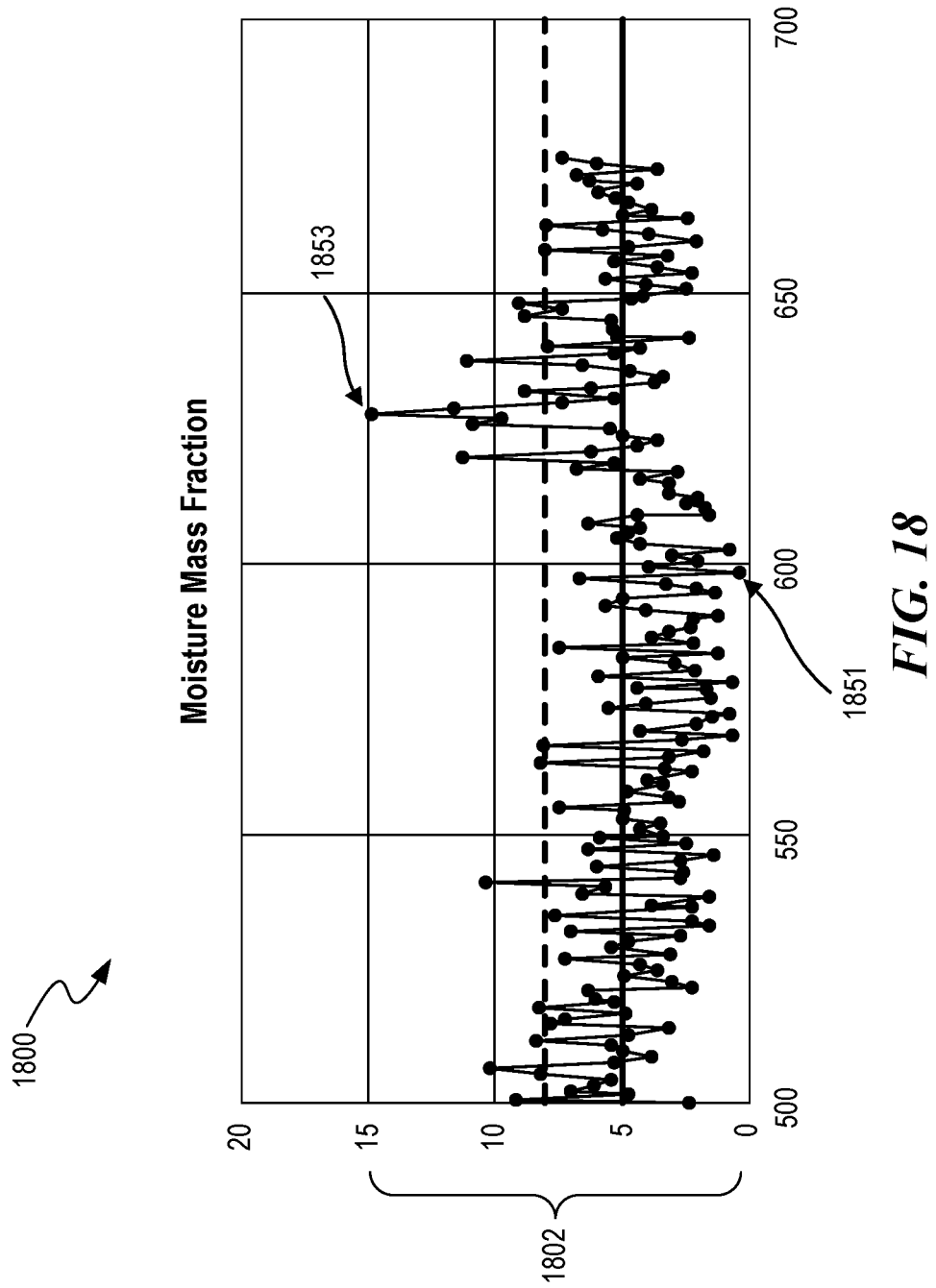
FIG. 18 is a chart indicating a moisture mass fraction, in accordance with one or more embodiments of the present technology.

FIG. 18 is a chart indicating a moisture mass fraction, in accordance with one or more embodiments of the present technology. As shown in the chart 1800, the coke product moisture mass fractions for different batches of coke products produced from a coal blend using operations described in this disclosure can vary. As shown by a range 1802, the coke product moisture mass fractions can range between approximately 0% to approximately 15% in some embodiments. As shown by the data point 1853, some embodiments perform operations that result in a coke product moisture mass fraction that is approximately 15%, though the coke product moisture mass fraction can be lower in other cases. Additionally, as shown by the data point 1851, the coke product moisture mass fraction in some coke production operations can be lower, such as being as low as 0.5%. In many cases, some embodiments of the present technology can implement operations that satisfy a minimum coke product moisture mass fraction threshold, such as operations that result in a coke product moisture mass fraction that is at least 7.0%, at least 8.0%, at least 9.0%, or at least some other coke product moisture mass fraction. Furthermore, some embodiments of the present technology can determine coal blend formulations or perform coke oven operations that have a coke product moisture mass fraction that is within a pre-defined range, such as between 7.0% and 10.0%. Furthermore, some embodiments of the present technology can determine coal blend formulations or perform coke oven operations that have a coke product moisture mass fraction that is less than a pre-defined value, such as less than or equal to 10.0%, less or equal to 8.0%, less than or equal 7.0%, less than or equal to 5.0%, etc.

Figure 19:
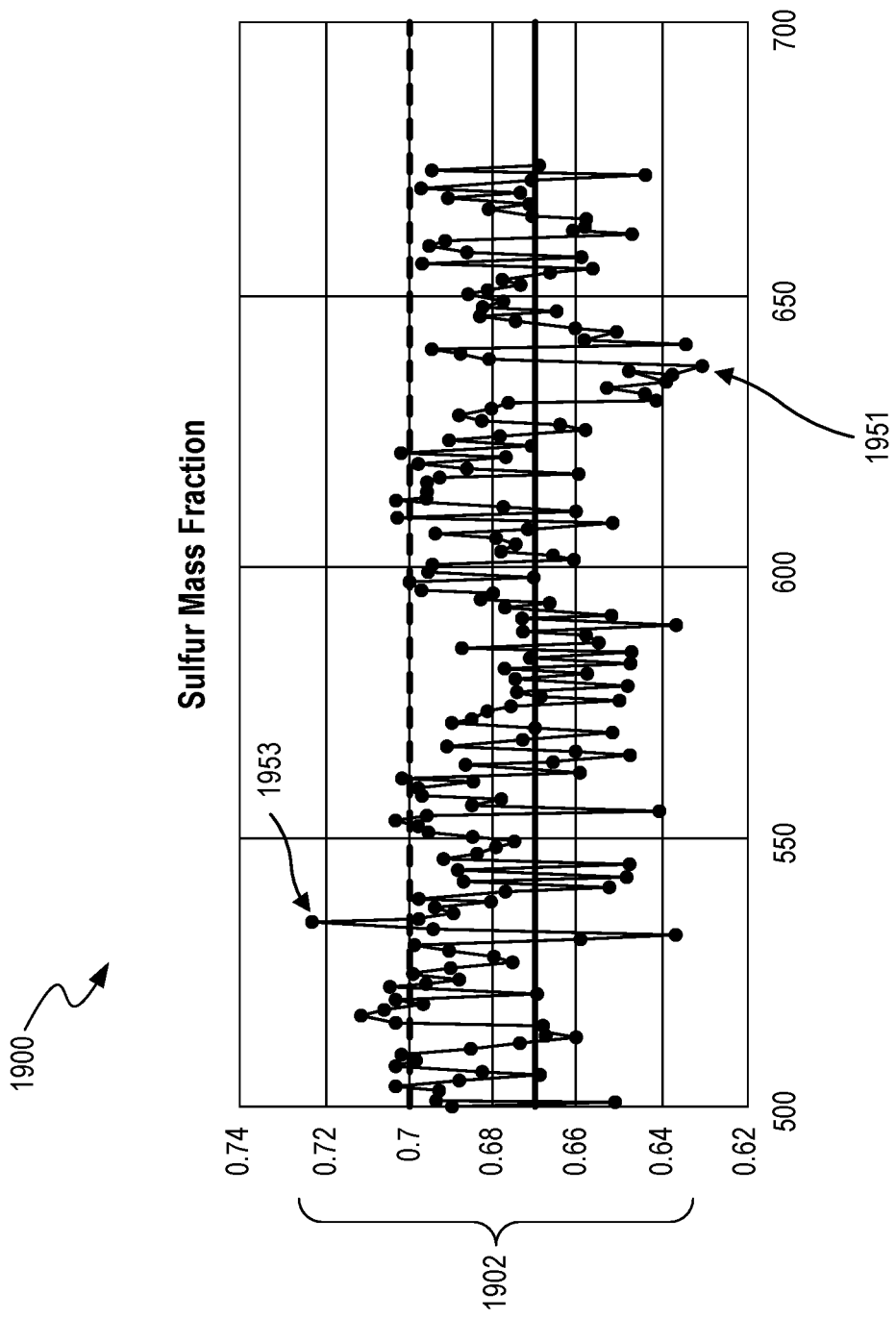
FIG. 19 is a chart indicating a sulfur mass fraction, in accordance with one or more embodiments of the present technology.

FIG. 19 is a chart indicating a sulfur mass fraction, in accordance with one or more embodiments of the present technology. As shown in the chart 1900, the sulfur mass fractions for different batches of coke products produced from a coal blend using operations described in this disclosure can vary. As shown by a range 1902, the sulfur mass fractions can range between approximately 0.60% to approximately 0.75% in some embodiments. As shown by a data point 1953, some embodiments perform operations that result in a sulfur mass fraction that is approximately 0.73%, though the sulfur mass fraction can be lower in other cases. Additionally, as shown by the data point 1951, the sulfur mass fraction in some coke production operations can be lower, such as being as low as 0.63%.

In some embodiments, the sulfur content of the coke product can be less than a sulfur mass fraction threshold. For example, the sulfur content of a coke product can be less than 1.0%, less than 0.9%, less than 0.8%, less than 0.7%, less than 0.6%, less than 0.5%, less than 0.3%, less than 0.2%, or less than 0.1%. Some embodiments determine the formulation of a coal blend, determine a soak time, or determine a damper control schedule to reduce the amount of sulfur in a coke product. Furthermore, a coke product can be produced based on a target sulfur content value, such as a target sulfur mass fraction of 0.65%. As described elsewhere, by reducing the sulfur content of coke products, some embodiments of the present technology can enhance the efficiency of foundry operations.

Figure 20:
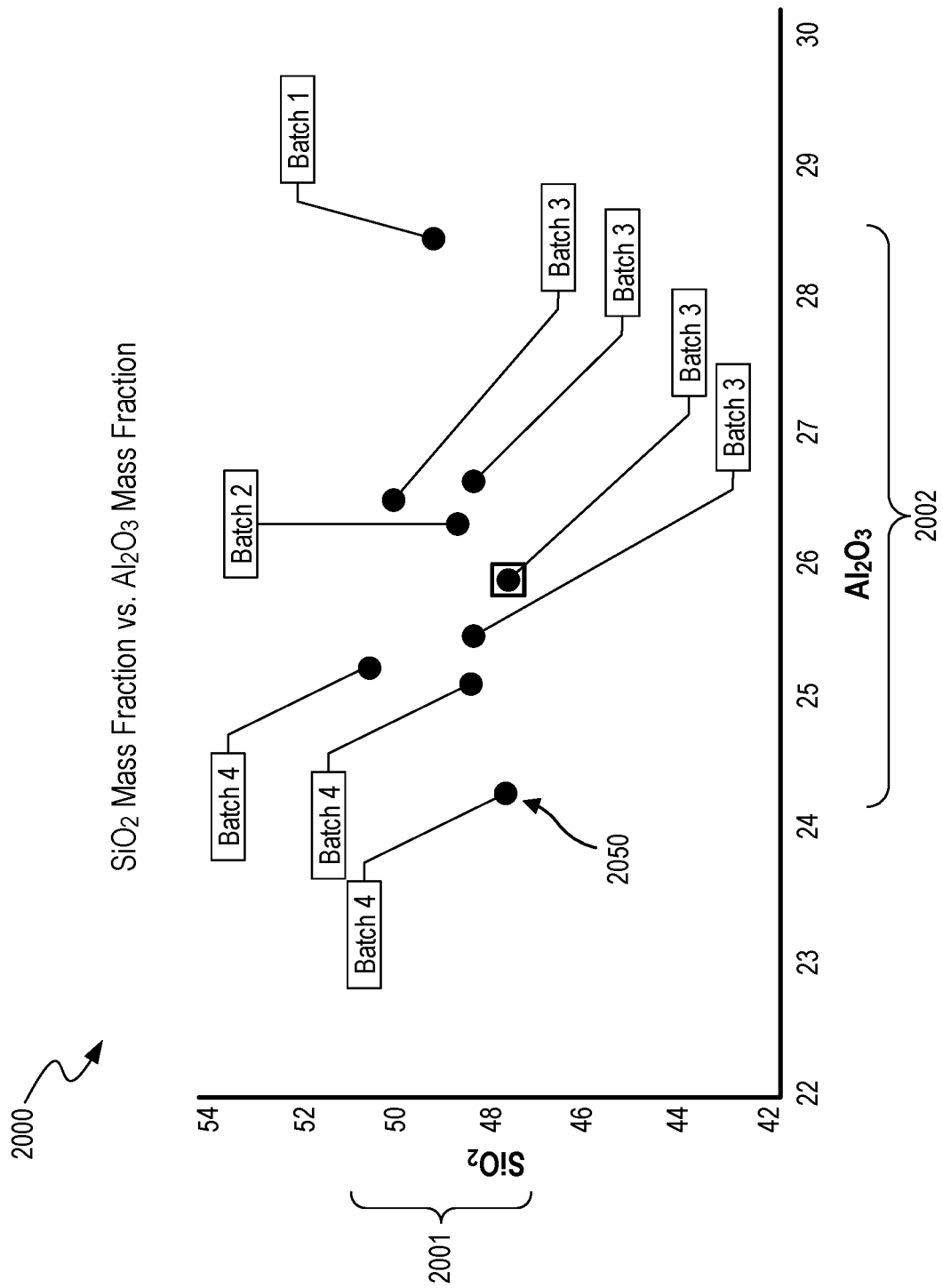
FIG. 20 is a chart depicting $SiO_2$ mass fractions vs. $Al_2O_3$ mass fractions in the ash of foundry coke products, in accordance with one or more embodiments of the present technology.

FIG. 20 is a chart depicting SiO 2 mass fractions vs. $Al_2O_3$ mass fractions in the ash of foundry coke products, in accordance with one or more embodiments of the present technology. In some embodiments, a coke product can be characterized based on their mass fractions of $SiO_2$ and $Al_2O_3$ or ratios of these mass fractions. As shown in the chart 2000, different samples of coke ash can indicate different mass fractions or mass fraction ratios of $SiO_2$ and $Al_2O_3$. For example, the point 2050 indicates a sample having an $SiO_2$ mass fraction of approximately 48.0% and an $Al_2O_3$ mass fraction of approximately 24.3%, which suggests that some ash of coke products can have a ratio of approximately 2:1 for a mass fraction ratio of $SiO_2$ to $Al_2O_3$. As indicated by the range 2001, the $SiO_2$ mass fractions of different samples can range between 48.0% and 51.0% in some embodiments. Furthermore, as indicated by the range 2002, the $SiO_2$ mass fractions of different samples can range between 24.3% and 28.4% in some embodiments.

Some embodiments can produce a coke product that minimizes the combination of $Al_2O_3$ and $SiO_2$ or has a low amount of $Al_2O_3$ and $SiO_2$. For example, some embodiments of the present technology can perform operations that produce coke products such that the ash of the coke products have a combined $Al_2O_3$ mass fraction and $SiO_2$ mass fraction of that is less than or equal to 65%. By reducing the amount of Al and Si in a coke product, some embodiments of the present technology can increase the efficiency of foundry operations by reducing their interference with carbon dissolution during foundry operations.

Some embodiments can produce a coke product or a coal blend used to produce the coal blend that satisfy other thresholds for $Al_2O_3$ or $SiO_2$. For example, some embodiments of the present technology can produce a coke product such that an $Al_2O_3$ mass fraction of the ash of the coke product, or an ash of a coal blend used to create the coke product, is less than or approximately 30%, less than or approximately 25%, or less than or approximately 20%.

Alternatively, or additionally, some embodiments of the present technology can produce a coke product such that an $SiO_2$ mass fraction of the ash of the coke product or an ash of a coal blend used to create the coke product is less than or approximately 50%, less than or approximately 45%, less than or approximately 40%, or less than or approximately 35%.

Alternatively or additionally, some embodiments of the present technology can produce a coke product such that a sum of a $SiO_2$ mass fraction and $Al_2O_3$ mass fraction of an ash of the coke product or an ash of a coal blend used to create the coke product is less than or approximately 80%, less than or approximately 75%, less than or approximately 70%, less than or approximately 65%.

Figure 21:
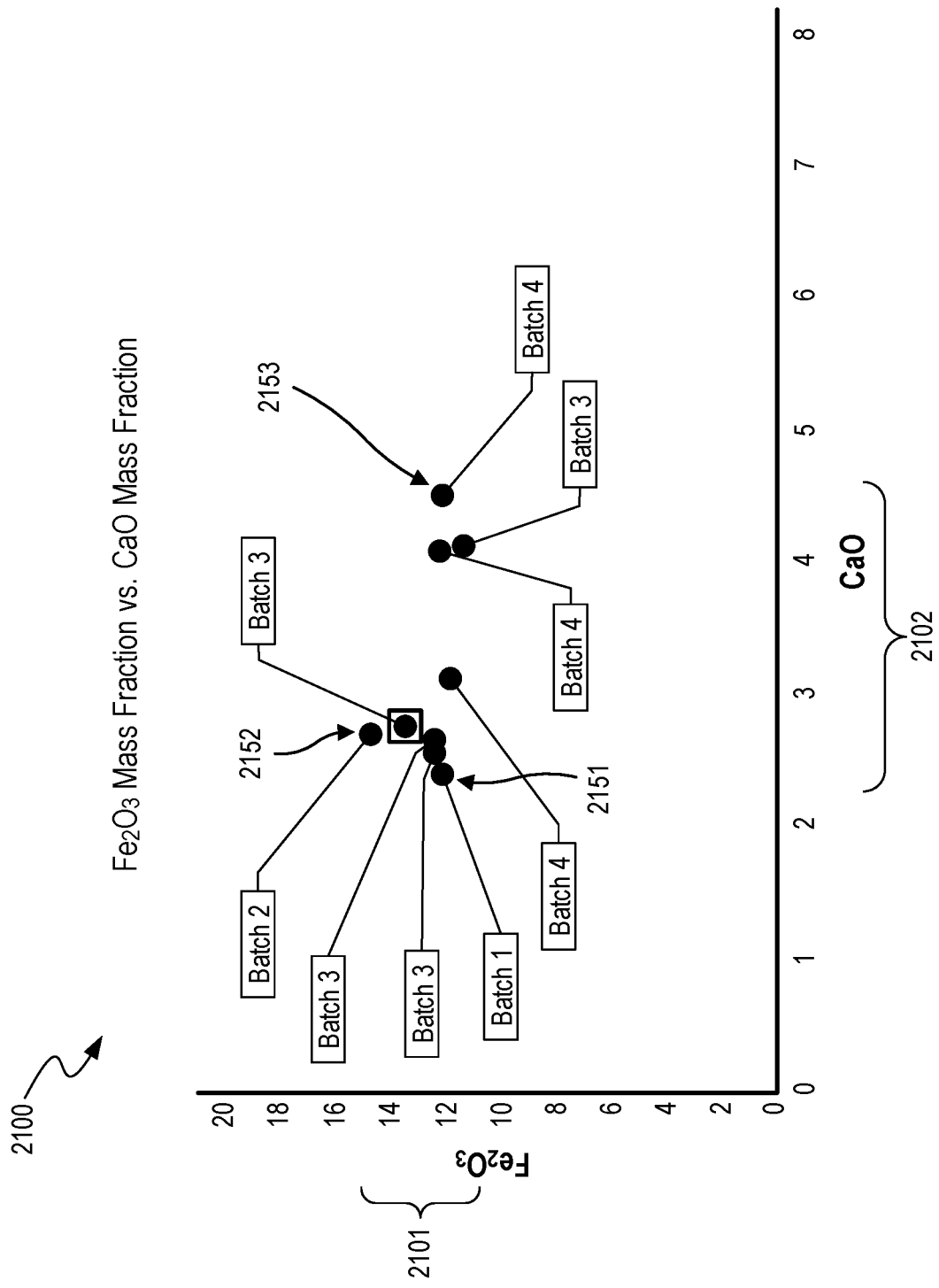
FIG. 21 is a chart depicting $Fe_2O_3$ mass fractions vs. CaO mass fractions in the ash of foundry coke products, in accordance with one or more embodiments of the present technology.

FIG. 21 is a chart depicting $Fe_2O_3$ mass fractions vs. CaO mass fractions in the ash of foundry coke products, in accordance with one or more embodiments of the present technology. In some embodiments, a coke product can be characterized based on their mass fractions of $Fe_2O_3$ and CaO or ratios of these mass fractions. As shown in the chart 2100, different data points representing coke ash samples can indicate different mass fractions and mass fraction ratios of $Fe_2O_3$ and CaO. For example, the point 2151 indicates a sample having an $Fe_2O_3$ mass fraction of approximately 12.1% and an CaO mass fraction of approximately 2.4%. Furthermore, the point 2152 indicates a sample having an $Fe_2O_3$ mass fraction of approximately 15.0% and an CaO mass fraction of approximately 2.8%. Furthermore, the point 2152 indicates a sample having an $Fe_2O_3$ mass fraction of approximately 12.0% and an CaO mass fraction of approximately 4.5%. Collectively, the points 2151 indicate that the mass fraction ratios of $Fe_2O_3$ and CaO for some samples can range between being approximately 5:1 to approximately 5:2 in some embodiments. Furthermore, as indicated by the range 2101, the $Fe_2O_3$ mass fractions of different samples can range between 11.0% and 15.0% in some embodiments. Furthermore, as indicated by the range 2102, the $Fe_2O_3$ mass fractions of CaO can range between 2.5% and 4.5% in some embodiments.

Some embodiments can produce a coke product using operations to increase the amount of CaO in a coke product. For example, some embodiments of the present technology can perform operations that produce coke products such that the ash of the coke products have a CaO mass fraction that is greater than or equal to 3.0%. Alternatively, or additionally, other maximum CaO thresholds can be used. For example, some embodiments of the present technology can produce coke products such that the ash of the coke products have a CaO mass fraction that is greater than or equal to 10.0%, greater than or equal to 9.0%, greater than or equal to 8.0%, greater than or equal to 7.0%, greater than or equal to 6.0%, greater than or equal to 5.0%, greater than or equal to 4.0%, greater than or equal to 3.0%, greater than or equal to 2.0%, greater than or equal to 1.0%, etc. Some embodiments can create a coke product from a coal blend having a high content of CaO, where this content can be determined by an ash composition. Such a high content of CaO can increase a carbon dissolution rate of the coke product.

Figure 22:
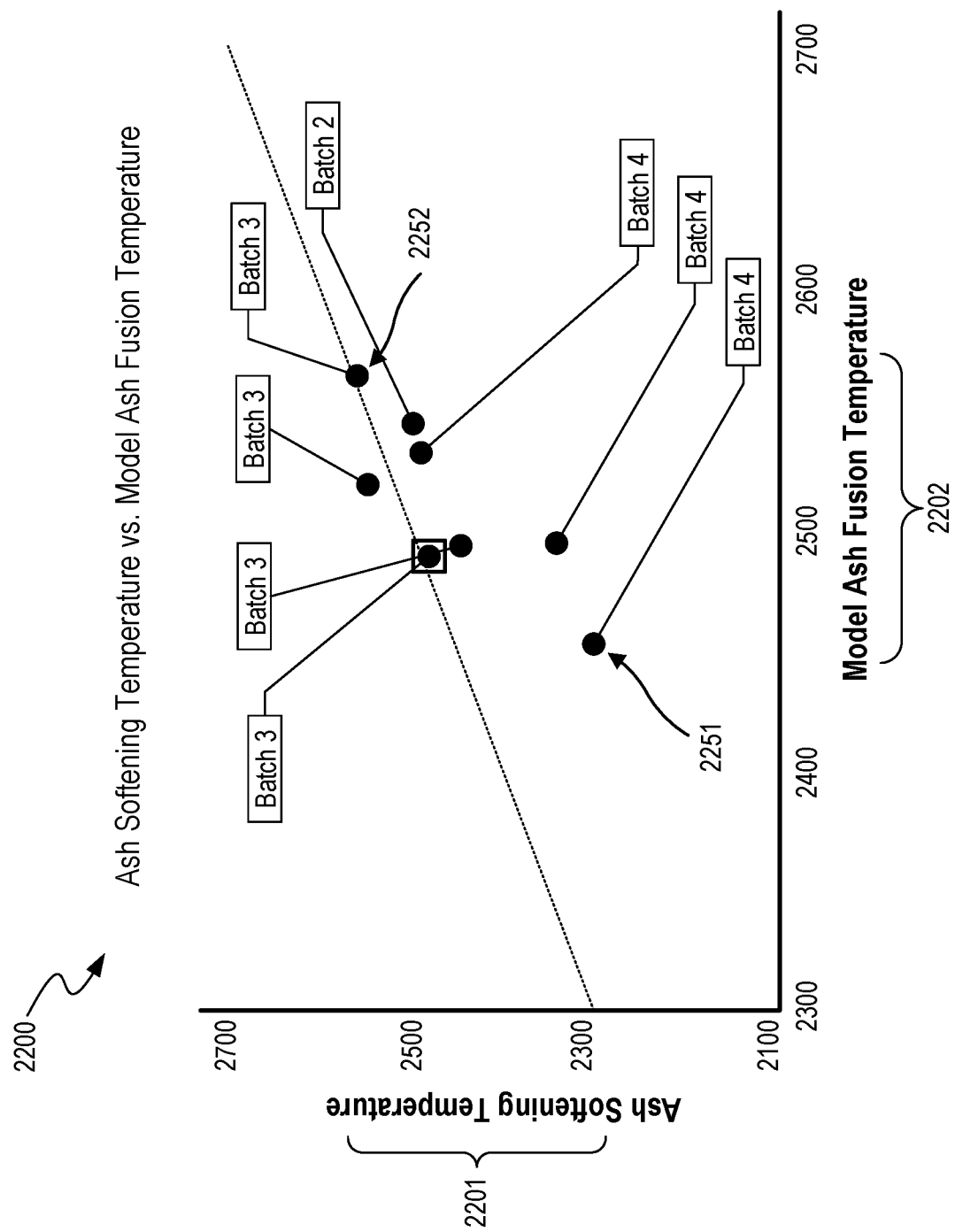
FIG. 22 is a chart depicting Ash Softening Temperatures vs. Model Ash Fusion Temperatures of different batches of foundry coke products, in accordance with one or more embodiments of the present technology.

FIG. 22 is a chart depicting Ash Softening Temperatures vs. Model Ash Fusion Temperatures of different batches of foundry coke products, in accordance with one or more embodiments of the present technology. In some embodiments, a coke product can be characterized based on their ash ST values, model AFT values, or ratios of these two values. As shown in the chart 2200, different samples of coke ash can have different ST and model AFT values. For example, the point 2251 indicates a sample having an ash ST value equal to approximately 2300° F. and a model AFT value equal to approximately 2460° F. Furthermore, the point 2252 indicates a sample having an ash ST value equal to approximately 2550° F. and a model AFT value equal to approximately 2580° F. Furthermore, as indicated by a range 2201, the ash ST value of different samples can range between 2300° F. and 2600° F. in some embodiments. Furthermore, as indicated by a range 2202, the model AFT values of some samples can range between 2450° F. and 2600° F. in some embodiments.

Figure 23:
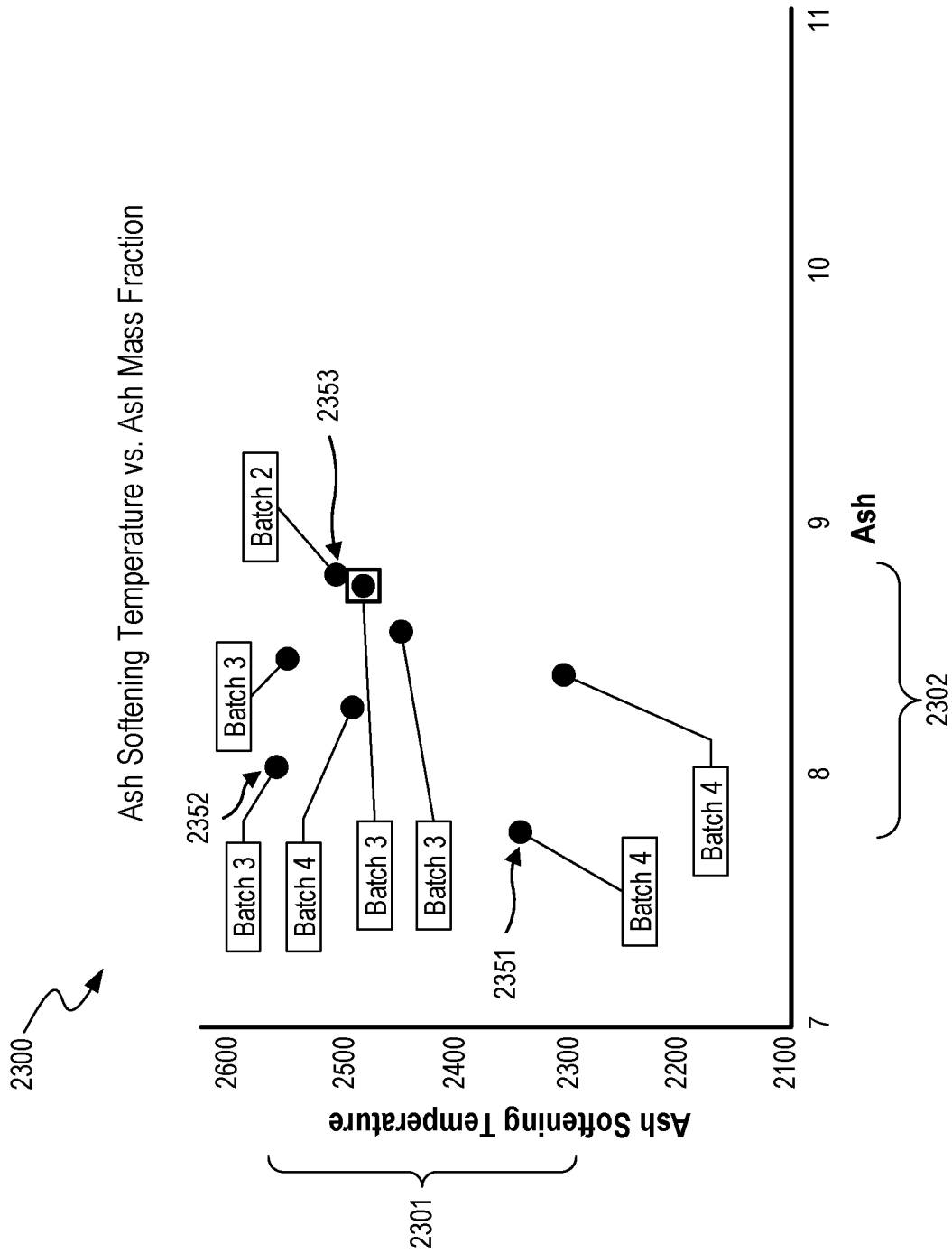
FIG. 23 is a chart depicting Ash Softening Temperatures vs. Ash Mass Fractions of different batches of foundry coke products, in accordance with one or more embodiments of the present technology.

FIG. 23 is a chart depicting Ash Softening Temperatures vs. Ash Mass Fractions of different batches of foundry coke products, in accordance with one or more embodiments of the present technology. In some embodiments, a coke product can be characterized based on their ash mass fractions or observed ash ST values. As shown in the chart 2300, different samples of coke ash can indicate different ash mass fractions and observed STs for the different ash samples. For example, the point 2351 indicates a sample having an ST value equal to approximately 2350° F. and an ash mass fraction of approximately 7.8%. Furthermore, the point 2152 indicates a sample having an ST value equal to approximately 2560° F. and an ash mass fraction of approximately 8.1%. Furthermore, the point 2153 indicates a sample having an ST value equal to approximately 2500° F. and an ash mass fraction of approximately 8.8%. Some embodiments can produce coke products having lower ash content and lower AFT than coke products using conventional coal blends or conventional operations. By reducing the ash of a coke product available to build up at a coke surface, some embodiments of the present technology can thus improve a carbon dissolution rate during a foundry operation. Similarly, by reducing an ash fusion temperature of a coke product, some embodiments of the present technology can improve an ash dissolution rate by reducing the temperature required to ash from a coke surface during a foundry operation.

In some embodiments, as indicated by the range 2301, the ash content values of different samples can range between 2300° F. and 2560° F. Furthermore, as indicated by the range 2302, the ash content can range between approximately 7.8% to 8.8%. As shown in the chart 2300, some embodiments of the present technology can produce a coke product having an ash mass fraction that is less than 10.0%, less than 9.0%, or less than another maximum ash mass fraction threshold. Furthermore, some embodiments of the present technology can perform operations to maintain a minimum amount of ash product. For example, some embodiments of the present technology can implement coke oven operations to produce coke products having at least 1.0% ash, 5.0% ash, 7.0% ash, etc.

Figure 24:
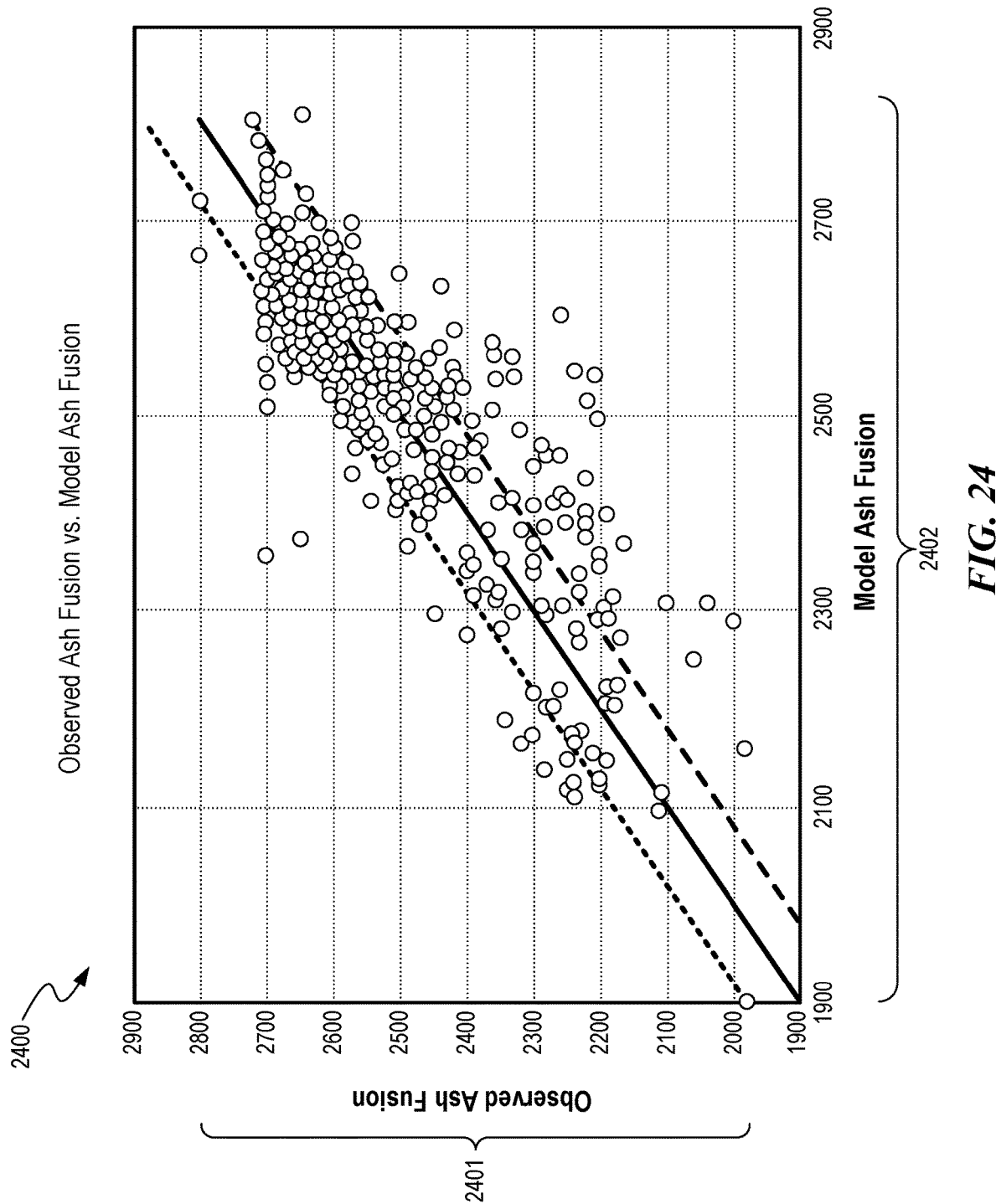
FIG. 24 is a chart depicting Observed Ash Fusion Temperatures vs. Model Ash Fusion Temperatures of different batches of foundry coke products, in accordance with one or more embodiments of the present technology.

FIG. 24 is a chart depicting Observed Ash Fusion Temperatures vs. Model Ash Fusion Temperatures of different batches of foundry coke products, in accordance with one or more embodiments of the present technology. The chart 2400 includes a first range 2401, which indicates the range of observed AFT values that range from approximately 1990° F. to approximately 2800° F. The chart 2400 includes a second range, which indicates the range of model AFT values that range between 1900° F. to 2750° F. As shown by the chart 2400, coke products can show an approximate direct correlation between model AFT values and observed AFT values.

From the foregoing, it will be appreciated that, although specific embodiments of the technology have been described herein for purposes of illustration, various modifications can be made without deviating from the spirit and scope of the technology. Further, certain aspects of the new technology described in the context of particular embodiments can be combined or eliminated in other embodiments. Moreover, while advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

V. Conclusion

It will be apparent to those having skill in the art that changes can be made to the details of the above-described embodiments without departing from the underlying principles of the present disclosure. In some cases, well known structures and functions have not been shown or described in detail to avoid unnecessarily obscuring the description of the embodiments of the present technology. Although steps of methods can be presented herein in a particular order, alternative embodiments can perform the steps in a different order. Similarly, certain aspects of the present technology disclosed in the context of particular embodiments can be combined or eliminated in other embodiments. Furthermore, while advantages associated with certain embodiments of the present technology can have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Reference herein to "one embodiment," "an embodiment," "some embodiments," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics can be combined in any suitable manner in one or more embodiments.

Unless otherwise indicated, all numbers expressing weight percentages, concentrations, compositions, and other numerical values used in the specification and claims, are to be understood as being modified in all instances by the term "approximately." Accordingly, unless indicated to the contrary, the numerical parameters set forth in the following specification and attached claims are approximations that can vary depending upon the desired properties sought to be obtained by the present technology. As used in this disclosure, unless otherwise disclosed, a value can be considered to be approximately a target value if a difference between the value and the target value is less than or equal to 10% of the target value. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10 (i.e., any and all subranges having a minimum value of equal to or greater than 1 and a maximum value of equal to or less than 10, e.g., 5.5 to 10).

Although the present invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

As used throughout this application, the word "can" is used in a permissive sense (i.e., meaning having the potential to), rather than the mandatory sense (i.e., meaning must). The words "comprise," "comprising," "include," "including," "includes," and the like mean including, but not limited to. As used throughout this application, the singular forms "a," "an," and "the" include plural referents unless the context clearly indicates otherwise. Thus, for example, reference to "an element" or "an element" includes a combination of two or more elements, notwithstanding use of other terms and phrases for one or more elements, such as "one or more."

Various other aspects, features, and advantages will be apparent through the detailed description of this disclosure and the drawings attached hereto. It is also to be understood that the description of this disclosure are examples, and not restrictive of the scope of the invention. As used in the specification and in the claims, the singular forms of "a," "an," and "the" include plural referents unless the context clearly dictates otherwise. Additionally, as used in the specification, "a portion" refers to a part of, or the entirety (i.e., the entire portion), of a given item (e.g., data) unless the context clearly dictates otherwise. Furthermore, a "set" can refer to a singular form or a plural form, such that a "set of items" can refer to one item or a plurality of items.

The term "or" is non-exclusive (i.e., encompassing both "and" and "or"), unless the context clearly indicates otherwise. Terms describing conditional relationships (e.g., "in response to X, Y," "upon X, Y," "if X, Y," "when X, Y," and the like) encompass causal relationships in which the antecedent is a necessary causal condition, the antecedent is a sufficient causal condition, or the antecedent is a contributory causal condition of the consequent (e.g., "state X occurs upon condition Y obtaining" is generic to "X occurs solely upon Y" and "X occurs upon Y and Z"). Such conditional relationships are not limited to consequences that instantly follow the antecedent obtaining, as some consequences can be delayed, and in conditional statements, antecedents are connected to their consequents (e.g., the antecedent is relevant to the likelihood of the consequent occurring). Statements in which a plurality of attributes or functions are mapped to a plurality of objects (e.g., one or more processors performing steps/operations A, B, C, and D) encompass both all such attributes or functions being mapped to all such objects and subsets of the attributes or functions being mapped to subsets of the objects (e.g., both all processors each performing steps/operations A-D, and a case in which processor 1 performs step/operation A, processor 2 performs step/operation B and part of step/operation C, and processor 3 performs part of step/operation C and step/operation D), unless otherwise indicated. Further, unless otherwise indicated, statements that one value or action is "based on" another condition or value encompass both instances in which the condition or value is the sole factor and instances in which the condition or value is one factor among a plurality of factors.

Unless the context clearly indicates otherwise, statements that "each" instance of some collection have some property should not be read to exclude cases where some otherwise identical or similar members of a larger collection do not have the property (i.e., each does not necessarily mean each and every). Limitations as to sequence of recited steps should not be read into the claims unless explicitly specified (e.g., with explicit language like "after performing X, performing Y"), in contrast to statements that might be improperly argued to imply sequence limitations (e.g., "performing X on items, performing Y on the X'ed items") used for purposes of making claims more readable rather than specifying sequence. Statements referring to "at least Z of A, B, and C" and the like (e.g., "at least Z of A, B, or C") refer to at least Z of the listed categories (A, B, and C) and do not require at least Z units in each category. Unless the context clearly indicates otherwise, it is appreciated that throughout this specification discussions utilizing terms such as "processing," "computing," "calculating," "determining," or the like refer to actions or processes of a specific apparatus, such as a special purpose computer or a similar special purpose electronic processing/computing device.

Enumerated Embodiments

The present technology is illustrated, for example, according to various aspects described below as numbered embodiments (1, 2, 3, etc.) for convenience. These are provided as examples and do not limit the present technology. It is noted that any of the dependent embodiments can be combined in any combination, and placed into a respective independent embodiment.

A1. A coal blend, comprising:
first coals having a first volatile matter mass fraction less than or equal to a first threshold; and
second coals having a second volatile matter mass fraction greater than or equal to a second threshold,
wherein:
the first threshold is less than the second threshold by at least 4.0%;
an ash fusion temperature of the coal blend is less than 2600° F.; and
the coal blend has an aggregated volatile matter mass fraction between 15% and 25%.

A2. A coal blend, comprising:
first coals having a first vitrinite fraction comprising V8 vitrinite fraction, V9 vitrinite fraction, V10 vitrinite fraction, and V11 vitrinite fraction, wherein a sum of the V8 vitrinite fraction, the V9 vitrinite fraction, the V10 vitrinite fraction, and the V11 vitrinite fraction is greater than 50%; and
first coals having a first vitrinite fraction comprising V14 vitrinite fraction, V15 vitrinite fraction, V16 vitrinite fraction, V17 vitrinite fraction, and V18 vitrinite fraction wherein a sum of the V14 vitrinite fraction, the V15 vitrinite fraction, the V16 vitrinite fraction, the V17 vitrinite fraction, and the V18 vitrinite fraction is greater than 50%.

A3. The coal blend of any one of embodiments A1 to A2, wherein the coal blend does not comprise any coals having a volatile mass fraction greater than the first threshold and less than the second threshold.

A4. The coal blend of any one of embodiment 1 to A3, wherein the coal blend comprises only the first coals and the second coals.

A5. The coal blend of any one of embodiments A1 to A4, wherein the first threshold is less than 21.0% and the second threshold is greater than 25.0%.

A6. The coal blend of any one of embodiments A1 to A5, wherein an ash fusion temperature of the coal blend is no more than 2450° F., 2400° F., 2350° F., 2300° F., 2250° F., 2200° F., or 1800° F.

A7. The coal blend of any one of embodiments A1 to A6, further comprising coke breeze.

A8. The coal blend of embodiment 6, wherein the coke breeze comprises 1-20% of the coal blend.

A9. The coal blend of any one of embodiments A7 to A8, wherein 5.0% or less of the coke breeze is characterized as a 10 mesh coke breeze or larger.

A10. The coal blend of any one of embodiments A6 to A8, wherein 10.0% or less of the coke breeze is characterized as a 20 mesh coke breeze or larger, or characterized as a 90 mesh coke breeze or smaller (15-25%).

A11. The coal blend of any one of embodiments A1 to A10, wherein:
the first coals are greater than or equal to 60% of the coal blend; and
the second coals are greater than or equal to 15% of the coal blend.

A12. The coal blend of any one of embodiments A1 to A11, wherein:
the first coals are greater than or equal to 15% of the coal blend; and
the second coals are greater than or equal to 60% of the coal blend.

A13. The coal blend of any one of embodiments A1 to A12, wherein a calcium oxide mass fraction, a lime mass fraction, a trona mass fraction, a soda ash mass fraction, a caustic soda mass fraction, a low ash fusion slag mass fraction, a basic oxygen furnace (BOF) slag mass fraction, a cupola slag mass fraction, an iron mass fraction, a nickel mass fraction, a potassium mass fraction, a magnesium mass fraction, a sodium mass fraction, a calcium sulfate mass fraction, a rockwool mass fraction, or a biomass mass fraction of the coal blend is less than 5.0%, or is less than 3.0%, or is less than 1.0%.

A14. The coal blend of any one of embodiments A1 to A13, wherein an ash mass fraction of the coal blend is greater than 10.0%, or is between 8.0%-10.0%, or is between 5.5-7.0%.

A15. The coal blend of any one of embodiments A1 to A14, wherein a fluidity of the coal blend is at least 100 dial divisions per minute (ddpm), 150 ddpm, 200 ddpm, 250 ddpm, 260 ddpm, 270 ddpm, 280 ddpm, 290 ddpm, or within a range of 250-300 ddpm.

A16. The coal blend of any one of embodiments A1 to A15, further comprising third coals having a third volatile matter mass fraction less than or equal to the first threshold.

A17. The coal blend of any one of embodiments A1 to A16, wherein the first coals have a V16 vitrinite mass fraction that is greater than 25%.

A18. The coal blend of any one of embodiments A1 to A17, wherein a sum of a V8 vitrinite fraction, a V9 vitrinite fraction, and a V10 vitrinite fraction of the second coals is greater than 40%.

A19. The coal blend of any one of embodiments A1 to A18, wherein a sulfur mass weight fraction of the coal blend is at least 5.0%.

A20. The coal blend of any one of embodiments A1 to A19, wherein a calcium weight fraction of the coal blend is at least 5.0%.

A21. The coal blend of any one of embodiments A1 to A20, wherein an inert content of the coal blend is greater than or equal to 32.0%, is between 33.0-35.0%, or is between 28.0-40.0%.

A22. The coal blend of any one of embodiments A1 to A21, wherein an alumina content of an ash of the coal blend is less than 7.0%.

A23. The coal blend of any one of embodiments A1 to A22, wherein the first threshold is 20% and the second threshold is 30%.

A24. A coal blend, comprising:
 first coals having a first volatile matter mass fraction less than or equal to a first threshold; and
 second coals having a second volatile matter mass fraction greater than or equal to a second threshold,
 wherein:
  the first threshold is less than 21.0%;
  the second threshold is greater than 25.0%;
  an ash fusion temperature of the coal blend is less than 2600° F. or is less than 2450° F.; and
  an aggregated volatile matter mass fraction of the coal blend is between 15% and 25%.

A25. The coal blend of embodiment A24, wherein the ash fusion temperature is less than 2300° F.

A26. The coal blend of any one of embodiments A24 to A25, wherein the ash fusion temperature is less than 2100° F.

A27. The coal blend of any one of embodiments A24 to A26, further comprising third coals having a third volatile matter mass fraction less than or equal to the first threshold, wherein the first coals and third coals each comprise V14 vitrinite, V15 vitrinite, V16 vitrinite, and V17 vitrinite.

A28. The coal blend of any one of embodiments A24 to A27, wherein:
 the first coals comprise V14 vitrinite, V15 vitrinite, and V16 vitrinite;
 a fraction of the V16 vitrinite of the first coals is greater than a fraction of the V15 vitrinite of the first coals; and
 the fraction of the V15 vitrinite of the first coals is greater than a fraction of the V14 vitrinite of the first coals.

A29. The coal blend of any one of embodiments A24 to A28, wherein the first threshold is less than 20.0%.

A30. The coal blend of any one of embodiments A24 to A29, wherein the second threshold is greater than 28%.

A31. The coal blend of any one of embodiments A24 to A30, wherein a difference between the first threshold and the second threshold is greater than 10%.

A32. A method of determining a coal blend for coke product production comprising:
 obtaining a plurality of coal parameters corresponding with first coals and second coals, wherein:
  the first coals have a first volatile matter mass fraction less than or equal to a first threshold; and
  the second coals have a second volatile matter mass fraction greater than or equal to a second threshold, wherein the first threshold is less than the second threshold by at least 4.0%;
 obtaining a target coke product parameter;
 determining a plurality of coke product parameters based on the plurality of coal parameters and the target coke product parameter; and
 based on the plurality of coke product parameters, determining a coal blend formulation for a coal blend comprising a combination of the first coals and the second coals.

A33. The method of embodiment A32, further comprising obtaining breeze parameters for coke breeze, wherein:
 the breeze parameters indicate at least one of a breeze volatile matter mass fraction, a breeze ash mass fraction, or a breeze sulfur mass fraction; and
 determining the coal blend formulation comprising determining an amount of coke breeze to add to the coal blend based on the breeze parameters.

A34. The method of any one of embodiments A32 to A33, wherein the first threshold is less than 21.0%, and wherein the second threshold is greater than 28.0%.

B1. A method of producing a coke product, the method comprising:
 adding water to a coal blend to increase a moisture content of the coal blend;
 charging the coal blend into a coke oven; and
 heating the charged coal blend such that, during a pyrolysis duration of a coking cycle for the charged coal blend, a crown temperature of the coke oven is greater than a lower bound coking temperature, wherein:
  the lower bound coking temperature is within a range of 1200-2300° F.;
  the pyrolysis duration begins when the crown of the oven is greater than the lower bound coking temperature;
  the pyrolysis duration ends when the crown temperature of the oven is less than the lower bound coking temperature; and
  the pyrolysis duration is greater than 24 hours.

B2. A method of embodiment B 1, wherein the lower bound coking temperature is within a range of 1800-2200° F.

B3. The method of any one of embodiments B1 to B2, wherein an upper limit of the crown temperature is limited by an upper bound coking temperature that is greater than 2300° F.

B4. The method of any one of embodiments B1 to B3, wherein an upper limit of the crown temperature is limited by an upper bound coking temperature that is greater than 2500° F.

B5. The method of embodiment B4, wherein the crown temperature is greater than a sole flue temperature of the coke oven throughout the pyrolysis duration.

B6. The method of any one of embodiments B1 to B5, wherein the crown temperature of the coke oven during the pyrolysis duration is between 2100-2300° F.

B7. The method of any one of embodiments B1 to B6, wherein the crown temperature is within a 100° F. temperature range during at least twelve hours of the pyrolysis duration.

B8. The method of any one of embodiments B1 to B7, wherein, during the pyrolysis duration, a sole flue temperature is below 2000° F., 1900° F., 1800° F., or 1700° F.

B9. The method of any one of embodiments B1 to B8, wherein, during the pyrolysis duration, a sole flue temperature is between 1400-1800° F.

B10. The method of any one of embodiments B1 to B9, wherein a soak time of the charged coal blend is less than 1.0 hour, 5.0 hours, or 10.0 hours.

B11. The method of any one of embodiments B1 to B10, wherein adding water to the coal blend comprises:
 determining whether a testing moisture of the coal blend satisfies a set of target moisture values; and in response to a determination that the testing moisture of the coal blend does not satisfy the set of target moisture values, exposing the coal blend to more water.

B12. The method of any one of embodiments B1 to B11, wherein a moisture weight fraction of the coal blend charged into the coke oven is at least 8.0%, 9.0%, 10.0%, 11.0%, 12.0%, or between 8.0-13%.

B13. The method of any one of embodiments B1 to B12, wherein adding water to the coal blend comprises adding water to a belt carrying the coal blend.

B14. The method of any one of embodiments B1 to B13, wherein adding water to the coal blend is based on a volatile matter of the coal blend.

B15. The method of any one of embodiments B1 to B14, wherein adding water to the coal blend comprises adding water such that a moisture content of the charged coal is approximately equal to or within 1-5% of a volatile matter mass fraction of the coal blend.

B16. The method of any one of embodiments B1 to B15, wherein the pyrolysis duration is approximately 48 hours.

B17. The method of embodiment B16, wherein the pyrolysis duration is approximately 72 hours.

B18. The method of any one of embodiments B1 to B17, wherein a volatile matter mass fraction of the coal blend is less than 27.0%.

B19. The method of any one of embodiments B1 to B18, wherein the coke oven includes an uptake damper movable to a plurality of positions between open and closed, and wherein heating the coal blend comprises maintaining the uptake damper of the coke oven in a position less than half-way open during a majority of the first 24 hours of the coking cycle.

B20. The method of any one of embodiments B1 to B19, wherein the coke oven includes an uptake damper movable to a plurality of positions between open and closed, and wherein heating the coal blend comprises maintaining the uptake damper of the coke oven in a position less than half-way open during a majority of the coking cycle.

B21. The method of any one of embodiments B1 to B20, wherein heating the coal blend comprises:
opening an uptake damper at the beginning of the coking cycle;
performing, within two hours of charging the coal blend, a first closure operation of the uptake damper from a first configuration to a second configuration, wherein flow through an uptake duct of the coke oven while the uptake damper is in the second configuration is less than flow through the uptake duct while the uptake damper is in the first configuration.

B22. The method of embodiment B21, wherein heating the coal blend is based on a temperature change rate being no more than a temperature rate threshold, wherein the temperature rate threshold is less than or equal to 50° F. per hour.

B23. The method of any one of embodiments B1 to B22, wherein heating the coal blend comprises closing a sole flue damper or maintaining the sole flue damper in a closed position for a majority of the pyrolysis duration.

B24. The method of any one of embodiments B1 to B23, wherein heating the coal blend comprises closing a sole flue damper or maintaining the sole flue damper in a closed position for a majority of the coking cycle.

B25. The method of any one of embodiments B1 to B24, wherein a ratio of the soak time to a cycle duration of the charged coal blend is less than 33.0%, 15%, or 5%.

B26. A method, comprising:
heating the coal blend within a coke oven to a coking temperature during a pyrolysis duration of a coking, wherein:
the pyrolysis duration begins when a crown of the oven is greater than a lower bound coking temperature;
the pyrolysis duration ends when the crown of the oven is less than the lower bound coking temperature;
the lower bound coking temperature is within a range of 1200-2300° F.

B27. The method of embodiment B26, wherein, for at least 12 hours of the pyrolysis duration, the coking temperature varies no more than 75° F., 60° F., 50° F., 40° F., or 35° F.

B28. The method of any one of embodiments B26 to B27, further comprising:
opening an uptake damper of the coke oven;
beginning a closure operation of the uptake damper at least two hours, four hours, six hours, eight hours, ten hours, or twelve hours after opening the uptake, wherein the closure operation closes the uptake damper to a position less than half-way open; and
maintaining the uptake damper at no more open than the position for at least twelve hours, sixteen hours, or twenty hours after beginning the closure operation.

B29. The method of any one of embodiments B26 to B28, wherein the coal blend comprises coke breeze, and wherein an ash mass fraction of the coke breeze is greater than or equal to 6.5%, 7.0%, 10.0%, 13%, 15%, or 20%.

B30. The method of any one of embodiments B26 to B29, wherein the coal blend comprises coke breeze, and wherein an ash mass fraction of the coke breeze is greater than or equal to 15.0%.

B31. The method of any one of embodiments B26 to B30, wherein an ash fusion temperature of the coal blend is no more than 2400° F., 2350° F., 2300° F., 2250° F., 2200° F., 2000° F., or 1800° F.

B32. The method of any one of embodiments B26 to B31, wherein a fluidity of the coal blend is at least 100 dial divisions per minute (ddpm), 150 ddpm, 250 ddpm, 260 ddpm, 270 ddpm, 280 ddpm, 290 ddpm, 300 ddpm, 350 ddpm, 400 ddpm, or 100-400 ddpm.

B33. The method of any one of embodiments B26 to B35, wherein an aggregated volatile matter mass fraction of the coal blend is between 18-22%.

B34. A coke oven, comprising:
an oven chamber comprising a crown and a sole flue;
an uptake duct in fluid communication with the oven chamber, the uptake duct being configured to receive exhaust gases from the oven chamber;
an uptake damper in fluid communication with the uptake duct, the uptake damper being positioned at any one of a plurality of positions including fully opened and closed, wherein a manipulation of the uptake damper between positions configures an air flow through the uptake duct;
a damper actuator configured to alter the position of the uptake damper between the plurality of positions;
a common tunnel in fluid communication with the uptake duct, the common tunnel being configured to receive exhaust gases from the uptake duct; and
a controller configured to perform operations during a coking cycle, the operations comprising heating a coal blend within a coke oven to a coking temperature during a pyrolysis duration of a coking cycle, wherein:
the pyrolysis duration begins when a crown of the oven is greater than a lower bound coking temperature;

the pyrolysis duration ends when the crown of the oven is less than the lower bound coking temperature;

the lower bound coking temperature is within a range of 1200-2300° F.; and a sole flue temperature remains below a crown temperature throughout the pyrolysis duration.

B35. The coke oven of embodiment B34, the controller is further configured to perform operations comprising:

opening an uptake damper at the beginning of the coking cycle;

performing, within two hours of charging the coal blend, a first closure operation of the uptake damper from a first configuration to a second configuration, wherein flow through an uptake duct of the coke oven while the uptake damper is in the second configuration is less than flow through the uptake duct while the uptake damper is in the first configuration.

B36. The coke oven of any of embodiments B34 to B35, wherein a moisture weight fraction of the coal blend is between 10-12% before heating the coal blend.

C1. A coke product, configured to be combusted in a cupola furnace, wherein the coke product is produced by operations comprising:

heating a coal blend in a coke oven to a lower bound coking temperature, wherein a pyrolysis duration begins when a crown temperature of the coke oven reaches the lower bound coking temperature, and wherein the crown temperature is greater than a sole flue temperature of the coke oven during the pyrolysis duration; and removing a coke product produced from the coal blend from the coke oven, wherein a Coke Reactivity Index of the coke product is at least 30%.

C2. The coke product of embodiment C1, wherein the coke product comprises:

an oblong shape;

a first dimension between 6.0-12.0 inches; and a second dimension, normal to the first dimension, greater than 2.5 inches.

C3. The coke product of any one of embodiments C1 to C2, wherein the operations further comprise:

prior to heating the coal blend, charging the coal blend in the coke oven, wherein:

the coal blend comprises first coals and second coals;

the first coals have a first volatile matter mass fraction less than or equal to 21.0%;

the second coals have a second volatile matter mass fraction greater than or equal to 27.0%;

the coal blend does not comprise coals having a volatile matter mass fraction that is between 15.0% and 27.0%.

C4. The coke product of any one of embodiments C1 to C3, wherein the coking rate is less than 1 ton of coal blend charge per hour, less than 0.75 ton of coal blend charge per hour, or less than 0.50 ton of coal blend charge per hour.

C5. The coke product of any one of embodiments C1 to C4, wherein an ash fusion temperature of the coke product is less than 1800° F. or 2450° F.

C6. The coke product of any one of embodiments C1 to C5, wherein the Coke Reactivity Index of the coke product is at least 35.0%, 40.0%, or 45.0%.

C7. The coke product of any one of embodiments C1 to C6, wherein the coke product has a Coke Strength after Reaction (CSR) that is greater than or equal to 1.0%.

C8. The coke product of any one of embodiments C1 to C7, wherein the coke product has a Coke Reactivity Index (CRI) between 25% and 65% and a Coke Strength after Reaction (CSR) that is greater than or equal to 1%.

C9. The coke product of any one of embodiments C1 to C8, wherein the coke product has a 2-inch drop shatter that is greater than or equal to 90%.

C10. The coke product of any one of embodiments C1 to C9, wherein the coke product has a 4-inch drop shatter that is greater than or equal to 80%.

C11. The coke product of any one of embodiments C1 to C10, wherein producing the coke product further comprises performing a closing operation of an uptake damper of the coke oven within four hours of a start of the pyrolysis duration.

C12. A population of coke products, wherein the population of coke products is produced by operations comprising:

heating a coal blend in a coke oven to a lower bound coking temperature, wherein a pyrolysis duration begins when a crown temperature of the coke oven reaches the lower bound coking temperature; and performing a closing operation of an uptake damper of the coke oven within four hours of a start of the pyrolysis duration, wherein the crown temperature is greater than a sole flue temperature of the coke oven during the pyrolysis duration, and wherein the population of coke products comprises foundry coke products having a Coke Reactivity Index of at least 30%, egg coke products, and coke breeze products.

C13. The population of coke products of any one of embodiments C12, wherein:

the foundry coke products comprise at least 40% of the population of coke products; and the egg coke products and the coke breeze products comprise at least 20% of the population.

C14. The population of coke products of embodiment C13, wherein:

the foundry coke products comprise at least 60% of the population of coke products; and the egg coke products and the coke breeze products comprise at least 20% of the population of coke products.

C15. The population of coke products of any one of embodiments C12 to C14, wherein a mass fraction of ash in the foundry coke products is between 5.0% and 10.0%.

C16. The population of coke products of any one of embodiments C12 to C15, wherein a volatile matter mass fraction of the foundry coke products is less than 1.0%.

C17. The population of coke products of any one of embodiments C12 to C16, wherein a product of the foundry coke products has a 4-inch drop shatter that is greater than or equal to 80%.

C18. The population of coke products of any one of embodiments C12 to C17, wherein the coal blend has volatile matter between 15% and 40%, and wherein the coal blend has a fluidity that is greater than or equal to 100 dial division per minute.

C19. The population of coke products of any one of embodiments C12 to C18, wherein a product of the egg coke products has a hydraulic diameter that is less than 2.0 inches.

C20. A coke product, wherein the coke product is produced by operations comprising heating a coal blend in a coke oven to a lower bound coking temperature to produce a coke product, wherein:

a pyrolysis duration begins when a crown temperature of the coke oven reaches the lower bound coking temperature;

the crown temperature is greater than a sole flue temperature of the coke oven during the pyrolysis duration; and
an ash fusion temperature of the coke product is less than 2300° F., less than 2400° F., or less than 2600° F.

C21. The coke product of embodiment C20, wherein the operations further comprise:
increasing a moisture of the coal blend to a moisture of at least 5.0%, 7.5%, or 10.0%; and charging the coal blend into the coke oven after increasing the moisture of the coal blend.

D1. A coke product, comprising:
a Coke Reactivity Index (CRI) of at least 30%; and
an ash fusion temperature (AFT) no more than 1316° C.

D2. A coke product, comprising:
an ash having a composition that satisfies the following equation:

Ash Fusion Temperature (AFT)=19×(Al$_2$O$_3$_mass_fraction)+15×(SiO$_2$_mass_fraction+TiO$_2$_mass_fraction)+10×(CaO_mass_fraction+MgO_mass_fraction)+6×(Fe$_2$O$_3$_mass_fraction+Na$_2$O_mass_fraction), wherein:
the AFT is a value between 1204° C. and 1426° C.;
the SiO$_2$_mass_fraction is an SiO 2 mass fraction of the ash;
the Al$_2$O$_3$_mass_fraction is an Al$_2$O$_3$ mass fraction of the ash;
the Fe$_2$O$_3$_mass_fraction is an Fe$_2$O$_3$ mass fraction of the ash;
the CaO_mass_fraction is a CaO mass fraction of the ash; and
the MgO_mass_fraction is an MgO mass fraction of the ash.

D3. A coke product, comprising:
an ash having a composition that satisfies the following equation:

Ash Fusion Temperature (AFT)=19×(Al$_2$O$_3$_mass_fraction)+15×(SiO$_2$_mass_fraction+TiO$_2$_mass_fraction)+10×(CaO_mass_fraction+MgO_mass_fraction)+6×(Fe$_2$O$_3$_mass_fraction+Na$_2$O_mass_fraction+K$_2$O_mass_fraction), wherein:
the AFT is a value between 982° C. and 1426° C.;
the SiO$_2$_mass_fraction is an SiO$_2$ mass fraction of the ash;
the Al$_2$O$_3$_mass_fraction is an Al$_2$O$_3$ mass fraction of the ash;
the Fe$_2$O$_3$_mass_fraction is an Fe$_2$O$_3$ mass fraction of the ash;
the CaO_mass_fraction is a CaO mass fraction of the ash;
the MgO_mass_fraction is an MgO mass fraction of the ash; and
the K$_2$O_mass_fraction is an K$_2$O mass fraction of the ash.

D4. A coke product, comprising:
an ash having a composition that satisfies the following equation:

Ash Fusion Temperature (AFT)=401.5+26.3×SiO$_2$_mass_fraction+40.7×Al$_2$O$_3$_mass_fraction−11.0×Fe$_2$O$_3$_Mass_Fraction−7.9×CaO_mass_fraction−112×MgO_mass_fraction, wherein:
the AFT is a value between 982° C. and 1204° C.;
the SiO$_2$_mass_fraction is an SiO$_2$ mass fraction of the ash;
the Al$_2$O$_3$_mass_fraction is an Al$_2$O$_3$ mass fraction of the ash;
the Fe$_2$O$_3$_mass_fraction is an Fe$_2$O$_3$ mass fraction of the ash;
the CaO_mass_fraction is a CaO mass fraction of the ash;
the MgO_mass_fraction is an MgO mass fraction of the ash.

D5. The coke product of any one of embodiments D1 to D4, wherein the AFT is approximately equal to at least one of 1204° C., 1260° C., 1288° C., 1316° C., 1343° C., 1371° C., 1399° C., or 1427° C.

D6. The coke product of any one of embodiments D1 to D5, wherein the coke product has an initial deformation temperature between 1149° C. and 1316° C.

D7. The coke product of any one of embodiments D1 to D6, wherein the coke product has a softening temperature between 1177° C. and 1371° C.

D8. The coke product of any one of embodiments D1 to D7, wherein the coke product has a hemispherical temperature between 1204° C. and 1371° C.

D9. The coke product of any one of embodiments D1 to D8, wherein the coke product has a fluid temperature between and 1232° C. and 1427° C.

D10. The coke product of any one of embodiments D1 to D9, wherein a mass fraction of the ash of the coke product is no more than 10.0%.

D11. The coke product of any one of embodiments D1 to D10, wherein a mass fraction of sulfur or sulfur oxide of the coke product is no more than 1.0%.

D12. The coke product of any one of embodiments D1 to D11, wherein:
the coke product is produced from a coal blend comprising ash including Al$_2$O$_3$ and SiO$_2$; and
a combined mass fraction of the Al$_2$O$_3$ and SiO$_2$ of the ash is no more than 65%.

D13. The coke product of any one of embodiments D1 to D12, wherein the AFT is approximately 1204° C.

D14. The coke product of any one of embodiments D1 to D13, wherein:
the coke product is produced from a coal blend comprising ash including Al$_2$O$_3$ and SiO$_2$; and
a combined mass fraction of the Al$_2$O$_3$ and the SiO$_2$ of the ash is between 65% and 80%.

D15. The coke product of any one of embodiments D1 to D14, wherein the AFT is between 1204° C. and 1260° C.

D16. The coke product of any one of embodiments D1 to D15, wherein:
the coke product is made from a coal blend comprising ash including CaO; and
a CaO mass fraction of the ash is at least 2.0%.

D17. The coke product of any one of embodiments D1 to D16, wherein the coke product has a coke reactivity index (CRI) of is at least 25.0%.

D18. The coke product of any one of embodiments D1 to D17, wherein the coke product has a Coke Strength After Reaction (CSR) that is no more than 40.0%.

D19. The coke product of any one of embodiments D1 to D18, wherein the coke product has a 2-inch drop shatter of at least 90%.

D20. The coke product of any one of embodiments D1 to D19, wherein the coke product has a 4-inch drop shatter of at least 80%.

D21. The coke product of any one of embodiments D1 to D20, wherein a mass fraction of the ash of the coke product is at least 8.0%.

D22. The coke product of any one of embodiments D1 to D21, wherein a volatile matter mass fraction of the coke product is no more than 1.0%.

D23. The coke product of any one of embodiments D1 to D22, wherein a fixed carbon content of the coke product is at least 94.5%.

D24. The coke product of any one of embodiments D1 to D23, wherein a fixed carbon content of the coke product is at least 85.0%.

D25. The coke product of any one of embodiments D1 to D24, wherein the coke product comprises at least $Na^{+1}$, $Fe^{2+}$, or $F^{3+}$.

We claim:

1. A method of producing a coke product, the method comprising:
adding water to a coal blend;
charging the coal blend into a coke oven; and
heating the charged coal blend such that, during a pyrolysis duration of a coking cycle for the charged coal blend, a crown temperature of the coke oven is greater than a lower bound coking temperature,
wherein:
the lower bound coking temperature is within a range of 1200-2300° F.;
the pyrolysis duration begins when the crown temperature of the oven is greater than the lower bound coking temperature;
the pyrolysis duration ends when the crown temperature of the oven is less than the lower bound coking temperature;
the crown temperature is greater than a sole flue temperature of the coke oven throughout the pyrolysis duration; and
the pyrolysis duration is greater than 24 hours.

2. The method of claim 1, wherein the lower bound coking temperature is within a range of 1800-2200° F.

3. The method of claim 1, wherein an upper limit of the crown temperature is limited by an upper bound coking temperature that is greater than 2300° F.

4. The method of claim 1, wherein the crown temperature of the coke oven during the pyrolysis duration is 2100-2300° F.

5. The method of claim 1, wherein the crown temperature is within a 100° F. temperature range during at least twelve hours of the pyrolysis duration.

6. The method of claim 1, wherein, during the pyrolysis duration, a sole flue temperature is below 2000° F.

7. The method of claim 1, wherein, during the pyrolysis duration, a sole flue temperature is 1400-1800° F.

8. The method of claim 1, wherein a soak time of the charged coal blend is less than 10.0 hours.

9. The method of claim 1, wherein adding water to the coal blend comprises:
determining whether a testing moisture of the coal blend satisfies a target moisture value; and
in response to a determination that the testing moisture of the coal blend does not satisfy the target moisture values, adding water to the coal blend.

10. The method of claim 1, wherein a moisture weight fraction of the coal blend charged into the coke oven is at least 8.0%.

11. The method of claim 1, wherein adding water to the coal blend comprises adding water to a belt carrying the coal blend.

12. The method of claim 1 wherein adding water to the coal blend is based on a volatile matter of the coal blend.

13. The method of claim 1, wherein adding water to the coal blend comprises adding water such that a moisture content of the charged coal is no more than 5% smaller or larger than a volatile matter mass fraction of the coal blend.

14. The method of claim 1, wherein the pyrolysis duration is approximately 48 hours.

15. The method of claim 1, wherein a volatile matter mass fraction of the coal blend is less than 27.0%.

16. The method of claim 1, wherein the coke oven includes an uptake damper movable to a plurality of positions between open and closed, and wherein heating the coal blend comprises maintaining the uptake damper of the coke oven in a position less than half-way open during a majority of an initial 24 hours of the coking cycle.

17. The method of claim 1, wherein heating the coal blend is based on a temperature change rate being no more than a temperature rate threshold that is less than or equal to 50° F. per hour.

18. The method of claim 1, wherein heating the coal blend comprises closing a sole flue damper or maintaining the sole flue damper in a closed position for a majority of the pyrolysis duration.

19. The method of claim 1, wherein a ratio of a soak time of the charged coal blend to a cycle duration of the charged coal blend is less than 33.0%.

20. A method, comprising:
heating a coal blend within a coke oven to a coking temperature during a pyrolysis duration of a coking,
wherein:
the pyrolysis duration begins when a crown temperature of the oven is greater than a lower bound coking temperature;
the pyrolysis duration ends when the crown temperature of the oven is less than the lower bound coking temperature;
the lower bound coking temperature is within a range of 1200-2300° F.;
the crown temperature is greater than a sole flue temperature of the coke oven throughout the pyrolysis duration; and
the pyrolysis duration is greater than 24 hours.

21. The method of claim 20, wherein, for at least 12 hours of the pyrolysis duration, the coking temperature varies no more than 75° F.

* * * * *

UNITED STATES PATENT AND TRADEMARK OFFICE
CERTIFICATE OF CORRECTION

| | |
|---|---|
| PATENT NO. | : 12,286,591 B2 |
| APPLICATION NO. | : 18/501795 |
| DATED | : April 29, 2025 |
| INVENTOR(S) | : John Francis Quanci et al. |

It is certified that error appears in the above-identified patent and that said Letters Patent is hereby corrected as shown below:

On the Title Page

On Page 7, Column 2 item (56) (Other Publications), Line 58, delete "Lond," and insert --London,-- therefor.

On Page 8, Column 1 item (56) (Other Publications), Line 25, delete "abestos,"" and insert --asbestos,"-- therefor.

On Page 8, Column 1 item (56) (Other Publications), Line 31, delete "Systgem" and insert --System-- therefor.

On Page 10, Column 1 item (56) (Other Publications), Line 57, delete "3, 3021," and insert --3, 2021,-- therefor.

In the Drawings

On Sheet 1 of 24, Fig. 1, Reference Numeral 116, Line 2, delete "116" and insert --115-- therefor.

On Sheet 5 of 24, Fig. 5, Row 3, Line 1, delete "SiO2" and insert --$SiO_2$-- therefor.

On Sheet 5 of 24, Fig. 5, Row 4, Line 1, delete "Al2O3" and insert --$Al_2O_3$-- therefor.

On Sheet 5 of 24, Fig. 5, Row 5, Line 1, delete "Fe2O3" and insert --$Fe_2O_3$-- therefor.

On Sheet 5 of 24, Fig. 5, Row 6, Line 1, delete "TiO2" and insert --$TiO_2$-- therefor.

On Sheet 5 of 24, Fig. 5, Row 9, Line 1, delete "Na2O" and insert --$Na_2O$-- therefor.

Signed and Sealed this
Twentieth Day of January, 2026

John A. Squires
*Director of the United States Patent and Trademark Office*

CERTIFICATE OF CORRECTION (continued)  Page 2 of 2
U.S. Pat. No. 12,286,591 B2

On Sheet 5 of 24, Fig. 5, Row 10, Line 1, delete "K2O" and insert --$K_2O$-- therefor.

On Sheet 5 of 24, Fig. 5, Row 11, Line 1, delete "P2O5" and insert --$P_2O_5$-- therefor.

On Sheet 5 of 24, Fig. 5, Row 12, Line 1, delete "SO3" and insert --$SO_3$-- therefor.

On Sheet 6 of 24, Fig. 6, Row 3, Line 1, delete "SiO2" and insert --$SiO_2$-- therefor.

On Sheet 6 of 24, Fig. 6, Row 4, Line 1, delete "Al2O3" and insert --$Al_2O_3$-- therefor.

On Sheet 6 of 24, Fig. 6, Row 5, Line 1, delete "Fe2O3" and insert --$Fe_2O_3$-- therefor.

On Sheet 6 of 24, Fig. 6, Row 6, Line 1, delete "TiO2" and insert --$TiO_2$-- therefor.

On Sheet 6 of 24, Fig. 6, Row 9, Line 1, delete "Na2O" and insert --$Na_2O$-- therefor.

On Sheet 6 of 24, Fig. 6, Row 10, Line 1, delete "K2O" and insert --$K_2O$-- therefor.

On Sheet 6 of 24, Fig. 6, Row 11, Line 1, delete "P2O5" and insert --$P_2O_5$-- therefor.

On Sheet 6 of 24, Fig. 6, Row 12, Line 1, delete "SO3" and insert --$SO_3$-- therefor.

On Sheet 12 of 24, Fig. 12, Row 5, Line 1, delete "Al2O3" and insert --$Al_2O_3$-- therefor.

In the Specification

In Column 4 (Detailed Description), Line 47, delete "116" and insert --115-- therefor.

In Column 4 (Detailed Description), Line 51, delete "110 coals" and insert --coals 110-- therefor.

In Column 7 (Detailed Description), Line 63, delete "SiO 2" and insert --$SiO_2$-- therefor.

In Column 32 (Detailed Description), Line 31, delete "SiO 2" and insert --$SiO_2$-- therefor.

In Column 40 (Detailed Description), Line 34, delete "B 1," and insert --B1,-- therefor.

In Column 45 (Detailed Description), Line 25, delete "SiO 2" and insert --$SiO_2$-- therefor.